(12) United States Patent
Bi et al.

(10) Patent No.: US 8,473,069 B2
(45) Date of Patent: Jun. 25, 2013

(54) INTEGRATED CIRCUIT IMPLEMENTATION AND FAULT CONTROL SYSTEM, DEVICE, AND METHOD

(75) Inventors: Yafei Bi, Fremont, CA (US); Haifeng Li, Sunnyvale, CA (US); Mark Zdeblick, Portola Valley, CA (US); Todd Thompson, San Jose, CA (US); Robert Leichner, Menlo Park, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

(21) Appl. No.: 12/920,086

(22) PCT Filed: Feb. 27, 2009

(86) PCT No.: PCT/US2009/035586
§ 371 (c)(1),
(2), (4) Date: Oct. 22, 2010

(87) PCT Pub. No.: WO2009/131749
PCT Pub. Date: Oct. 29, 2009

(65) Prior Publication Data
US 2011/0034964 A1    Feb. 10, 2011

Related U.S. Application Data

(60) Provisional application No. 61/032,356, filed on Feb. 28, 2008, provisional application No. 61/046,709, filed on Apr. 21, 2008, provisional application No. 61/055,097, filed on May 21, 2008, provisional application No. 61/121,128, filed on Dec. 9, 2008.

(51) Int. Cl.
*A61N 1/08*    (2006.01)

(52) U.S. Cl.
USPC .................................................. 607/63; 607/9

(58) Field of Classification Search
USPC .................................. 607/5, 9, 30, 37, 63, 116
See application file for complete search history.

(56) References Cited

U.S. PATENT DOCUMENTS 2,956,586 A    10/1960    Zeigler et al.
3,888,260 A     6/1975    Fischell
(Continued)

FOREIGN PATENT DOCUMENTS

EP    0659388    6/1995
EP    1048321    11/2000
(Continued)

OTHER PUBLICATIONS

Auricchio et al., "The Pacing Therapies for Congestive Heart Failure (PATH-CHF) Study: Rational, Design and Endpoints of a Prospective Randomized Multicenter Study" Am J. Cardio.: 83:130D-135D (1999).

(Continued)

*Primary Examiner* — Tammie K Heller
(74) *Attorney, Agent, or Firm* — Bozicevic, Field & Francis LLP; Bret E. Field

(57) ABSTRACT

Apparatus and methods enable robust, reliable control for implantable medical devices, including cardiac pacemakers, defibrillators and cardiac resynchronization devices. Integrated circuits in the devices have minimized interfaces, can derive power from the interface signals, and have high voltage and latch-up protection. A device lead has a power generation circuit and a switching circuit using cascaded PMOS transistors for operating with a stable voltage despite fluctuations in the supplied voltage. The lead has control electronics that provide a very low impedance between an electrode and a lead conductor during most of the duration of a pacing pulse, but during a brief initial portion of the pacing pulse, provide a very high impedance to permit charging up a power supply that is local to the control electronics. A method of stabilizing the external impedance and a system for fault detection and fault recovery for an implantable device are also provided.

11 Claims, 39 Drawing Sheets

U.S. PATENT DOCUMENTS

| | | |
|---|---|---|
| 3,985,123 A | 10/1976 | Herzlinger et al. |
| 4,164,946 A | 8/1979 | Langer |
| 4,262,982 A | 4/1981 | Kenny |
| 4,397,314 A | 8/1983 | Vaguine |
| 4,399,820 A | 8/1983 | Wirtzfeld et al. |
| 4,600,454 A | 7/1986 | Plummer |
| 4,603,705 A | 8/1986 | Speicher et al. |
| 4,628,934 A | 12/1986 | Pohndorf et al. |
| 4,628,935 A | 12/1986 | Jones et al. |
| 4,750,494 A | 6/1988 | King |
| 4,776,334 A | 10/1988 | Prionas |
| 4,815,472 A | 3/1989 | Wise et al. |
| 4,877,032 A | 10/1989 | Heinze et al. |
| 4,878,898 A | 11/1989 | Griffin et al. |
| 4,881,410 A | 11/1989 | Wise et al. |
| 4,902,273 A | 2/1990 | Choy et al. |
| 5,004,275 A | 4/1991 | Miller |
| 5,005,613 A | 4/1991 | Stanley |
| 5,072,737 A | 12/1991 | Goulding |
| 5,111,816 A | 5/1992 | Pless et al. |
| 5,113,868 A | 5/1992 | Wise et al. |
| 5,119,852 A | 6/1992 | Von Benda |
| 5,156,154 A | 10/1992 | Valenta, Jr. et al. |
| 5,158,536 A | 10/1992 | Sekins et al. |
| 5,176,619 A | 1/1993 | Segalowitz |
| 5,188,106 A | 2/1993 | Nappholz et al. |
| 5,209,238 A | 5/1993 | Sundhar |
| 5,213,098 A | 5/1993 | Bennett et al. |
| 5,243,981 A | 9/1993 | Hudrlik |
| 5,285,744 A | 2/1994 | Grantham et al. |
| 5,304,208 A | 4/1994 | Inuaggiato et al. |
| 5,305,745 A | 4/1994 | Zacouto et al. |
| 5,313,020 A | 5/1994 | Sackett |
| 5,318,591 A | 6/1994 | Causey, III et al. |
| 5,391,199 A | 2/1995 | Ben-Haim |
| 5,411,532 A | 5/1995 | Mortazavi |
| 5,411,537 A | 5/1995 | Munshi et al. |
| 5,417,717 A | 5/1995 | Salo et al. |
| 5,419,767 A | 5/1995 | Eggers et al. |
| 5,423,323 A | 6/1995 | Orth |
| 5,433,198 A | 7/1995 | Desai |
| 5,476,485 A | 12/1995 | Weinberg et al. |
| 5,487,752 A | 1/1996 | Salo et al. |
| 5,490,323 A | 2/1996 | Thacker et al. |
| 5,509,411 A | 4/1996 | Littmann et al. |
| 5,535,752 A | 7/1996 | Halperin et al. |
| 5,544,656 A | 8/1996 | Pitsillides et al. |
| 5,549,650 A | 8/1996 | Bornzin et al. |
| 5,563,762 A | 10/1996 | Leung et al. |
| 5,579,234 A | 11/1996 | Wiley et al. |
| 5,579,764 A | 12/1996 | Goldreyer |
| 5,591,142 A | 1/1997 | Van Erp |
| 5,593,430 A | 1/1997 | Renger |
| 5,628,777 A | 5/1997 | Moberg et al. |
| 5,643,330 A | 7/1997 | Holsheimer et al. |
| 5,662,587 A | 9/1997 | Grundfest et al. |
| 5,674,258 A | 10/1997 | Henschel et al. |
| 5,676,153 A | 10/1997 | Smith et al. |
| 5,683,429 A | 11/1997 | Mehra |
| 5,713,937 A | 2/1998 | Nappholz et al. |
| 5,720,768 A | 2/1998 | Verboven-Nelissen |
| 5,743,267 A | 4/1998 | Nikolic et al. |
| 5,751,050 A | 5/1998 | Ishikawa et al. |
| 5,755,759 A | 5/1998 | Cogan |
| 5,788,647 A | 8/1998 | Eggers |
| 5,797,903 A | 8/1998 | Swanson et al. |
| 5,800,460 A | 9/1998 | Powers et al. |
| 5,800,465 A | 9/1998 | Thompson et al. |
| 5,810,735 A | 9/1998 | Halperin et al. |
| 5,814,089 A | 9/1998 | Stokes et al. |
| 5,836,987 A | 11/1998 | Baumann et al. |
| 5,860,964 A | 1/1999 | Willekens et al. |
| 5,873,849 A | 2/1999 | Bernard |
| 5,895,416 A | 4/1999 | Barreras, Sr. et al. |
| 5,902,234 A | 5/1999 | Webb |
| 5,902,248 A | 5/1999 | Millar et al. |
| 5,913,814 A | 6/1999 | Zantos |
| 5,924,997 A | 7/1999 | Campbell |
| 5,935,084 A | 8/1999 | Southworth |
| 5,938,690 A | 8/1999 | Law et al. |
| 5,941,904 A | 8/1999 | Johnston et al. |
| 5,957,957 A | 9/1999 | Sheldon |
| 5,978,710 A | 11/1999 | Prutchi et al. |
| 5,991,661 A | 11/1999 | Park et al. |
| 5,999,848 A | 12/1999 | Gord et al. |
| 5,999,849 A | 12/1999 | Gord et al. |
| 6,002,963 A | 12/1999 | Mouchawar et al. |
| 6,004,269 A | 12/1999 | Crowley et al. |
| 6,009,349 A | 12/1999 | Mouchawar et al. |
| 6,015,386 A | 1/2000 | Kensey et al. |
| 6,024,704 A | 2/2000 | Meador et al. |
| 6,032,699 A | 3/2000 | Cochran et al. |
| 6,033,398 A | 3/2000 | Farley et al. |
| 6,038,480 A | 3/2000 | Hrdlicka et al. |
| 6,044,297 A | 3/2000 | Sheldon et al. |
| 6,044,299 A | 3/2000 | Nilsson |
| 6,052,624 A | 4/2000 | Mann |
| 6,058,329 A | 5/2000 | Salo et al. |
| 6,061,593 A | 5/2000 | Fischell et al. |
| 6,077,136 A | 6/2000 | Arai et al. |
| 6,078,830 A | 6/2000 | Levin et al. |
| 6,081,748 A | 6/2000 | Struble et al. |
| 6,083,216 A | 7/2000 | Fischer et al. |
| 6,115,626 A | 9/2000 | Whayne et al. |
| 6,115,636 A | 9/2000 | Ryan |
| 6,120,442 A | 9/2000 | Hickey |
| 6,141,588 A | 10/2000 | Cox et al. |
| 6,141,593 A | 10/2000 | Patag |
| 6,155,267 A | 12/2000 | Nelson |
| 6,163,716 A | 12/2000 | Edwards et al. |
| 6,163,725 A | 12/2000 | Peckham et al. |
| 6,165,135 A | 12/2000 | Neff |
| 6,171,252 B1 | 1/2001 | Roberts |
| 6,197,021 B1 | 3/2001 | Panescu et al. |
| 6,197,677 B1 | 3/2001 | Lee et al. |
| 6,206,835 B1 | 3/2001 | Spillman, Jr. et al. |
| 6,206,874 B1 | 3/2001 | Ubby et al. |
| 6,214,032 B1 | 4/2001 | Loeb et al. |
| 6,223,080 B1 | 4/2001 | Thompson |
| 6,234,973 B1 | 5/2001 | Meador et al. |
| 6,264,606 B1 | 7/2001 | Ekwall et al. |
| 6,277,078 B1 | 8/2001 | Porat et al. |
| 6,287,256 B1 | 9/2001 | Park et al. |
| 6,289,250 B1 | 9/2001 | Tsuboi et al. |
| 6,299,582 B1 | 10/2001 | Brockway et al. |
| 6,301,500 B1 | 10/2001 | Van Herk et al. |
| 6,309,350 B1 | 10/2001 | VanTassel et al. |
| 6,309,385 B1 | 10/2001 | Simpson |
| 6,328,699 B1 | 12/2001 | Eigler et al. |
| 6,360,123 B1 | 3/2002 | Kimchi et al. |
| 6,363,279 B1 | 3/2002 | Ben-Haim et al. |
| 6,366,811 B1 | 4/2002 | Carlson |
| 6,370,431 B1 | 4/2002 | Stoop et al. |
| 6,406,677 B1 | 6/2002 | Carter et al. |
| 6,418,348 B1 | 7/2002 | Witte |
| 6,421,567 B1 | 7/2002 | Witte |
| 6,438,408 B1 | 8/2002 | Mulligan et al. |
| 6,466,820 B1 | 10/2002 | Juran et al. |
| 6,473,638 B2 | 10/2002 | Ferek-Petric |
| 6,473,653 B1 | 10/2002 | Schallhorn et al. |
| 6,477,395 B2 | 11/2002 | Schulman et al. |
| 6,477,417 B1 | 11/2002 | Levine |
| 6,484,057 B2 | 11/2002 | Ideker et al. |
| 6,484,727 B1 | 11/2002 | Vaska et al. |
| 6,496,730 B1 | 12/2002 | Kleckner et al. |
| 6,580,946 B2 | 6/2003 | Struble |
| 6,584,362 B1 | 6/2003 | Scheiner et al. |
| 6,600,954 B2 | 7/2003 | Cohen et al. |
| 6,611,714 B1 | 8/2003 | Mo |
| 6,625,493 B2 | 9/2003 | Kroll et al. |
| 6,628,989 B1 | 9/2003 | Penner et al. |
| 6,643,546 B2 | 11/2003 | Mathis et al. |
| 6,666,826 B2 | 12/2003 | Salo et al. |
| 6,728,562 B1 | 4/2004 | Budd et al. |
| 6,812,796 B2 | 11/2004 | Pryanishnikov et al. |
| 6,885,889 B2 | 4/2005 | Chinchoy |
| 6,934,584 B1 | 8/2005 | Wong et al. |

| | | |
|---|---|---|
| 6,957,107 B2 | 10/2005 | Rogers et al. |
| 6,978,184 B1 | 12/2005 | Marcus et al. |
| 6,993,384 B2 | 1/2006 | Bradley et al. |
| 6,994,676 B2 | 2/2006 | Mulligan et al. |
| 7,047,084 B2 | 5/2006 | Erickson et al. |
| 7,174,218 B1 | 2/2007 | Kuzma |
| 7,200,437 B1 | 4/2007 | Nabutovsky et al. |
| 7,200,439 B2 | 4/2007 | Zdeblick et al. |
| 7,204,798 B2 | 4/2007 | Zdeblick et al. |
| 7,214,189 B2 | 5/2007 | Zdeblick et al. |
| 7,267,649 B2 | 9/2007 | Zdeblick et al. |
| 7,270,669 B1 | 9/2007 | Sra |
| 7,294,334 B1 | 11/2007 | Michal et al. |
| 7,467,016 B2 | 12/2008 | Colborn |
| 7,591,792 B2 | 9/2009 | Bouton |
| 7,892,675 B1 | 2/2011 | Tsukamoto |
| 2001/0000187 A1 | 4/2001 | Peckham et al. |
| 2001/0002924 A1 | 6/2001 | Tajima |
| 2001/0025192 A1 | 9/2001 | Gerber et al. |
| 2001/0047138 A1 | 11/2001 | Kokate et al. |
| 2001/0053882 A1 | 12/2001 | Haddock et al. |
| 2002/0026183 A1 | 2/2002 | Simpson |
| 2002/0040236 A1 | 4/2002 | Lau et al. |
| 2002/0045921 A1 | 4/2002 | Wolinsky et al. |
| 2002/0077568 A1 | 6/2002 | Haddock |
| 2002/0077673 A1 | 6/2002 | Penner et al. |
| 2002/0095196 A1 | 7/2002 | Linberg |
| 2002/0099419 A1 | 7/2002 | Cohen et al. |
| 2002/0099430 A1 | 7/2002 | Verness |
| 2002/0111560 A1 | 8/2002 | Kokate et al. |
| 2002/0120186 A1 | 8/2002 | Keimel |
| 2002/0151816 A1 | 10/2002 | Rich et al. |
| 2002/0156417 A1 | 10/2002 | Rich et al. |
| 2002/0161307 A1 | 10/2002 | Yu et al. |
| 2002/0169445 A1 | 11/2002 | Jain et al. |
| 2002/0193859 A1 | 12/2002 | Schulman et al. |
| 2003/0036773 A1 | 2/2003 | Whitehurst et al. |
| 2003/0045920 A1 | 3/2003 | Belden et al. |
| 2003/0065364 A1 | 4/2003 | Wellman et al. |
| 2003/0078623 A1 | 4/2003 | Weinberg et al. |
| 2003/0105496 A1 | 6/2003 | Yu et al. |
| 2003/0135248 A1 | 7/2003 | Stypulkowski |
| 2003/0153952 A1 | 8/2003 | Auricchio et al. |
| 2003/0191502 A1 | 10/2003 | Sharma et al. |
| 2003/0204233 A1 | 10/2003 | Laske et al. |
| 2003/0216800 A1 | 11/2003 | Ebert et al. |
| 2004/0000713 A1 | 1/2004 | Yamashita et al. |
| 2004/0024440 A1 | 2/2004 | Cole |
| 2004/0034394 A1 | 2/2004 | Woods et al. |
| 2004/0039417 A1 | 2/2004 | Soykan et al. |
| 2004/0044368 A1 | 3/2004 | Prinzen et al. |
| 2004/0093053 A1 | 5/2004 | Gerber et al. |
| 2004/0097965 A1 | 5/2004 | Gardeski et al. |
| 2004/0098074 A1 | 5/2004 | Erickson et al. |
| 2004/0143154 A1 | 7/2004 | Lau et al. |
| 2004/0161528 A1 | 8/2004 | Martinez et al. |
| 2004/0183209 A1 | 9/2004 | Lin |
| 2004/0193021 A1 | 9/2004 | Zdeblick et al. |
| 2004/0199235 A1 | 10/2004 | Younis |
| 2004/0215049 A1 | 10/2004 | Zdeblick et al. |
| 2004/0220637 A1 | 11/2004 | Zdeblick et al. |
| 2004/0254483 A1 | 12/2004 | Zdeblick et al. |
| 2004/0260346 A1 | 12/2004 | Overall et al. |
| 2005/0027320 A1 | 2/2005 | Nehls et al. |
| 2005/0054892 A1 | 3/2005 | Lau et al. |
| 2005/0075677 A1 | 4/2005 | Ganion et al. |
| 2005/0075683 A1 | 4/2005 | Miesel et al. |
| 2005/0102011 A1 | 5/2005 | Lau et al. |
| 2005/0246004 A1 | 11/2005 | Cameron et al. |
| 2005/0267542 A1 | 12/2005 | David et al. |
| 2006/0035147 A1 | 2/2006 | Lam et al. |
| 2006/0058588 A1 | 3/2006 | Zdeblick |
| 2006/0122678 A1 | 6/2006 | Olsen et al. |
| 2006/0161211 A1 | 7/2006 | Thompson et al. |
| 2006/0170486 A1 | 8/2006 | Tranchina et al. |
| 2006/0247539 A1 | 11/2006 | Schugt et al. |
| 2006/0264775 A1 | 11/2006 | Mills et al. |
| 2006/0265038 A1 | 11/2006 | Hagen et al. |
| 2007/0123944 A1 | 1/2007 | Kanehira |
| 2007/0100399 A1 | 5/2007 | Parramon et al. |
| 2007/0135721 A1 | 6/2007 | Zdeblick |
| 2007/0173896 A1 | 7/2007 | Zdeblick |
| 2007/0179569 A1 | 8/2007 | Zdeblick |
| 2007/0198066 A1 | 8/2007 | Greenberg et al. |
| 2007/0203517 A1 | 8/2007 | Williams et al. |
| 2007/0203537 A1 | 8/2007 | Goetz et al. |
| 2007/0219591 A1 | 9/2007 | Zdeblick et al. |
| 2007/0219608 A1 | 9/2007 | Swoyer et al. |
| 2007/0255336 A1 | 11/2007 | Herbert et al. |
| 2007/0255373 A1 | 11/2007 | Metzler et al. |
| 2007/0255460 A1 | 11/2007 | Lopata |
| 2008/0007186 A1 | 1/2008 | Lu et al. |
| 2008/0021292 A1 | 1/2008 | Stypulkowski |
| 2008/0027289 A1 | 1/2008 | Zdeblick |
| 2008/0039916 A1 | 2/2008 | Colliou et al. |
| 2008/0045826 A1 | 2/2008 | Greenberg et al. |
| 2008/0058656 A1 | 3/2008 | Costello et al. |
| 2008/0061630 A1 | 3/2008 | Andreu et al. |
| 2008/0091246 A1 | 4/2008 | Carey et al. |
| 2008/0097227 A1 | 4/2008 | Zdeblick et al. |
| 2008/0097566 A1 | 4/2008 | Colliou |
| 2008/0114230 A1 | 5/2008 | Addis |
| 2008/0140141 A1 | 6/2008 | Ben-David et al. |
| 2008/0140162 A1 | 6/2008 | Goetz et al. |
| 2008/0140167 A1 | 6/2008 | Hagen et al. |
| 2008/0147168 A1 | 6/2008 | Ransbury et al. |
| 2008/0167702 A1 | 7/2008 | Ransbury et al. |
| 2008/0177343 A1 | 7/2008 | Dal Molin et al. |
| 2008/0200802 A1 | 8/2008 | Bhavaraju et al. |
| 2008/0234588 A1 | 9/2008 | Feldman et al. |
| 2008/0255647 A1 | 10/2008 | Jensen et al. |
| 2008/0294062 A1 | 11/2008 | Rapoport et al. |
| 2008/0294218 A1 | 11/2008 | Savage et al. |
| 2008/0306394 A1 | 12/2008 | Zdeblick et al. |
| 2009/0024184 A1 | 1/2009 | Sun et al. |
| 2009/0054946 A1 | 2/2009 | Sommer et al. |
| 2009/0054947 A1 | 2/2009 | Bourn et al. |
| 2009/0088811 A1 | 4/2009 | Wulfman |
| 2009/0149902 A1 | 6/2009 | Kumar et al. |
| 2009/0299447 A1 | 12/2009 | Jensen et al. |
| 2010/0030294 A1 | 2/2010 | Wong et al. |
| 2010/0204766 A1 | 8/2010 | Zdeblick et al. |
| 2011/0208067 A1 | 8/2011 | Edman et al. |
| 2011/0224578 A1 | 9/2011 | Edman et al. |

FOREIGN PATENT DOCUMENTS

| | | |
|---|---|---|
| EP | 1050265 | 11/2000 |
| EP | 1136033 | 9/2001 |
| EP | 1266606 | 12/2002 |
| EP | 1426079 | 6/2004 |
| JP | 6456031 | 2/1988 |
| JP | 2-99036 | 4/1990 |
| JP | 5269136 | 10/1993 |
| JP | 2000139833 | 5/2000 |
| JP | 2002272758 | 9/2002 |
| WO | WO9912607 | 3/1999 |
| WO | WO9913561 | 3/1999 |
| WO | WO9913574 | 3/1999 |
| WO | WO9952588 | 10/1999 |
| WO | WO0009206 | 2/2000 |
| WO | WO0143821 | 6/2001 |
| WO | WO0195787 | 12/2001 |
| WO | WO02053228 | 7/2002 |
| WO | WO02065894 | 8/2002 |
| WO | WO2004020040 | 3/2004 |
| WO | WO2004052182 | 6/2004 |
| WO | WO2004066814 | 8/2004 |
| WO | WO2004066817 | 8/2004 |
| WO | WO2004066825 | 8/2004 |
| WO | WO2004067081 | 8/2004 |
| WO | WO2005118064 | 12/2005 |
| WO | WO2006029090 | 3/2006 |
| WO | WO2006042039 | 4/2006 |
| WO | WO2006069322 | 6/2006 |
| WO | WO2006069323 | 6/2006 |
| WO | WO2006073915 | 7/2006 |
| WO | WO2006105474 | 10/2006 |
| WO | WO2007005641 | 1/2007 |

| WO | WO2007075974 | 7/2007 |
| WO | WO2007120884 | 10/2007 |
| WO | WO2007149546 | 12/2007 |
| WO | WO2008004010 | 1/2008 |
| WO | WO2008008755 | 1/2008 |
| WO | WO2008027639 | 3/2008 |
| WO | WO2009029894 | 3/2009 |

OTHER PUBLICATIONS

Borky et al., "Integrated Signal Conditioning for Silicon Pressure Sensors" IEEE Transactions on Electron Devices ED-26(12): 1906-1910 (1979).

Kovacs et al., "Technology Development for a Chronic Neutral Interface" A dissertation, Stanford University Aug. 1990 pp. 9, 225-234, 257, 276.

Little et al, "The Output of the Heart and its Control" Physiology of the Heart and Circulation, 4th ed. 1989 Year Book Medical Publishers Inc. pp. 165-187.

Meisel et al., "Transvenous Biventricular Defibrillation", The American Journal of Cardiology, vol. 86 (9A), Nov. 2000 pp. 76K-85K.

Paolocci et al., "Positive inotropic and lusitropic effects of HNO/NO in failing hearts: Independence from β-adrenergic signaling" PNAS vol. 100, No. 9 (2003) 5537-5542.

Receveur et al., "Latteraly Moving Bi-Stable MEMS DC-Switch for Biomedical Applications" Medtronic Bakken Research Center, The Netherlands (2004) pp. 854-856.

U.S. Appl. No. 11/917,992, filed Jul. 13, 2009 (Specification, Claims, Abstract and Figures as filed); Jensen et al., (2009) "Deployable Epicardial Electrode and Sensor Array" 69pp.

U.S. Appl. No. 12/097,959, filed Nov. 17, 2008 (Specification, Claims, Abstract and Figures as filed); Zdeblick et al., (2008) "Implantable Integrated Circuit" 199pp.

U.S. Appl. No. 12/395,538, filed Feb. 27, 2009 (Specification, Claims, Abstract and Figures as filed); Bi et al., (2009) "Integrated Circuit Implementation and Fault Control System, Device, and Method" 163pp.

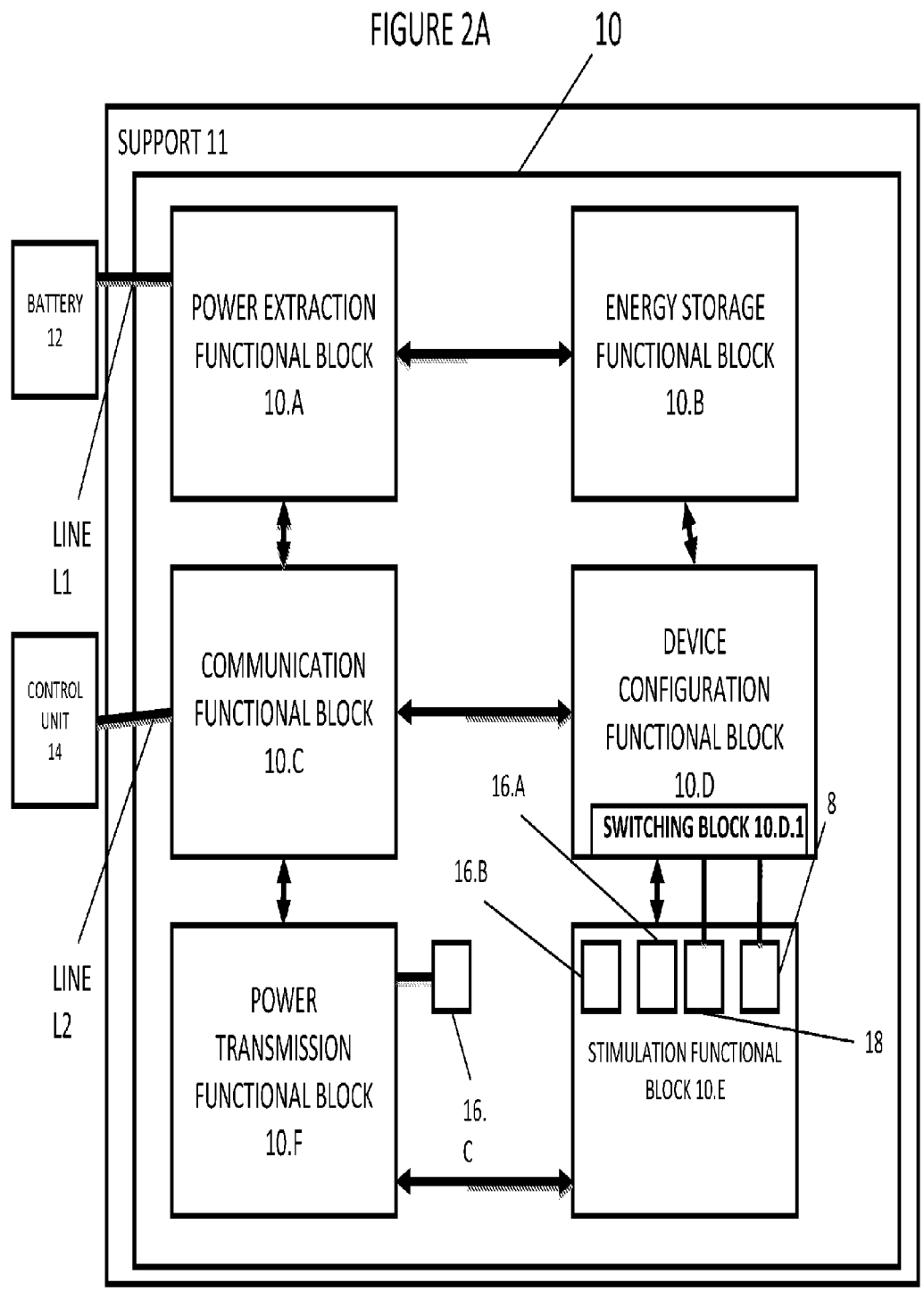

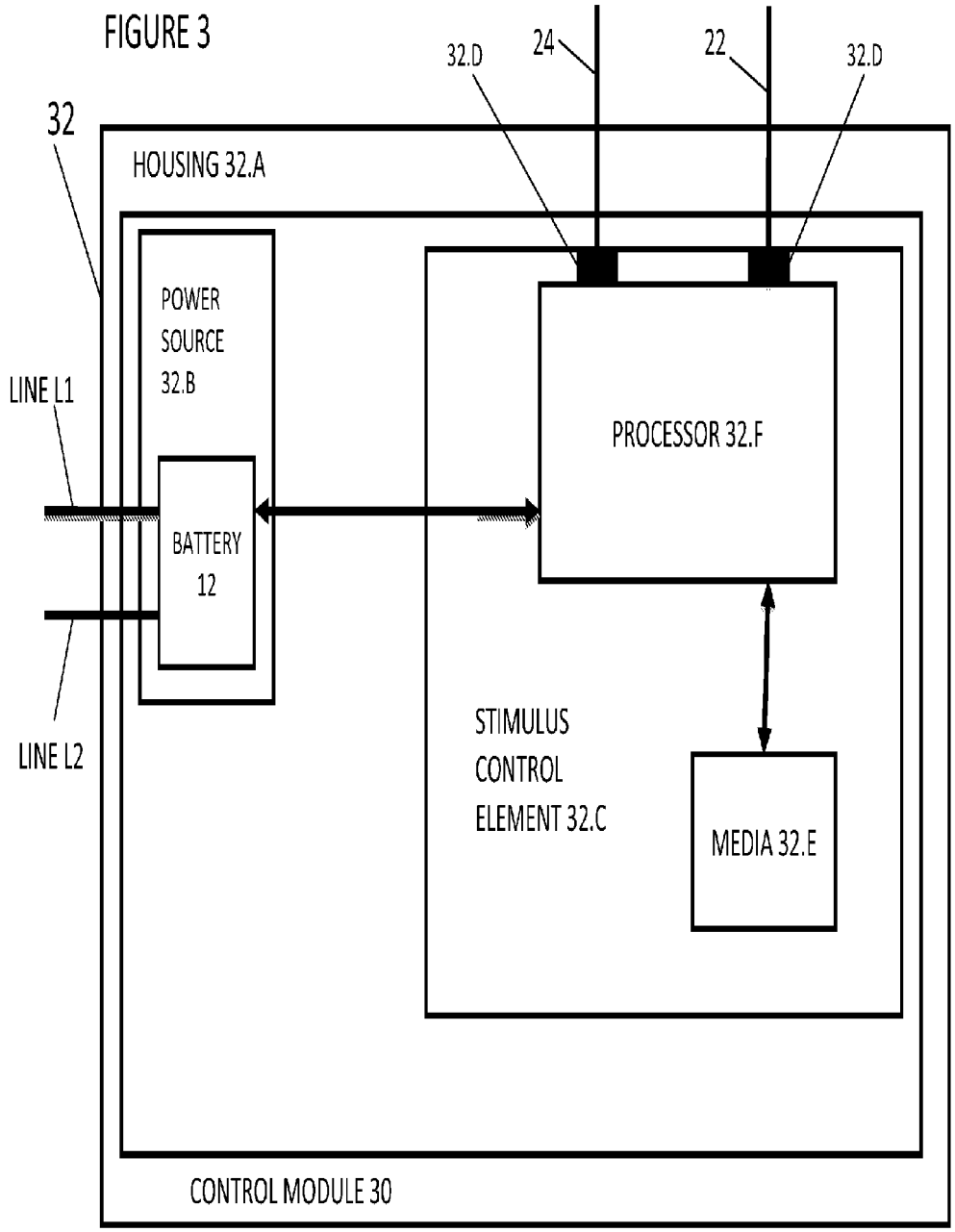

FIGURE 29

| Component | Status |
|---|---|
| Electrode 1 | Complete failure |
| Electrode 2 | 50% signal strength deterioration, degrading at 5% per 28 days |
| Electrode 3 | Normal |
| Electrode 4 | 3 dB noise |
| Satellite 1 | Normal |
| Satellite 2 | Normal |
| Circuit route 1 | Complete Short |
| Circuit route 2 | 10% increase resistance, tending towards an open circuit |
| Lead 1 | Normal |
| Lead 2 | Normal |
| Overall power system | 20% increased power consumption |
| Software and Memory | Normal |

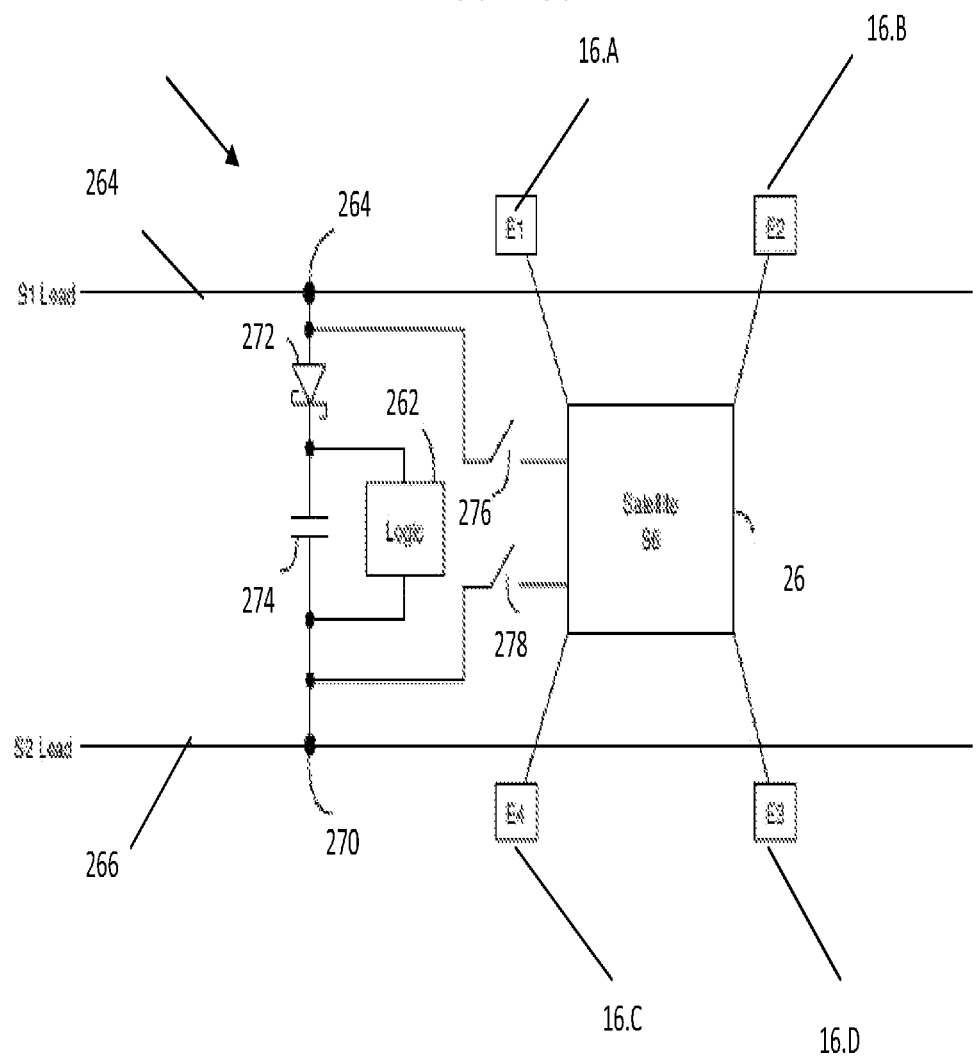

FIGURE 35

Table of Parameter Settings for the Fault Detection Algorithm

| Default Settings | Full scan every 7 days |
|---|---|
| Low-energy setting | Full scan every 28 days |
| Highly specific detection setting | Full scan every day |
| User input setting | Scan all sensors once every ____ days<br>Scan all circuit routes once every ____ days<br>Scan all shocking electrodes once every ____ days |

ND FAULT CONTROL SYSTEM, DEVICE,
INTEGRATED CIRCUIT IMPLEMENTATION AND FAULT CONTROL SYSTEM, DEVICE, AND METHOD

CROSS-REFERENCE TO RELATED APPLICATIONS

Pursuant to 35 U.S.C. §371, this application is a national phase entry of PCT/US2009/035586, the entire disclosure of which is incorporated herein by reference. Additionally, pursuant to 35 U.S.C. §119 (e), this application claims priority to the filing dates of the United States Provisional Patent Application Serial Nos.: 61/032,356 filed Feb. 28, 2008; 61/046,709 filed Apr. 21, 2008; 61/055,097 filed May 21, 2008; and 61/121,128 filed Dec. 9, 2008; which applications are incorporated herein by reference for all purposes.

INTRODUCTION

Implantable devices for administering or monitoring electrical signals, and/or releasing bioactive materials are important tools used in both numerous diagnostic procedures and many medical treatments. Yet the challenges presented by the placement and management of an invasive electrically energized device within a living host being remain significant.

There is, therefore, a long felt need to provide improved systems and methods that support the safe, reliable and effective operation of medical devices as implanted within a living host being.

SUMMARY OF THE INVENTION

Presented are methods, systems and devices for applying therapeutic stimuli or materials by means of a device that may be implanted within a living host being.

One method of the present invention may include a controller configured to provide electrical power to a first electrical lead line, a second lead line, and one or more implantable integrated circuits that are coupled to the first and second lead lines. The first and second lead lines may be switched in polarity during a first mode, and at least one implantable integrated circuit is configured to derive electrical power from the first and second lead lines. The method for controlling a power supply to an implantable device can optionally include the processes of: (a.) receiving a first power signal and a second power signal from the controller; (b.) comparing a voltage level of the first power signal to a voltage level of the second power signal; (c.) setting a first power supply level to a lower voltage level of either the first power signal or the second power signal; and (d.) clamping a second power supply level to a first predetermined differential level when the second power signal exceeds a second predetermined level relative to the first power supply level as set in the previous process of c.

In another aspect of the method of the present invention, a power supply circuit in a satellite integrated circuit of an implantable device may include (1.) a resistor divider network coupled to a first interface signal via a switch; (2.) a transistor coupled to a first power supply, wherein the performance of the transistor is affected by a node of the resistor divider network; and (3.) a buffer configured to both (a.) receive an output from the transistor and (b.) to open the switch when the first interface signal is greater than a first predetermined level.

In an alternate aspect of the method of the present invention, an invented system and method for developing a power supply within a satellite of an electrode lead is provided.

The lead may include both a satellite and a conductor that is electrically connected with a voltage source. The satellite may further include a control electronics and an electrode, wherein the conductor maintains an electrical pathway between the voltage source and the control electronics, and the control electronics is additionally in electrical contact with the electrode. The control electronics may be configured to develop a power supply within the control electronics or the satellite. The control electronics may be responsive in accordance with instructions and signals to alternatively maintain a first impedance and a second impedance between the conductor and the electrode.

In a still alternate optional aspect of the method of the present invention, an invented method and circuitry are provided that reduce the electrical coupling of the implantable device from a host target body. The invented decoupling method may comprise (1.) a transmission and receipt of a decoupling instruction by the implanted device; and (2.) a decoupling function as instantiated by the implanted device in response to receipt of the decoupling signal. It is understood that the terms "to decouple" and "decoupling" are defined herein to mean a reduction in electrical coupling of two objects, e.g., the invented implanted device and a host target body, and that these terms of "to decouple" and "decoupling" are not limited in meaning to an absolute electrical decoupling of the two referenced objects.

In a still alternate optional aspect of the method of the present invention, an invented system and method for fault detection and/or fault recovery are provided. The invented system and method of fault detection and/or fault recovery may take advantage of a redundancy in functional capacity of the invented implantable device to revive the implantable device to effective operation after the occurrence of specific component failures. The fault detection algorithm may enable a component based consideration of (a.) an observed performance deterioration attributable to specific components, (b.) a predictive trend analysis of component deterioration, and/or (c.) a failure probability profile of one or more components of the implantable device. The invented fault recovery system and method may include (a.) reprogramming one or more components of the invented implantable device, (b.) virtual component replacement; and/or (c.) electrical signal normalization of a deteriorating component, and/or (d.) reconfiguration of the implantable device by rerouting of logic signal and sensory signal rerouting and/or component isolation.

It is understood that the terms "pulse" and "waveform" are used synonymously in the present disclosure.

In certain yet alternate aspects of the present invention a computer-readable medium is provided that includes machine-executable software encoded instructions that direct an information technology system to perform one or more aspects of the present invention.

The subject methods and devices find use in a variety of different applications, including cardiac resynchronization therapy, kinesiology, monitoring or exciting of organic tissue, neurological examination and therapy, and gastrointestinal examination and therapy.

The foregoing and other features and advantages will be apparent from the following description of aspects of the present invention as illustrated in the accompanying drawings.

INCORPORATION BY REFERENCE

All publications mentioned herein are incorporated herein by reference to disclose and describe the methods and/or materials in connection with which the publications are cited.

All publications, patents, and patent applications mentioned in this specification are herein incorporated by reference in their entirety and for all purposes to the same extent as if each individual publication, patent, or patent application was specifically and individually indicated to be incorporated by reference.

Such incorporations included the U.S. Pat. No. 7,214,189 (Inventor: Zdeblick, M.) and titled, "Methods And Apparatus For Tissue Activation And Monitoring" issued on May 8, U.S. Pat. No. 7,200,439 (inventors: Savage, G. et al.) and titled, "Method and apparatus for enhancing cardiac pacing" Issued on Apr. 3, 2007; U.S. Pat. No. 6,812,796 (Inventors: Pryanishnikov, et al.) issued on Nov. 2, 2004; U.S. Pat. No. 5,800,460 (Inventors: Powers et al.) titled, "Method for performing self-test in a defibrillator" and issued on Sep. 1, 1998; U.S. Pat. No. 5,751,050 (Inventors: Ishikawa, et al.) issued on May 12, 1998; U.S. Pat. No. 4,600,454 (Inventor: Plummer, W.) issued Jul. 15, 1986; U.S. Pat. No. 4,164,946 (Inventor: Langer, A.) and titled, "Fault detection circuit for permanently implanted cardioverter" issued on Aug. 21, 1979; and U.S. Pat. No. 5,579,234 (Inventor: Wiley, R. et al.) and titled, "System for automatically testing an electronic device during quiescent periods" issued on Nov. 26, 1996.

Such incorporations also included the Patent Cooperation Treaty Patent Application No.s PCT/US2006/048944 titled "Implantable Integrated Circuit" and filed on Dec. 22, 2006; PCT/US2005/031559 titled, "Methods and Apparatus for Tissue Activation and Monitoring," filed on Sep. 1, 2006; PCT/US2005/46811 titled, "Implantable Addressable Segmented Electrodes" filed on Dec. 22, 2005; PCT/US2005/46815 titled, "Implantable Hermetically Sealed Structures" filed on Dec. 22, 2005; PCT/US2007/009270 titled, "Void-Free Implantable Hermetically Sealed Structures" and filed on Apr. 12, 2007; PCT/US2005/031559 titled, "Methods and Apparatus for Tissue Activation and Monitoring," filed on Sep. 1, 2006; PCT/US2006/012246 titled, "AUTOMATED OPTIMIZATION OF MULTI-ELECTRODE PACING FOR CARDIAC RESYNCHRONIZATION" filed on Mar. 31, 2006; PCT/US2005/039535 titled, "Cardiac Motion Characterization by Strain Gauge" by Jensonson, M. et al. filed on Oct. 5, 2006; PCT/US2004/041430 titled, "Implantable Pressure Sensors" filed Dec. 10, 2004; and PCT/US2006/048944 by Zdeblick, M. et al. and titled, "Implantable Integrated Circuit" filed on Jun. 29, 2007.

Such incorporations additionally included US Patent Application Publications Nos. 20040254483 by Zdeblick, M. et al. and titled, "Methods and systems for measuring cardiac parameters" filed on Jan. 1, 2004; 20040220637 by Zdeblick, M. et al. and titled "Method and apparatus for enhancing cardiac pacing" filed Jan. 23, 2004; 20040215049 titled, "Method and system for remote hemodynamic monitoring" by Zdeblick, M. et al. and filed Jan. 23, 2004; and 20040193021 by Zdeblick, M., et al. and titled, "Method and system for monitoring and treating hemodynamic parameters" filed on Dec. 11, 2003.

Such incorporations further included U.S. Nonprovisional patent application Ser. No. 10/734,490 by Zdeblick, M., et al. and titled, "Method and System for Monitoring and Treating Hemodynamic Parameters" filed on Dec. 11, 2003; Ser. No. 10/764,429, by Savage, G., et al. and entitled, "Method and Apparatus for Enhancing Cardiac Pacing," filed Jan. 1, 2004; Ser. No. 11/249,152 entitled, "Implantable Doppler Tomography System," filed Oct. 11, 2005; Ser. No. 11/734,617 by Jensen, M. et al. and titled, "High Phrenic, Low Capture Threshold Pacing Devices and Methods," filed Apr. 12, 2007; Ser. No. 11/324,196 by Thompson T. et al. and titled "Implantable Accelerometer-Based Cardiac Wall Position Detector" filed Dec. 29, 2005; and Ser. No. 11/368,259 by Costello, B. J. and titled: "Fiberoptic Tissue Motion Sensor" filed Mar. 3, 2006.

Such incorporations additionally further included US Provisional Patent Application Nos. 60/617,618 by Savage, G. and titled, "Implantable doppler tomography system"; 60/865,760 by Addis, B. and titled, "Electrode Support" filed on Nov. 14, 2006; 60/791,244 by Zdeblick, M. and titled, "Void-Free Implantable Hermetically Sealed Structures" filed on Apr. 12, 2006; and 60/753,598 by Leichner, et al., and titled, "Fault Recovery for Implantable Device", filed on Dec. 22, 2005.

The publications discussed or mentioned herein are provided solely for their disclosure prior to the filing date of the present application. Nothing herein is to be construed as an admission that the present invention is not entitled to antedate such publication by virtue of prior invention. Furthermore, the dates of publication provided herein may differ from the actual publication dates which may need to be independently confirmed.

BRIEF DESCRIPTION OF THE FIGURES

FIG. 2A is block diagram of a variation of an integrated circuit of the implantable device of FIG. 1;

FIG. 3 is a block diagram of medical device of FIG. 1 and the integrated circuit of FIG. 2A of the implantable device of FIG. 1;

FIG. 29 shows an example of component status profile used by the invented fault recovery and detection process of FIG. 27;

FIG. 30 illustrates an example of possible additional circuitry configured to implement the fault recovery process of FIG. 27;

FIG. 35 is a listing of possible parameter settings useful in the fault recovery process of FIG. 27;

DETAILED DESCRIPTION

Figure 1:
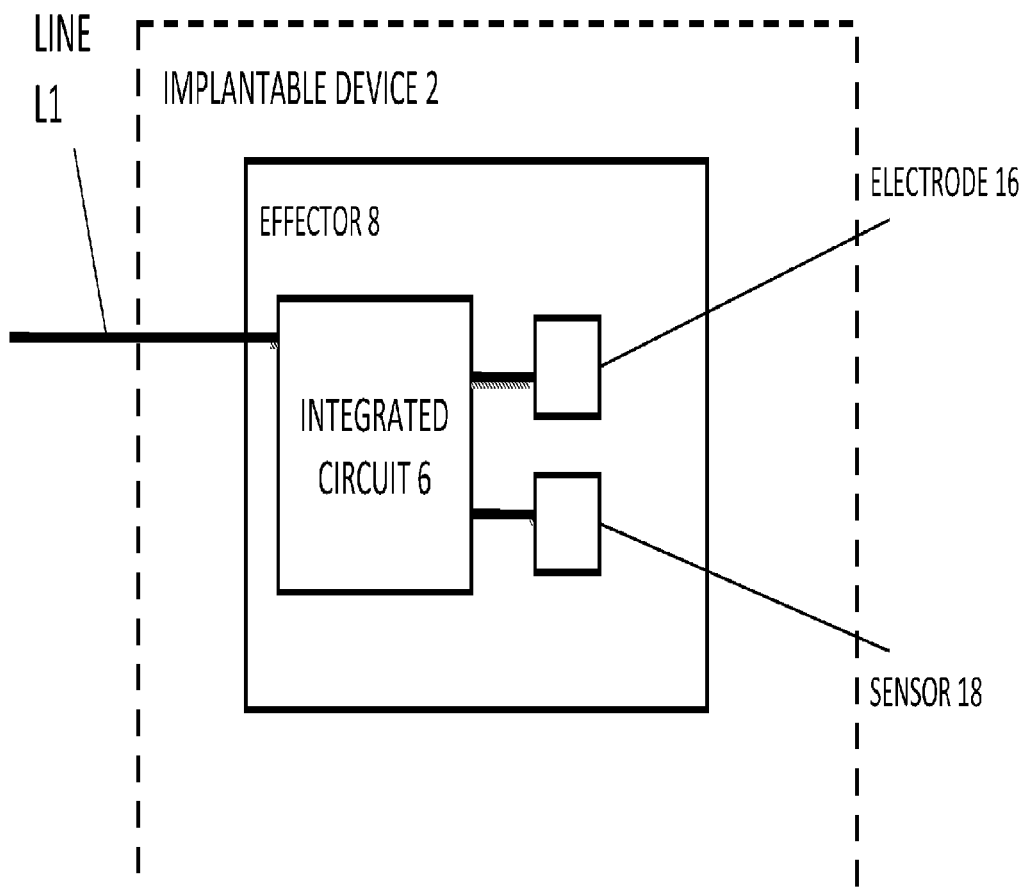
FIG. 1 illustrates a medical device that includes an invented implantable device.

As summarized above, aspects of the present invention enable power supply control that is suitable for an implantable device 2 of FIG. 1 that implement a minimized or basic interface. Such advantages provided by aspects of the present invention enable a variety of different enhanced implantable technologies, such as enhanced implantable pulse generators, e.g., cardiac pacing devices and cardiac monitoring and resuscitation devices.

It is to be understood that this invention is not limited to particular aspects of the present invention described, as such may, of course, vary. It is also to be understood that the terminology used herein is for the purpose of describing particular aspects only, and is not intended to be limiting, since the scope of the present invention will be limited only by the appended claims.

Methods recited herein may be carried out in any order of the recited events which is logically possible, as well as the recited order of events.

For the purposes of the present invention, "body tissue" and "body tissues" refers to all tissue and fluids inside the body, such as heart tissue, lung tissue, liver tissue, brain tissue, muscle tissue, bone, ligament, blood, etc.

For the purposes of the present invention, "external impedance" refers to the impedance of a circuit which is not "internal impedance."

For the purposes of the present invention, "internal impedance" refers to sum of the impedances of power sources (e.g. impedance of batteries, etc.) and wires (e.g. lead lines, etc.).

For the purposes of the present invention, "stable" refers to a condition in which the value of a parameter (e.g. voltage, impedance, power, etc.) does not fluctuate more than 5% from its rated value.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the methods and materials are now described.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The description of the present invention is provided herein in certain instances with reference to a subject or a patient. As used herein, the terms "subject" and "patient" refer to a living entity such as an animal. Aspects of the present invention provide techniques and systems adaptable for use with in evaluating the motion, state or position of an organ or a living tissue of a subject or patient, i.e., a living being. The subject or patient may be an animal, or more particularly a "mammal" or "mammalian," where these terms are used broadly to describe organisms which are within the class mammalia, including the orders carnivore, e.g., dogs and cats, rodentia, e.g., mice, guinea pigs, and rats, lagomorpha, e.g. rabbits and primates, e.g., humans, chimpanzees, and monkeys. In many applications, the subjects or patients will be humans.

Various aspects of the method of the present invention may be applied to living tissue and/or organs of a patient or a subject, such as a heart, a lung, a kidney, a limb, a section of dermis, a hand, a foot, a gut area, a digestive tissue, a bone, cartilage, and/or a muscle. According to a first aspect of the method of the present invention, an electromagnetic pulse may be delivered to living tissue at a cardiac location, such as at or proximate to a heart wall or an element of the diaphragm.

"Evaluating" is used herein to refer to any type of detecting, assessing or analyzing, and may be qualitative or quantitative. The tissue location evaluated in accordance with the various aspects is generally a defined location or portion of a target body, i.e., the body of a subject or a patient, where in many cases it is a defined location or portion, i.e., domain or region, of a target body structure, such as an organ, where in representative applications the target body structure is an internal body structure, such as an internal organ, e.g., heart, kidney, stomach, lung, intestines, and etc.

In many representative alternate applications of the first method, the tissue location is a cardiac location. As such and for ease of further description, the various aspects of the first method are now reviewed in terms of evaluating motion of a cardiac location. The cardiac location may be endocardial, epicardial, or a combination of both, as desired, and may be an atrial location, a ventricular location, or a combination of both. Where the tissue location is a cardiac location, in representative applications of the first method, the cardiac location is a heart wall location, e.g., a chamber wall, such as a ventricular wall, a septal wall, etc. Although the invention is now further described in terms of cardiac motion evaluation applications, the invention is not so limited, the invention being readily adaptable to evaluation of movement of a wide variety of mechanical systems, equipment control systems, robotics, as well as various tissue locations.

Referring now generally to the Figures and particularly to FIG. 1, an invented implantable device 2 of a medical system 4 may include circuitry 6 for transmitting encoded symbols over an electrically conductive single wire L1. One or more assemblies of effectors 8 may optionally be provided that include integrated circuits 6, as well as implantable medical devices, e.g., pulse generators that include the same, as well as systems of using the same, e.g., in bioelectric tissue pacing applications, including cardiac resynchronization therapy ("CRT") applications.

In further describing various configurations of the invention, certain aspects of the inventive integrated circuits 6 will be reviewed first in greater detail, both generally and in terms of the Figures, followed by a discussion of implantable medical devices that may include the subject circuits and systems.

Aspects of the invention provide implantable integrated circuits 6. The term "implantable" as used herein means that a referenced implantable device 2 or a referenced implantable circuit 6 are configured to maintain functionality when present in a physiological environment, including a high salt, high humidity environment found inside of a mammalian or other animal target body, for 2 or more days, such as about 1 week or longer, about 4 weeks or longer, about 6 months or longer, about 1 year or longer, e.g., about 5 years or longer. In certain aspects, the implantable integrated circuits 6 are configured to maintain functionality when implanted at a physiological site for a period ranging from about 1 to about 80 years or longer, such as from about 5 to about 70 years or longer, and including for a period ranging from about 10 to about 50 years or longer.

The dimensions of the implantable medical device 2 may vary. However, because the implantable medical device 2 is implantable, the dimensions of certain aspects of the implantable device 2 are not so big such that the device cannot be positioned in an adult human.

Referring now generally to the Figures and particularly to FIG. 2A, one or more of the implantable integrated circuits 6 may be first single integrated circuit 10 that includes a number of distinct functional blocks 10.A-10.F, e.g., modules 10.A-10.F, where the functional blocks 10.A-10.F are all present in the first single integrated circuit 10 on an intraluminal-sized support 11. The term "single integrated circuit" means a single circuit structure that includes all of the different functional blocks of FIG. 2. As such, the first single integrated circuit 10, (or "first circuit" 10) is a monolithic integrated circuit (also known as "IC", microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain aspects of the present invention are distinct from hybrid integrated circuits, which are miniaturized electronic circuits constructed of individual semiconductor devices, as well as passive components, bonded to a substrate or circuit board.

The support 11 with which the first circuit 10 is associated, e.g., by being present on a surface of the support 11 or integrated, at least partially, inside of the support 11, may be any convenient support, and may be rigid or flexible as desired. As the support 11 is intraluminal sized, its dimensions are such that it can be positioned inside of a physiological lumen, e.g., inside of a vessel, such as a cardiac vessel, e.g., a vein or artery. In certain aspects, the intraluminal-sized integrated circuits have a size (e.g., in terms of surface area of largest surface) of between about 0.05 $mm^2$ and about 5 $mm^2$, such as between about 1.125 $mm^2$ and about 2.5 $mm^2$, and including about 1.5 $mm^2$. The support 11 of the integrated circuits can have a variety of different shapes, such as square, rectangle, oval, and hexagon, irregular, etc.

As indicated above, the implantable circuit 6 and the first circuit 10 of the invention may include a number of functional blocks 10.A-10.F which provide for the requisite functionality of the implantable circuit 6 for its intended use, where the functional blocks 10.A-10.F are all part of the first single integrated circuit 10. In certain aspects, the circuits 6 include at least the following functional blocks: a power extraction functional block 10.A; an energy storage functional block 10.B; a communication functional block 10.C; and a device configuration functional block 10.D.

The power extraction functional block 10.A is a circuitry functional block or module that is configured to extract or obtain power from a power source to which the first circuit 10 is coupled. In the broadest sense, the power extraction functional block 10.A may be a module of electronic circuitry that is configured to receive power from an electrically coupled source, e.g., the first wire L1, or remotely, e.g., power that is wirelessly transmitted to the circuit 10 from a remote location, where that remote location may be an in vivo or ex vivo location, but is one that is not physically connected to the device by a conductive element, such as the first wire L1. In certain aspects, the power extraction functional block 10.A is one that is configured to be coupled to at least one wire S1 that is, in turn, coupled to a power source, such as a battery 12, where the power extraction functional block 10.A extracts power from the wire to power the first circuit 10.

The energy storage functional block 10.B is further comprised within the first circuit 10. The energy storage functional block 10.B is capable of storing energy, e.g., in a capacitive fashion, such as the energy extracted by the power extraction block 10.A. The energy storage functional block 10.B has, in certain aspects, an energy storage capacity of about 200 pF or more, such as about 500 pF or more, including about 800 pF or more, and in certain aspects the storage capacity of the energy storage functional block 10.B is about 5000 pF or less, such as about 2000 pF or less, including about 1000 pF or less. As such, the storage capacity of the energy storage functional block 10.B may, in certain aspects have a total capacity ranging from about 200 to about 5000 pF, such as from about 500 to about 2500 pF, including from about 750 to about 2000 pF. The energy storage functional block 10.B may be made up of a single discreet circuit element or multiple circuit elements, e.g., two or more, three or more, etc., elements each having a capacity ranging from about 60 to about 220 pF, etc.

The implantable circuit 6 and the first circuit 10 of these alternative aspects of the present invention may each further include a communication functional block 10.C. The communications functional block 10.C may comprise electrical circuitry that provides for sending and receiving of data, e.g., in the form of signals, from a location remote to the integrated circuit, be that location in vivo or ex vivo, where the location may be physically connected to the circuit or not. In certain aspects, the communications functional block 10.C is configured to receive command signals from a control unit 14 that is connected to the first circuit 10 and the implantable circuit 6 via at least the first wire L1 and a second wire L2 and/or transmit sensed data signals from the first circuit 10 to a control unit 14 over at least one wire L1 or L2, where the control unit 14 is remote from the circuit and physically connected to the circuit by the at least one wire L1 or L2. In certain aspects, the communication functional block 10.C employs an alternating current at a frequency about 15 kHz or higher, where the operating frequency of the communication functional block may be about 100 kHz or higher, such as about 500 kHz or higher, including about 1 MHz or higher.

The first circuit 10 further includes a device configuration functional block 10.D. This device configuration functional block 10.D is able to employ configuration commands, e.g., as received from a remote device, e.g., the control unit 14, via the communication block 10.C, and configure one or more effectors 8 of the device, e.g., an electrode 16 and 18 according to the received configuration command. In certain aspects, the device configuration functional block 10.D is configured such that the device configuration provided by the functional block of the first circuit 10 is functional without power being applied to the first circuit 10. In certain aspects, the device configuration block 10.D includes a switching block 10.D.1 between the supply terminals and one or more effectors 8. The switching block 10.D.1 may include switching elements each made up of two transistors between each effector 8 and a supply terminal.

In certain aspects, in a given device or system, such as the devices and systems described below, substantially all, if not all of the functions of power extraction, energy storage, communication and device configuration employed by the integrated circuit 6 and 10 during use are provided by the first circuit 10. In yet other aspects, the device or system in which the integrated circuit 6 and 10 is present may provide some of the above functionalities. However, even in such aspects, the circuits may still include the above summarized functional blocks.

In certain aspects, the integrated circuits 6 and 10 are configured to be employed in therapeutic cardiac applications, such as cardiac function monitoring applications and/or therapeutic electrical energy delivery applications, e.g., pacing applications. As such, the circuits may include a stimulation functional block 10.E that enables stimulation of tissue via an effector 8, e.g., electrode 16, that is coupled to the first circuit 10. The integrated circuits 6 and 10 may include a power transmission functional block 10.F that enables low voltage transmission from tissue, e.g., that is contacting an electrode 16 coupled to the first circuit 10. In certain aspects, the first circuit 10 may provide a substantially charge-balanced transmission of a stimulation pulse to tissue, e.g., that is contacting an effector 8 which is coupled to the first circuit 10.

Where desired, the first circuit 10 may include one or more integrated corrosion protection films, e.g., which serve as primary protection of the circuit 10 and functional blocks 10.A-10.F thereof from the implanted environment and impart the implantable functionality to the first circuit 10, e.g., as described above. In certain of these aspects, the integrated corrosion protection films are planar deposited corrosion protection films. In certain aspects, the protection films, i.e., layers, are those described in U.S. Provisional Application Ser. No. 60/791,244 titled "Void-Free Implantable Hermetically Sealed Structures" and filed on Apr. 12, 2006, the disclosure of which is herein incorporated by reference.

These aforementioned features individually or jointly contribute to aspects of the realization of a low power-consumption, intraluminally sized configuration of the implantable device 2 which provide desired functionality in implantable medical devices.

Referring now generally to the Figures and particularly to FIGS. 1, 2 and 3, the integrated circuit 6 and 10 may be characterized by having low power consumption while providing necessary functions for automated actuating or sensing, e.g., from multiple electrodes 16 or sensors 18, which may be coupled to the integrated circuit 6 and 10. Particularly, the modular components of the underlying integrated circuit 6 and 10 and related circuitry consume significantly reduced amounts of power, e.g., as compared to non-integrated circuits that may include similar functionalities, thereby allowing the entire implantable pacing/sensing system with which the integrated circuit 6 and 10 is associated to operate with limited power source, such as may be provided by the battery 12 included in a pacing can 20.

According to one aspect of the method of the present invention, the average power consumption of each invented integrated circuit 6 and 10 may be about 100 µW or less, such as about 100 nW or less, and including about 50 pW or less. The average current draw of the invented integrated circuit 6 and 10 while maintaining its configuration state may be about 1 nA or less, including about 5 pA or less. In addition, the average current draw of the inventive integrated circuit 6 and 10 when the configuration state of the device may be changed in ranges of from about 1 µA to about 100 µA, from about 10 µA to about 50 µA, and including from about 1 µA to about 20 µA.

In another aspect of the method of the present invention, the integrated circuit 6 and 10 is associated with a number of electrodes 16A-16D, e.g., that may be present in a satellite structure of an implantable lead 22, 24 and 25, where multiple satellites 26 each comprise one or more electrodes 16A-16D, and two or more satellites 26 may reside on a single implantable lead 22, 24 and 25. The inventive implantable integrated circuits 6 and 10 facilitate selecting and driving on or more electrodes 16A-16D on such satellites 26 and/or sensing signals through these electrodes 16A-16D. Furthermore, the inventive integrated circuits 6 and 10 facilitate relaying data back from an electrode 16A-16D to the control unit 14, so that the signals detected by the electrodes can be processed and analyzed. In such aspects, the inventive integrated circuits 6 and 10 may also allow a satellite 26 to maintain its configuration state once the satellite 26 and electrodes 16A-16D comprised within the instant satellite 26 are configured. One or more satellites 26 can retain a configuration state while an external power supply 28 is turned off. Hence, the power consumption for the entire implantable signal administration/detection system 2 can be significantly reduced compared with conventional systems.

In practicing certain applications of the method of the present invention, one or more multi-electrode leads 22, 24 and 25 are located relative to a human or a mammalian body, i.e., a "target body". One or more multi-electrode leads 22, 24 and 25 may be implantable such that leads 22, 24 and 25 deliver an electromagnetic energy pulse within the target body, or alternately from locations outside of the target body.

Figure 2B:
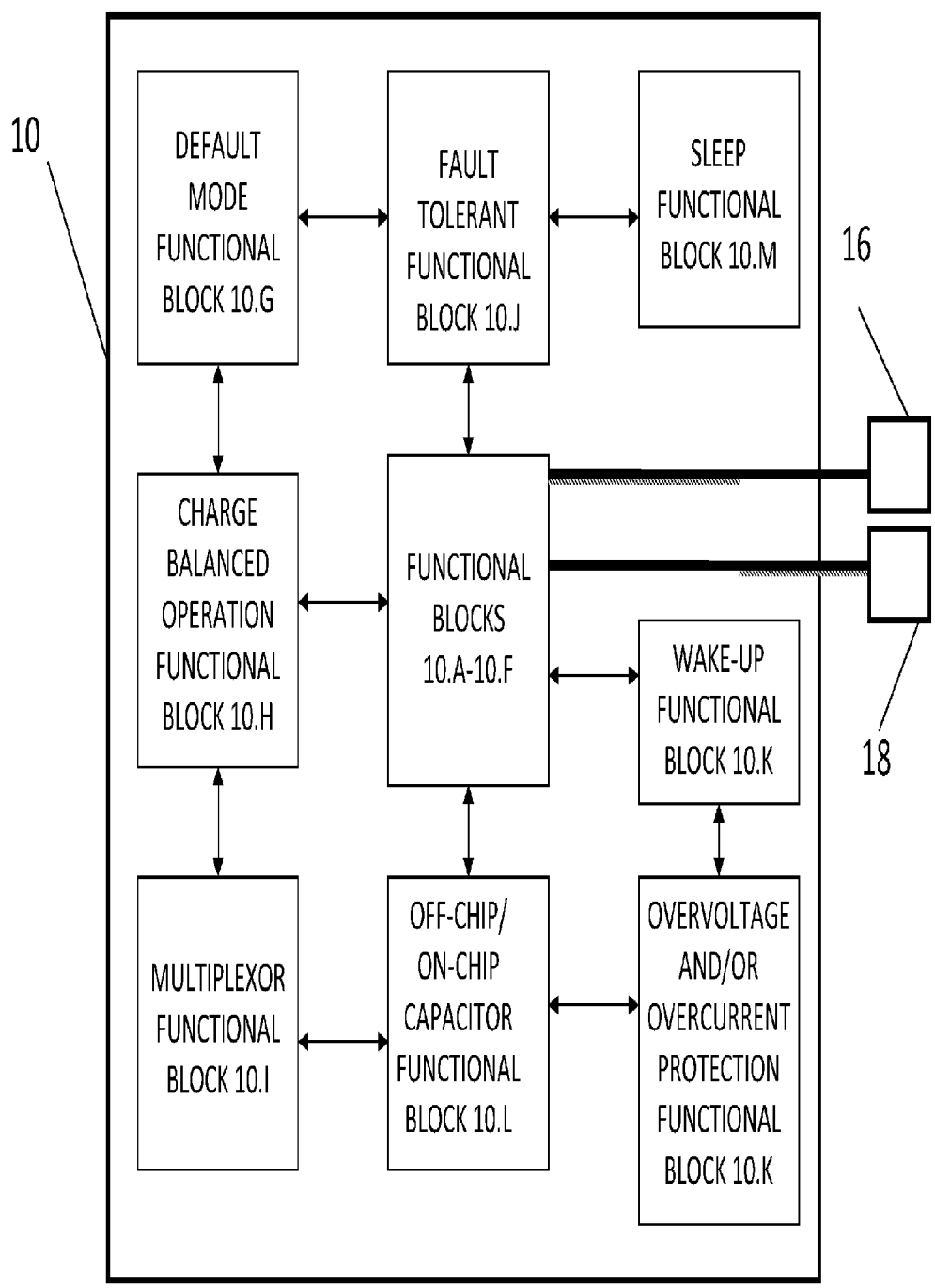
FIG. 2B is a block diagram of further alternate or additional aspects and functionalities of the integrated circuit of FIG. 2A.

Referring now generally to the Figures and particularly to FIG. 2B, FIG. 2B is a block diagram of further alternate or additional aspects and functionalities of the first circuit 10 of FIG. 2A. The integrated circuits 6 and 10 may include a number of additional functionalities imparted to the circuit by one or more additional functional blocks 10.G-10.M. All or just some of the components required for the following functionalities may be integrated into the circuit. As such, a given functional block as described above, is a functional block that, by itself or in conjunction with additional elements not integrated in the circuit, provides for the desired additional functionality. The functional blocks of the first circuit 10 may further include a default mode functional block 10.G, a charge balanced operation functional block 10.H, a multiplexer functional block 10.I, a fault tolerant functional block 10.J, an overvoltage and/or overcurrent protection functional block 10.K, an off-chip or on chip capacitor functional block 10.L, sleep functional block 10.M, and/or a wakeup functional block 10.N. In various aspects, these additional functionalities of the one or more of the additional functional blocks 10.G-10.M may further enable the integrated circuits of the invention to have their intraluminal size and low power consumption and yet provide for desired functionality. Various examples of the above functional blocks are further described in PCT Application Serial No. PCT/US2006/048944 titled "Implantable Integrated Circuit" and filed on Dec. 22, 2006, the disclosure of which is herein incorporated by reference.

In one aspect of the method of the present invention, the implantable device 2 may be employed that includes at least one lead 22, 24 and 25 having multiple programmable satellites 26. Each satellite 26 may comprise at least two electrodes 16.A, 16.B, 16.C and 16.D may be stably associated with a cardiac location of interest, e.g., a heart wall, such as a ventricular wall, septal wall, etc., such that energetic pulse and waveform detections by the sensing element can be correlated with movement of the cardiac location of interest.

Figure 4:
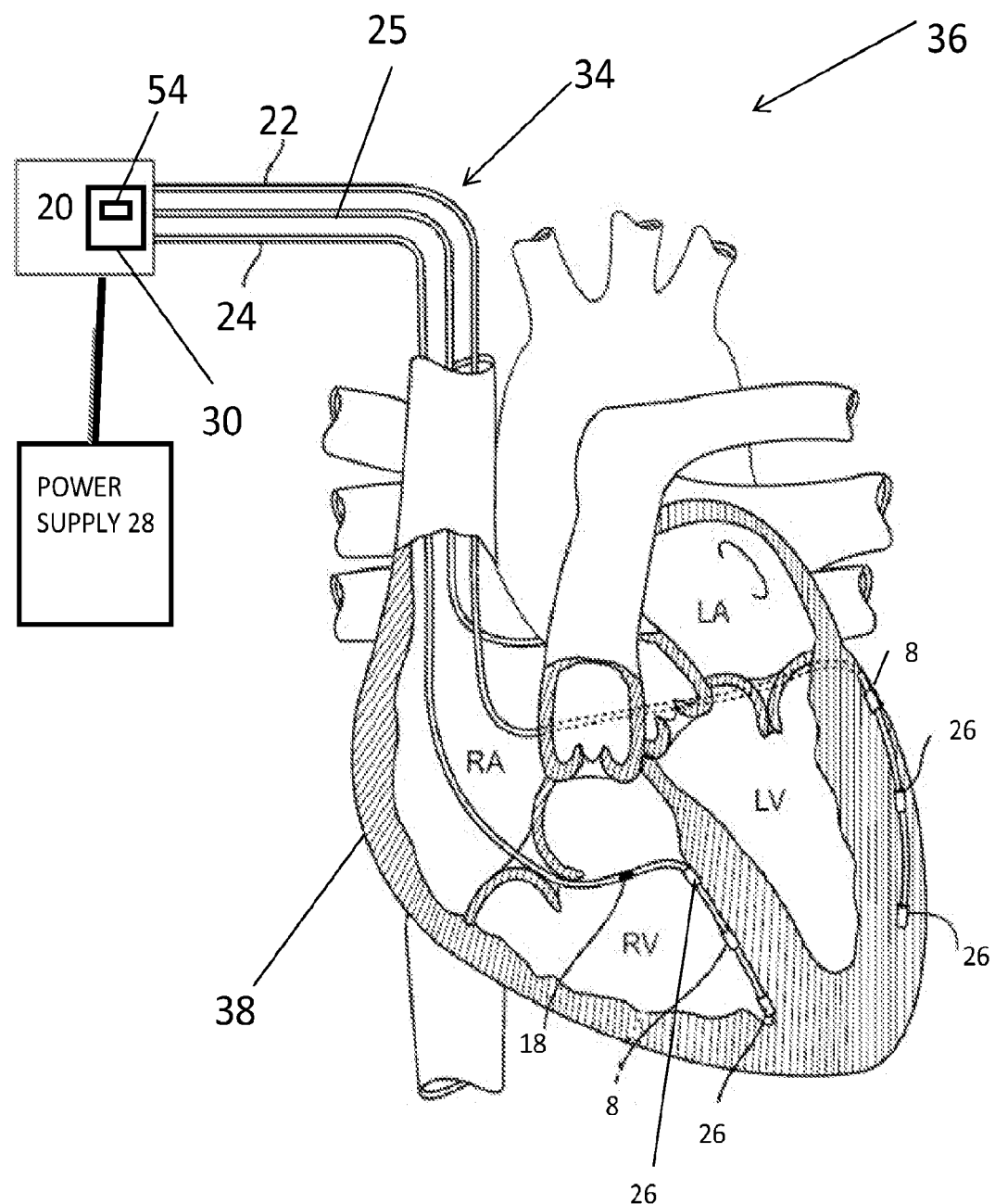
FIG. 4 illustrates the locations of a number of cardiac function pacing satellites, wherein each pacing satellite is separately incorporated within one of a plurality of multi-electrode pacing leads and in accordance with an aspect of the method of the present invention.
Figure 5:
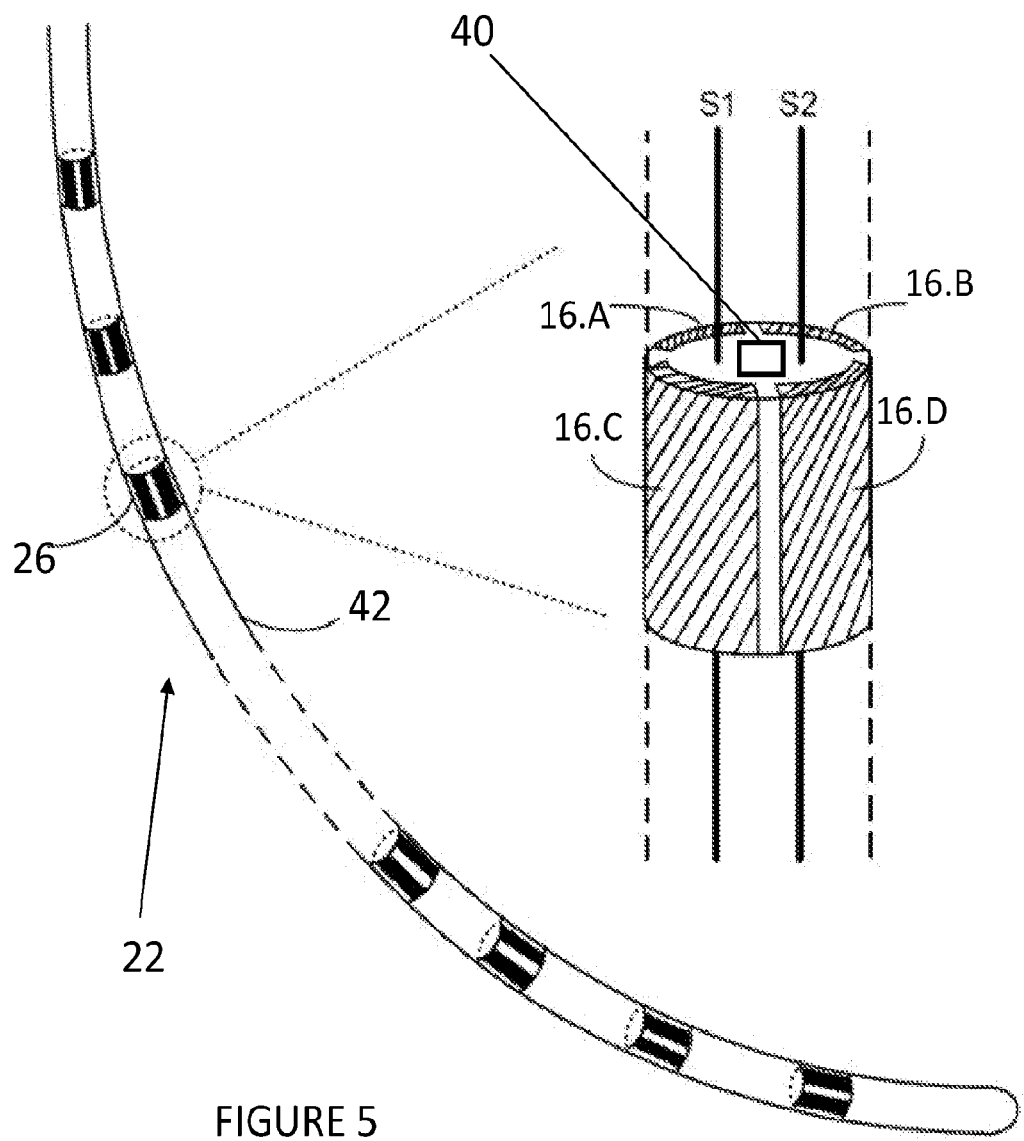
FIG. 5 illustrates an exemplary external view of a plurality of the pacing satellites of FIG. 4 and in accordance with additional aspects of the method of the present invention.

Referring now generally to the Figures and particularly to FIGS. 2, 3, 4 and 5, the integrated circuits 6 and 10 of the method of the present invention find use in a variety of implantable devices 2 and methods of using the same, where such devices 2 include, but are not limited to, cardiac devices, neurological devices, etc. The circuits 6 and 10 find use in implantable devices 2 that include a control module 30, and one or more satellites 26 and sensors 18 distal from the control module 30 where the one or more satellite functionalities are in conductive communication with the control module 30, e.g., via at least one wire L1 and L2 of FIGS. 1, 2 and 3, or via at least a cathode wire S1 or an anode wire S2 as shown in FIG. 5, present in a lead 22, 24 and 25. For description purposes only, the following description of the invention focuses primarily on cardiac aspects of the invention, and particularly implantable pulse generator aspects of the invention. Although the following description frequently uses cardiac pacing as an exemplary application, aspects of the present invention can be applied by a wide range of applications wherein signals are administered to or detected from living tissues. Such applications include, but are not limited to: cardiac pacing and monitoring, neurological stimulation, bone growth stimulation, and drug delivery. It should be noted that integrated circuits of the invention may have one or more functional blocks that enable the following functionalities. However, the following functionalities are not limited to their implementation in the integrated circuits of the device, but could appear in other implantable medical devices and systems that may not include the integrated circuits 6 and 10 as summarized above. These additional medical devices and systems to the extent they include one or more of the following functionalities are specifically within the scope of this invention.

Referring now generally to the Figures and particularly to FIG. 3, certain aspects of the invention provide an invented implantable pulse generator 32. The implantable pulse generator 32 may include: a housing 32.A which includes a power source 32.B and an electrical stimulus control element 32.C; one or more vascular leads 22, 24 or 25 where each lead 22, 24 and 25 is coupled to the control element 32.C in the housing 32.A via a suitable connector 32.D, e.g., an IS-1 connector. The power source 32.B may be a battery 12 that may be provided electrical charge by the electrically conductive lines L1 and L2. In certain aspects, the implantable pulse generator 32 may be employed for cardiovascular applications, e.g., pacing applications, cardiac resynchronization therapy applications, etc. As such, in certain aspects the control element 32.C is configured to operate the pulse generator 32 in a manner such that it operates as a pacemaker, e.g., by having an appropriate control algorithm recorded onto a computer-readable medium 32.E of a processor 32.F of the control element 32.C. In certain aspects the control element 32.C is configured to operate the pulse generator 32 in a manner such that it operates as a cardiac resynchronization therapy device, e.g., by having an appropriate control algorithm recorded onto a computer readable medium 32.E of a processor 32.F of the control element 32.C.

Referring now generally to the Figures and particularly to FIG. 4, FIG. 4 is a schematic illustration of a first alternate pacing and signal detection system 34, or "first device" 34 comprised within a first pacemaker system 36, the first pacemaker system 36 further includes the pacemaker can 20 (hereinafter "pacemaker" 20) and optionally the external power supply 28. FIG. 4 illustrates the locations of the multi-electrode pacing leads 22, 24 and 25 incorporating a number of pacing satellites 26, in accordance with an aspect of the present invention. The pacemaker 20, or pacing and signal detection system 20 may include a control module 30 that provides extra-cardiac communication and control elements for the overall pulse generating pacemaker system 36. In some aspects, pacing and signal detection system 34 may be, for example, a pacing can of a pacemaker 20 residing in an external or extra-corporeal location. The first device 34 includes the multi-electrode pacing leads 22, 24 and 25 incorporating a number of pacing satellites 26

The right ventricular lead 24 emerges from pacing and signal detection system 20 and travels from a subcutaneous location from pacing and signal detection system 20 into the patient's target body (e.g., preferably, a subclavian venous access), and through the superior vena cava into the right atrium of a mammalian heart organ 38, or "heart" 38. From the right atrium, the right ventricle lead 24 is threaded through the tricuspid valve to a location along the walls of the right ventricle. The distal portion of right ventricular lead 24 is preferably located along the intra-ventricular septum, terminating with a fixation in the right ventricular apex. The right ventricular lead 24 includes satellites 26 positioned at locations within the heart 38. The number of satellites 26 in the right ventricular lead 24 is not limited, and may be more or less than the number of satellites 26 shown in FIG. 4.

Similarly, the left ventricular lead 22 emerges from the pacing and signal detection system 20 following substantially the same route as right ventricular lead 24 (e.g., through the subclavian venous access and the superior vena cava into the right atrium). In the right atrium, the left ventricular lead 22 is threaded through the coronary sinus around the posterior wall of the heart in a cardiac vein draining into the coronary sinus. The left ventricular lead 22 is provided laterally along the walls of the left ventricle, which is likely to be an advantageous position for bi-ventricular pacing. FIG. 4 shows satellites 26 positioned at locations along left ventricular lead 22.

The right ventricular lead 24 may optionally be provided with a pressure sensor 18 in the right ventricle. A signal multiplexing arrangement allows a lead 22, 24 and 25 to include such active sensors 18, e.g., pressure sensor, for pacing and signal collection purposes. The pacing and signal detection system 10 communicates with each of the satellites 26. The electrodes 16.A, 16.B, 16.C and 16.D may be controlled by one separate satellite 26 which may also be used to detect cardiac depolarization signals. Additionally, other types of sensors 18, such as an accelerometer, strain gauge, angle gauge, temperature sensor, can be included in any of the leads.

The first device 34, in accordance with additional aspects of the method of the present invention, include device components which can be connected by a multiplex system (e.g., as described in published United States Patent Application publication nos.: 20040254483 titled "Methods and systems for measuring cardiac parameters"; 20040220637 titled "Method and apparatus for enhancing cardiac pacing"; 20040215049 titled "Method and system for remote hemodynamic monitoring"; and 20040193021 titled "Method and system for monitoring and treating hemodynamic parameters; the disclosures of which are herein incorporated by reference), to the proximal end of electrode lead 22, 24 and 25. The proximal end of the electrode lead 22, 24 and 25 connects to a pacemaker 20, e.g., via an IS-1 connector 32.D.

During certain aspects of the method of the present invention, the electrode leads 22, 24 and 25 are each separately placed in the heart 38 using standard cardiac lead placement devices which include introducers, guide catheters, guidewires, and/or stylets. Briefly, an introducer is placed into the clavicle vein. A guide catheter is placed through the introducer and used to locate the coronary sinus in the right atrium. A guidewire is then used to locate a left ventricle cardiac vein. The electrode lead aspect is slid over the guidewire into the left ventricle cardiac vein and tested until an optimal location for CRT is found. Once implanted a multi-electrode lead aspect still allows for continuous readjustments of the optimal electrode location.

The right electrode lead 24 is placed in the right ventricle of the heart 38. In this view, the right electrode lead 24 is provided with one or multiple satellites 26.

The right electrode lead 24 is placed in the heart 38 in a procedure similar to the typical placement procedures for prior art cardiac right ventricle leads. The right electrode lead 24 is placed in the heart 38 using the standard cardiac lead devices which include introducers, guide catheters, guidewires, and/or stylets. The right electrode lead 24 is inserted into the clavicle vein, through the superior vena cava, through the right atrium and down into the right ventricle. The right electrode lead 24 is positioned under fluoroscopy into the location the clinician has determined is clinically optimal and logistically practical for fixating the right electrode lead 24.

Summarizing aspects of the above description, in using the implantable pulse generators of the invention, such methods include implanting an implantable pulse generator 2 e.g., as described above, into a subject; and the implanted pulse generator, e.g., to pace the heart 38 of the subject, to perform cardiac resynchronization therapy in the subject, etc.

During operation, use of the implantable pulse generator 2 may include activating at least one of the electrodes 16.A, 16.B, 16.C and 16.D of the invented pulse generator 2 to deliver electrical energy to the subject, where the activation may be selective, such as where the method includes first determining which of the electrodes 16.A, 16.B, 16.C and 16.D of the pulse generator 2 to activate and then activating the electrode. Methods of using an implantable pulse generator (or "IPG"), e.g., for pacing and CRT, are disclosed in Application Serial Nos.: PCT/US2005/031559 titled "Methods and Apparatus for Tissue Activation and Monitoring," filed on Sep. 1, 2006; PCT/US2005/46811 titled "Implantable Addressable Segmented Electrodes" filed on Dec. 22, 2005; PCT/US2005/46815 titled "Implantable Hermetically Sealed Structures" filed on Dec. 22, 2005; and Ser. No. 11/734,617 titled "High Phrenic, Low Capture Threshold Pacing Devices and Methods," filed Apr. 12, 2006; the disclosures of the various methods of operation of these applications being herein incorporated by reference and applicable for use of the present devices.

Alternate aspects of the method of the present invention further include electrode assemblies, such as electrode satellite structures, where the structures include an integrated circuit control device 6 and 10, e.g., including a circuit of the present invention (described more fully below), and at least one electrode 16.A, 16.B, 16.C and 16.D. As such, the satellite structures include control circuitry, e.g., in the form of an IC (e.g., an IC inside of the support), such that the satellite 26 is addressable. In certain aspects, the structure includes two or more electrodes 16.A, 16.B, 16.C and 16.D, such as three or more electrodes 16.A, 16.B, 16.C and 16.D, including four or more electrodes 16.A, 16.B, 16.C and 16.D, e.g., where the structure is a segmented electrode structure.

As reviewed above, the integrated circuit 6 and 10 may be hermetically sealed or protected. Aspects of hermetically sealed IC chips 6 and 10 include, but are not limited to, those described in PCT application serial PCT/US2005/046815 titled "Implantable Hermetically Sealed Structures" and filed on Dec. 22, 2005; and PCT application serial PCT/US2007/009270 titled "Void-Free Implantable Hermetically Sealed Structures" and filed on Apr. 12, 2007 (PRTS-040WO); the descriptions of hermetically sealed structures provided in these applications being specifically incorporated herein by reference.

As summarized above, the invention provides implantable medical devices 2 that include the electrodes 16.A, 16.B, 16.C and 16.D as described above. The term "implantable medical device" is meant herein as a device that is configured to be positioned on or in a living target body, where in certain aspects the implantable medical device 2 is configured to be implanted in a living target body.

Aspects of the invention also include medical carriers that include one or more electrode satellites 26, e.g., as described above. Carriers of interest include, but are not limited to, vascular lead structures, where such structures are generally dimensioned to be implantable and are fabricated from a physiologically compatible material. With respect to vascular leads, a variety of different vascular lead configurations may be employed, where the vascular lead in certain aspects is an elongated tubular, e.g., cylindrical, structure having a proximal and distal end. The proximal end may include a connector element, e.g., an IS-1 connector, for connecting to a control unit, e.g., present in a "can" or analogous device. The lead may include one or more lumens, e.g., for use with a guidewire, for housing one or more conductive elements, e.g., wires, etc. The distal end may include a variety of different features as desired, e.g., a securing means, etc.

In certain aspects of the subject systems, one or more sets of electrode 16.A, 16.B, 16.C and 16.D or satellites 26 as described above are electrically coupled to at least one elongated conductive member, e.g., an elongated conductive member present in a lead 22, 24 and 25, e.g., the first wire L1, the second wire L2, the cathode wire S1, and/or the anode wire S2. In certain aspects, the elongated conductive member is part of a multiplex lead. Multiplex lead structures may include two or more satellites 26, such as three or more, four or more, five or more, ten or more, fifteen or more, twenty or more, etc. as desired, where in certain aspects multiplex leads have a fewer number of conductive members than satellites 26. In certain aspects, the multiplex leads 22, 24 and 25 include three or less wires L1, L2, S1, and S2, such as only two wires L1, L2, S1, and S2, or only one wire L1, L2, S1, and S2. Multiplex structures of leads 22, 24 and 25 of interest include those described in Application Serial Nos. 10/734,490 titled "Method and System for Monitoring and Treating Hemodynamic Parameters" filed on Dec. 11, 2003; PCT/US2005/031559 titled "Methods and Apparatus for Tissue Activation and Monitoring," filed on Sep. 1, 2006; PCT/US2005/46811 titled "Implantable Addressable Segmented Electrodes" filed on Dec. 22, 2005; PCT/US2005/46815 titled "Implantable Hermetically Sealed Structures" filed on Dec. 22, 2005; and Ser. No. 11/734,617 titled "High Phrenic, Low Pacing Capture Threshold Pacing Devices and Methods" filed Apr. 12, 2007; the disclosures of the various multiplex lead structures of these applications being herein incorporated by reference. In some aspects of the invention, the devices and systems may include onboard logic circuitry or a processor 32.F, e.g., present in a central control unit, such as the pacemaker 20. In these aspects, the central control module 30 may be electrically coupled to the lead by a connector 32.D, such as a proximal end IS-1 connection.

Referring now generally to the Figures and particularly to FIG. 5, FIG. 5 illustrates an external view of a number of exemplary pacing satellites 26, in accordance with a multiplex lead aspect of the present invention. According to one aspect, a pacing lead, e.g., right ventricular lead 24 or left ventricular lead 22 of FIG. 4 accommodates a cathode wire S1 and the anode wire S2, which are coupled to a number, e.g., eight, of satellites 26. FIG. 5 also shows satellite 26 with an enlarged view. Each satellite 26 includes electrodes 16.A, 16.B, 16.C and 16.D located in the four quadrants of the cylindrical outer walls of satellite 26 and supported by an electrode support structure 42 of the invention. Each satellite 26 also contains a satellite controller 40 inside the structure which communicates with the pacemaker 20 to receive configuration signals that determine which of the four electrodes 16.A, 16.B, 16.C and 16.D are to be coupled to the cathode wire S1 and the anode wire S2. The satellite controller 40 may include the first circuit 10. The configuration signals, the subsequent pacing pulse signals, and the analog signals collected by the electrodes 16.A, 16.B, 16.C and 16.D can all be communicated through the cathode wire S1 and the anode wire S2, in either direction. Although shown in a symmetrical arrangement, electrodes 16.A, 16.B, 16.C and 16.D may be offset along a lead 22, 24 and 25 to minimize capacitive coupling among the electrode 16.A, 16.B, 16.C and 16.D. The quadrant arrangement of electrodes 16.A, 16.B, 16.C and 16.D allows administering pacing current via electrodes 16.A, 16.B, 16.C and 16.D oriented at a preferred direction, for example, away from nerves, or facing an electrode configured to sink the pacing current. Such precise pacing allows low-power pacing and minimal tissue damage caused by the pacing signal.

The leads 22, 24 and 25 may further include a variety of different effectors 8 and/or sensors 18, that are distinct from the satellites 26. The effectors 8 and/or sensors 18 may be intended for collecting data, such as but not limited to pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. As such, one or more effectors 8 may be or comprise one or more sensors 18, e.g., temperature sensors, accelerometers, ultrasound transmitters or receivers, voltage sensors, potential sensors, current sensors, etc. Alternatively, the effectors 8 may be intended for actuation or intervention, such as providing an electrical current or voltage, setting an electrical potential, heating a substance or area, inducing a pressure change, releasing or capturing a material or substance, emitting light, emitting sonic or ultrasound energy, emitting radiation and the like.

Effectors 8 of interest include, but are not limited to, those effectors 8 described in the following applications by at least some of the inventors of the present application: U.S. patent application Ser. No. 10/734,490 published as 20040193021 titled: "Method And System For Monitoring And Treating Hemodynamic Parameters"; U.S. patent application Ser. No. 11/219,305 published as 20060058588 titled: "Methods And Apparatus For Tissue Activation And Monitoring"; International Application No. PCT/US2005/046815 titled: "Implantable Addressable Segmented Electrodes"; U.S.

patent application Ser. No. 11/324,196 titled "Implantable Accelerometer-Based Cardiac Wall Position Detector"; U.S. patent application Ser. No. 10/764,429, entitled "Method and Apparatus for Enhancing Cardiac Pacing," U.S. patent application Ser. No. 10/764,127, entitled "Methods and Systems for Measuring Cardiac Parameters," U.S. patent application Ser. No. 10/764,125, entitled "Method and System for Remote Hemodynamic Monitoring"; International Application No. PCT/US2005/046815 titled: "Implantable Hermetically Sealed Structures"; U.S. application Ser. No. 11/368, 259 titled: "Fiberoptic Tissue Motion Sensor"; International Application No. PCT/US2004/041430 titled: "Implantable Pressure Sensors"; U.S. patent application Ser. No. 11/249, 152 entitled "Implantable Doppler Tomography System," and claiming priority to: U.S. Provisional Patent Application No. 60/617,618; International Application Serial No. PCT/USUS05/39535 titled "Cardiac Motion Characterization by Strain Gauge". These applications are incorporated in their entirety by reference herein.

Figure 6:
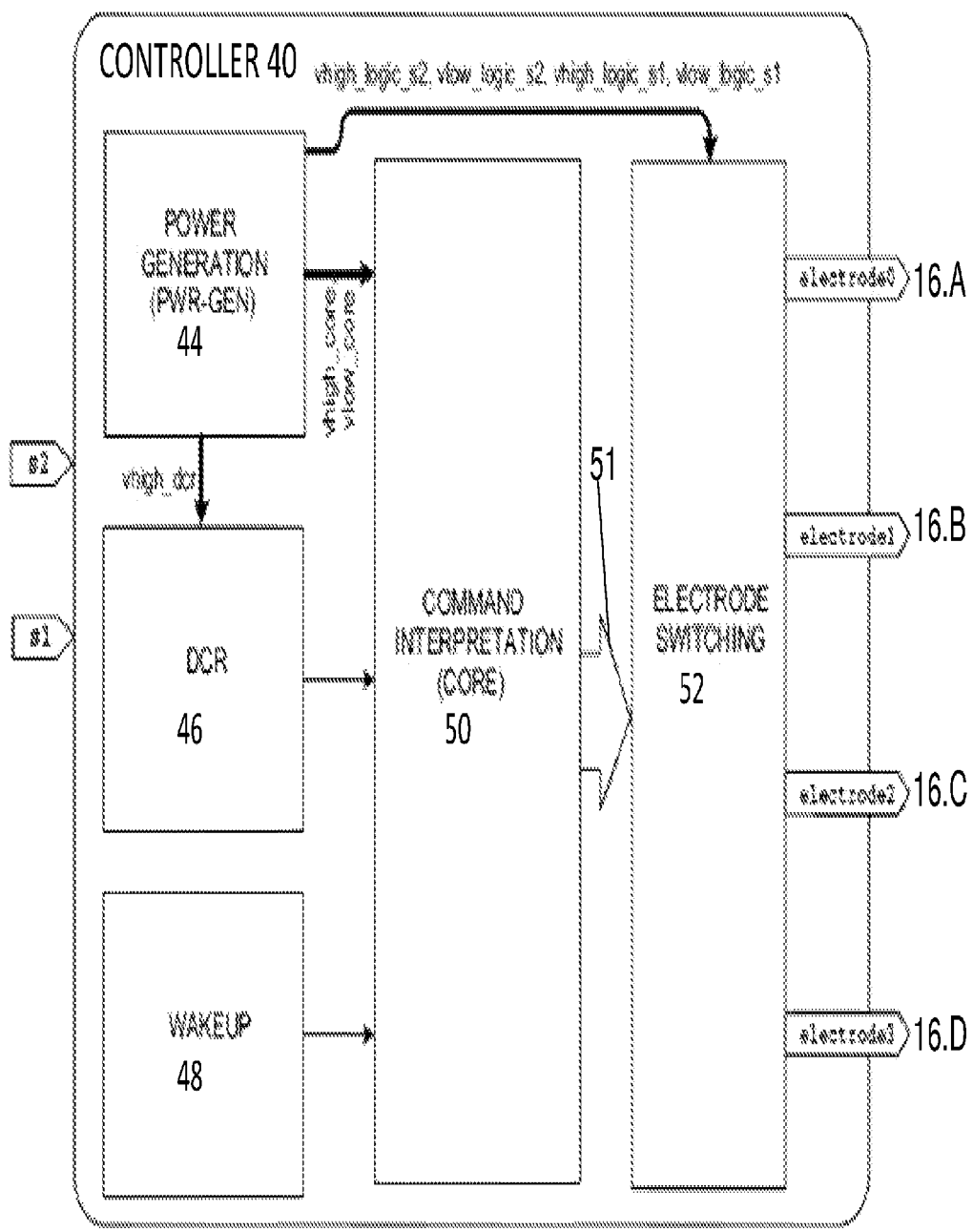
FIG. 6 is a high-level block diagram for a controller within a satellite of a multi-satellite lead of FIGS. 4 and 5 and in accordance with still additional aspects of the method of the present invention.

Referring now generally to the Figures and particularly to FIG. 6, FIG. 6 is a high-level block diagram for a satellite controller 40 of an aspect of the invention that for a satellite 26 that may be present on a multi-satellite lead 22, 24 and 25, in accordance with an aspect of the present invention. The satellite controller 40 includes a power generation (PWR-GEN) module 44 (which is a power extraction module 44), a data-clock recovery (DCR) module 46, a wakeup module 48, a command interpretation module 50 (referred to as the "CORE" module 50 in one aspect), and an electrode-switching module 52 which is coupled to the four electrodes 16.A, 16.B, 16.C and 16.D. The DCR module 46 and the command interpretation module 50 may be the circuitry set forth in international patent publication number WO 2007/075974 or in other patent documents listed above that are incorporated by reference herein.

DCR module 46 provides the correct clock signals recovered from signals, as may be carried on the cathode wire S1 and the anode wire S2 to the rest of digital circuitry within controller 40. DCR module 46 also recovers the data signals carried on the cathode wire S1 and the anode wire S2 into a digital format that can be used by CORE module 50.

Wakeup module 48 generates a wakeup signal to activate and initialize other modules 44-52 after a dormant period during which circuits within controller 40 are turned off to preserve power.

CORE module 50 generates the proper control signals, based on the data received from DCR module 46, to control electrode-switching module 52. Electrode-switching module 52 then selects and switches the electrodes 16.A, 16.B, 16.C and 16.D so that the desired electrodes can couple to the bus lines S1 or S2 for pacing and/or signal-detection purposes.

PWR-GEN module 44 generates the power-supply voltages for CORE module 50, DCR module 46, and electrode-switching module 52. Specifically, PWR-GEN module 44 provides two voltages, vhigh_core and vlow_core, to CORE module 50, and a high voltage, vhigh_dcr, to DCR module 46. Furthermore, PWR-GEN module 44 provides four switch-control signals, vhigh_logic_S2, vlow_logic_s2, vhigh_logic_S1, and vlow_logic_s1, to electrode-switching module 52. These four switch-control signals ensure the electrode-switching circuits to turn on or off sufficiently under large bus line S2-S1 voltage swings incurred during charge-balanced pacing.

Implantable devices 2 and 34 need to operate inside a target body with minimized interfaces, power supplies, and control circuitry. By deriving power from interface lines between implantable devices, the interface and associated overhead is minimized.

In the power supply control system for implantable devices 2 and 34, complementary metal oxide semiconductor (CMOS) integrated circuit (IC) power supplies are derived exclusively from interface signals used for communication between the implantable device 2 and 34 and a controller implantable device, e.g., the pacemaker 20. In particular, implantable device 2 and 34 may be derived from interface bus lead lines, e.g., the cathode wire S1 and the anode wire S2. Further, specialized circuitry is used in the satellite 26 to protect internal circuits from high-voltages on the cathode wire S1 and the anode wire S2 and to prevent latch-up conditions, while accommodating electrode switching.

Figure 7:
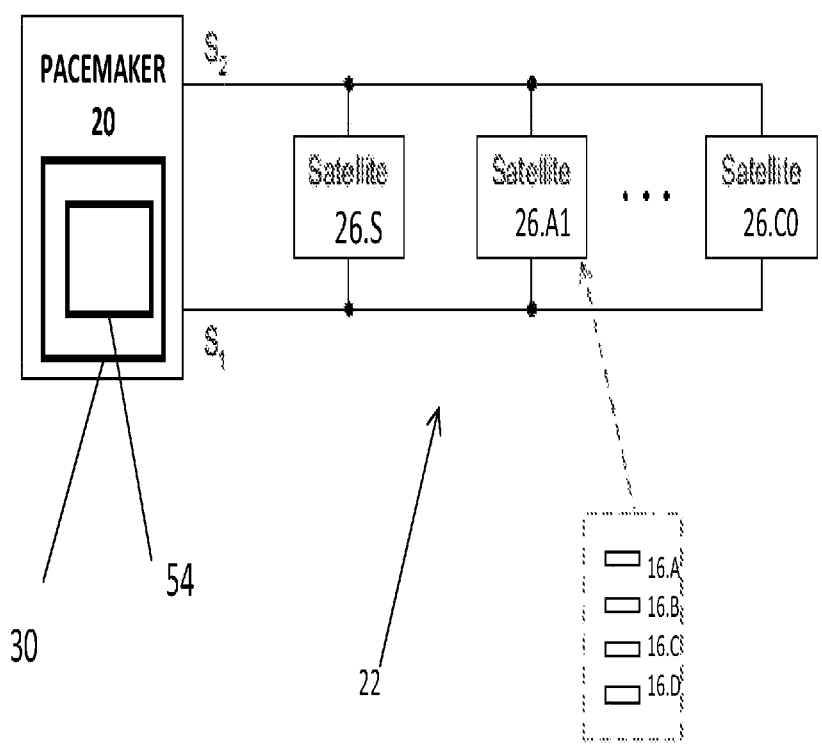
FIG. 7 illustrates an exemplary arrangement of the implantable satellites of FIGS. 4 and 5 and the controller of FIG. 6, wherein the arrangement of FIG. 7 is suitable for power supply generation in accordance with yet additional aspects of the method of the present invention.

Referring now generally to the Figures and particularly to FIG. 4 and FIG. 7, FIG. 7 shows an exemplary implantable satellite 26 and a pacemaker controller 54 of the control module 30 of the pacemaker 20. Implantable devices 2 and 34 suitable for biomedical applications must meet low power, small area, and high voltage tolerance requirements. For pacemaker controllers 54 located remotely from other devices, such as satellites 26 in a pacemaker application, communication to and from the satellite 26 are preferably "minimalistic" in terms of both the physical interface structure, and the operation thereof. In minimizing the physical bus width interface structure, separate or additional power lines cannot be routed between the devices. Accordingly, derivation of power supplies from the interface signals $S_1$ and $S_2$ themselves in implantable satellites 26 is necessary in order to fully minimize the interfaces. Further, the implantable devices 2 and 34 must also support polarity switching of the interface signals for charge balancing purposes.

An interface for communicating from an implantable cardio-defibrillator pacemaker controller circuit 54 to the satellite controller 40 located within a vascular lead electrode satellite 26 employs defined symbols to accommodate data and/or command conveyance. The symbols are typically encoded in the pacemaker controller circuit 54, transmitted via the cathode wire S1 and the anode wire S2 to the satellites 26, and then decoded within by the satellite controllers 40 in order to ascertain the particular communicated bits of information, and thus any associated data or commands. Power for the satellite controller 40 is also derived from the same interconnecting cathode wire S1 and anode wire S2. In addition, commands from the pacemaker controller circuit 54 to the satellite controller 40 can provide switch control for electrodes 16.A, 16.B, 16.C and 16.D, such as by indicating when an electrode 16.A, 16.B, 16.C and 16.D is to be coupled to a particular selection of the cathode wire S1 and the anode wire S2.

Power delivery structures being derived directly from the interconnecting wires of the cathode wire S1 and the anode wire S2 forming an interface between the pacemaker controller circuit 54 and the satellites 26 preferably addresses the needs of reducing area and power. Also, by using CMOS technology for the satellite controller 40, as opposed to other technologies, such as silicon on insulator (SOI), IC ("chip") area is reduced, resulting in lower costs. SOI generally costs more, consumes more chip area, and is not particularly amenable to a variable level substrate connection. However, CMOS technologies are susceptible to latch-up conditions absent appropriate design considerations.

In certain aspects, high voltage protection is achieved with a CMOS process, power supplies are generated from interface signals $S_1$ and $S_2$, e.g., via the cathode wire S1 and the anode wire S2, and such circuitry is also protected from latch-up. Power supply control for implantable CMOS devices is further described herein in terms of: (i) system arrangements and interface, including example circuit blocks in the satellite controller 40; (ii) high voltage protection and power supply circuitry in an implantable CMOS device 2 and 34; and (iii) methods of controlling power supply and electrode switching in an implantable CMOS device 2 and 34.

In the present power generation system for implantable devices, power supplies for a satellite device are derived from interface signals $S_1$ and $S_2$ between the satellite device and a controller. Generally, the interface signals $S_1$ and $S_2$ support encoded data transmissions or predefined symbols that are then demodulated within a satellite 26 for determination of particular conveyed commands (e.g., for electrode switching), data bits, or the like. Further, these same interface signals can be used to derive power supplies for circuitry within the satellite controller 40, as well as to protect from latch-up and high voltage conditions. For example, circuitry using generated power supplies includes electrode switches 52, data clock recovery (DCR) circuitry 46, or any other suitable circuitry.

Referring now generally to the Figures and particularly to FIG. 7, FIG. 7 shows an exemplary implantable satellite 26 and a pacemaker controller 54 of the pacemaker 20. The pacemaker controller 54 includes a processor 32.F and is suitable for power supply derivation in accordance with certain additional aspects of the present invention. The pacemaker controller 54 may be coupled to any number of satellite devices, e.g., satellites 26.S, 26.A1, 26.C0 . . . 26.N via the cathode wire S1 and the anode wire S2. Each satellite 26 may have one or more electrodes 16.A, 16.B, 16.C and 16.D therein, or may be otherwise be coupled to one or more electrodes 16.A, 16.B, 16.C and 16.D While only four electrodes 16.A, 16.B, 16.C and 16.D are shown in this particular example, any suitable number of electrodes 16.A, 16.B, 16.C and 16.D can be accommodated. In addition, each individual satellite 26 can be selected based on a pre-assigned or predetermined address for each satellite 26. For example, an initial satellite 26.S can have a predetermined address of "000," second satellite 26.A1 can have a predetermined address of "001," and so on.

Generally, the pacemaker controller 54 can send an electrical signal that includes a command and an address transmitted along the cathode wire S1 and the anode wire S2, and a selected satellite 26.S. 26.A1, 26.C0 (e.g., based on a match to the address) can respond using the same wires $S_1/S_2$. Further, the commands, addresses, and/or any other suitable data transmitted from pacemaker controller 54 to satellites 26.S, 26.A1, 26.C0 . . . 26.N can include one or more encoded symbols. Among the possible command types are "switch," "clear," "sleep," "default check," "talkback," and "wakeup." When a third satellite 26.C0 is placed in wakeup mode, the cathode wire S1 and the anode wire S2 can be used in certain power supply generation for the satellite device. Further, relatively high voltages on, e.g., the second I lead line S2 during pacing or testing (e.g., when not in wakeup mode) can be clipped within satellite 26.S, 26.A1, 26.C0 . . . 26.N such that internal circuitry will not be damaged. For example, certain aspects determine such a relatively high voltage at lead line $S_2$ (e.g., to generate supply S2_clipped) in a range of from about 3.5 V to 7.5 V, such as from about 4.5 V to 6.5 V, and more specifically about 5.5 V.

Figure 8:
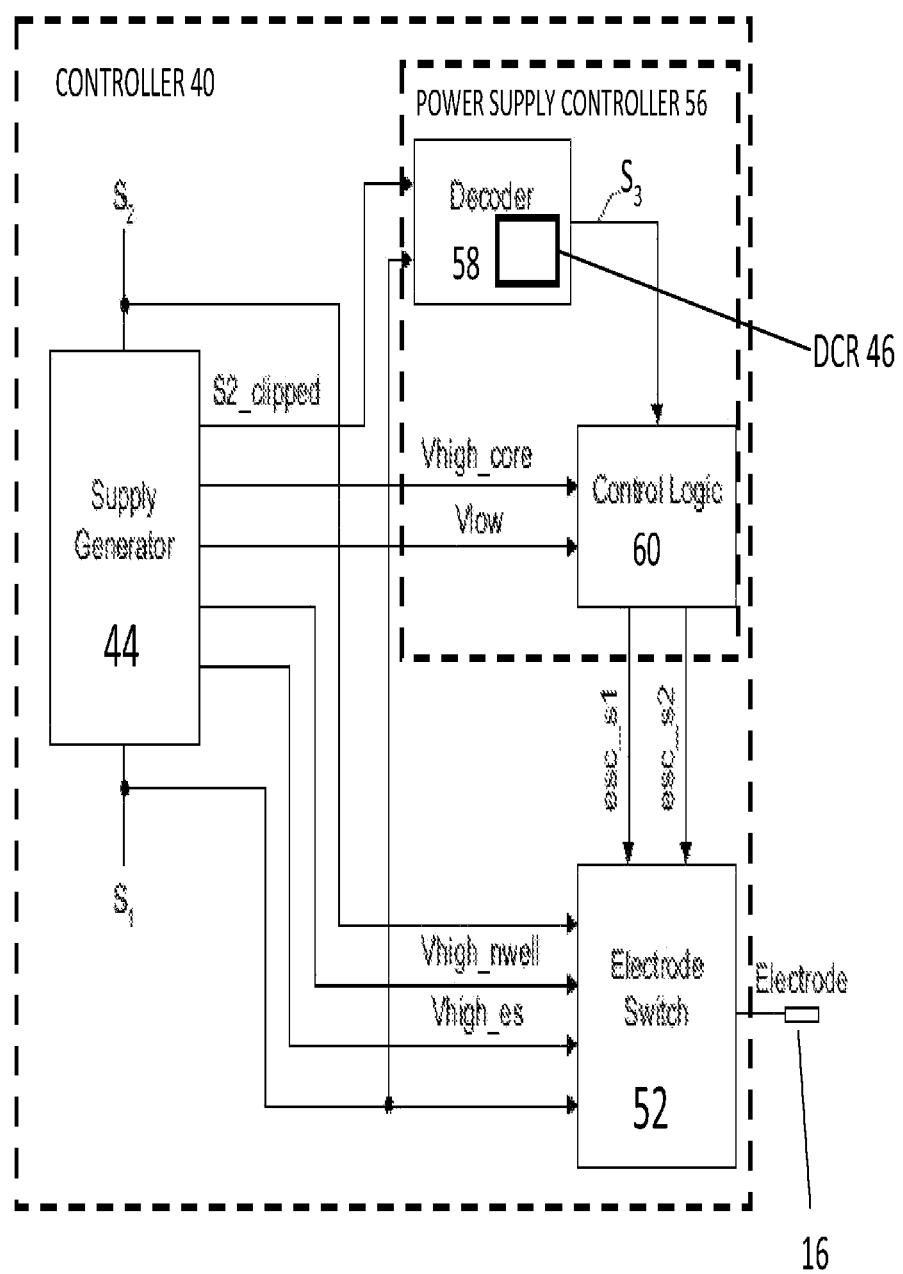
FIG. 8 illustrates an exemplary supply controller in an implantable satellite of FIGS. 4 and 5 in accordance with other additional aspects of the method of the present invention.

Referring now generally to the Figures and particularly to FIG. 8, FIG. 8 shows an exemplary supply controller 56 of the satellite controller 40 of FIG. 6 in an implantable satellite 26.A1, 26.C0 . . . 26.N in accordance with still alternate aspects of the present invention. The power supply generator 44 may be coupled to the lead bus the cathode wire S1 and the anode wire S2. The internal satellite controller 40 may supplies the power signal S2_clipped for the decoder 56, Vhigh_core and Vlow for the control logic 60; and Vhigh_nwell and Vhigh_es for the electrode switch 52, can then be derived from signals $S_1$ and $S_2$ using supply generator 44. Thus, the cathode wire S1 and the anode wire S2 and/or interface signals $S_1$ and $S_2$ can be used to generate various supplies in supply generator 44, where such supplies can be used for power and control logic, etc., and for control of the electrode switch 52.

Figure 9:
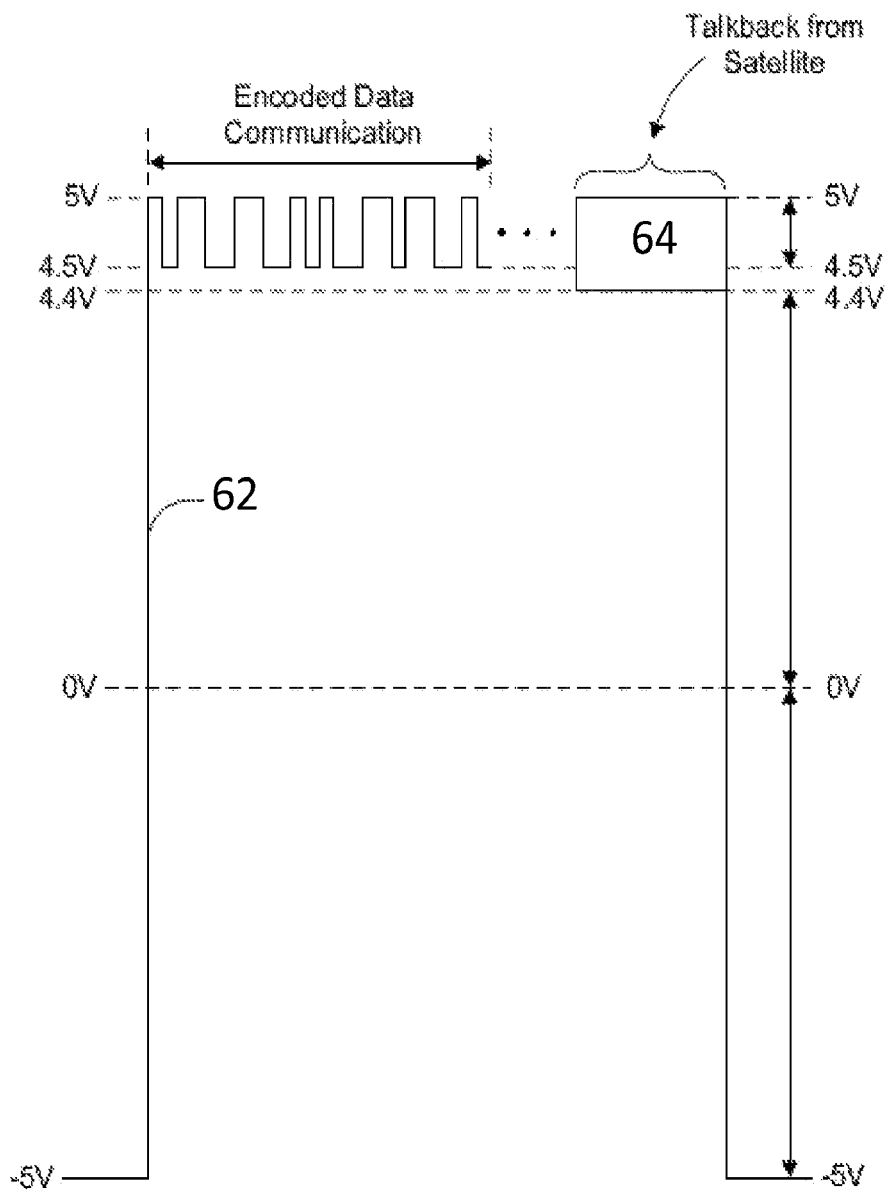
FIG. 9 illustrates a full-swing waveform for an interface signal in accordance with additional aspects of the multi-electrode pacing leads of FIG. 4.

Referring now generally to the Figures and particularly to FIG. 9, FIG. 9 shows a full-swing waveform for an interface signal, e.g., signal $S_1$ or signal $S_2$, in accordance with aspects of the present invention. Waveform 62 can represent interface signal $S_2$ relative to interface signal $S_1$, and may be driven by either a satellite controller 40 or by the pacemaker controller 54. In certain aspects, encoded data communication (e.g., via predetermined symbols), as well as communication during talkback period 64, can be accomplished using a relatively small swing voltage variation over a larger voltage level. For example, waveform 62 can range from about −5 V to about 4.5 V, and then between about 4.5 V and about 5 V to support data encoding from the controller to the satellite, as well as charge balancing on the interface signal (e.g., $S_2$) itself. However, the talkback period 64 can involve a voltage range from about 100 mV below an amplitude of about 4.5 V, thus more specifically from about 4.4 V to about 5 V for return data bit communication. However, any suitable amplitude variation can be used for talkback mode communication. For example, certain aspects use amplitude variation for talkback mode in a range of from about 400 mV to 800 mV, such as from about 500 mV to 700 mV, and more specifically about 600 mV.

Using interface signals $S_1$ and $S_2$, power supplies S2_clipped, Vhigh_core, Vlow, Vhigh_nwell, and Vhigh_es, can be derived. S2_clipped can be used for decoding, e.g., via a DCR circuit 46 in decoder 58), encoded data communication to provide signal $S_3$ (e.g., a binary string of bits, or plurality of control signals) to control logic 60. For example, certain aspects utilize voltages for supply level S2_clipped in a range of from about 3 V to 7 V, such as from about 4 V to 6 V, including from about 4.5 V to 5.5 V, and more specifically about 5 V. Supply S2_clipped can provide high voltage protection for a satellite device 26 when the pacing or controller device 20 is driven at supplies greater than about 5.5 V.

Control logic 60 can receive supplies Vhigh_core and Vlow from supply generator 44. For example, certain aspects use voltages for supply Vhigh_core in a range of from about 3 V to 7 V, such as from about 4 V to 6 V, including from about 4.5 V to 5.5 V, and more specifically about 5 V. Supply Vlow is used for substrate connection on the satellite controller 40, e.g., in a CMOS technology implementation, and may generally have any voltage level equal to about a lower of signal $S_1$ or signal $S_2$, and may be as low as about −5 V. Electrode switch 52 can receive supplies Vhigh_nwell and Vhigh_es from supply generator 44 for latch-up prevention in switching the electrode 16.A, 16.B, 16.C and 16.D to one of lead lines $S_1$ or $S_2$.

Figure 10:
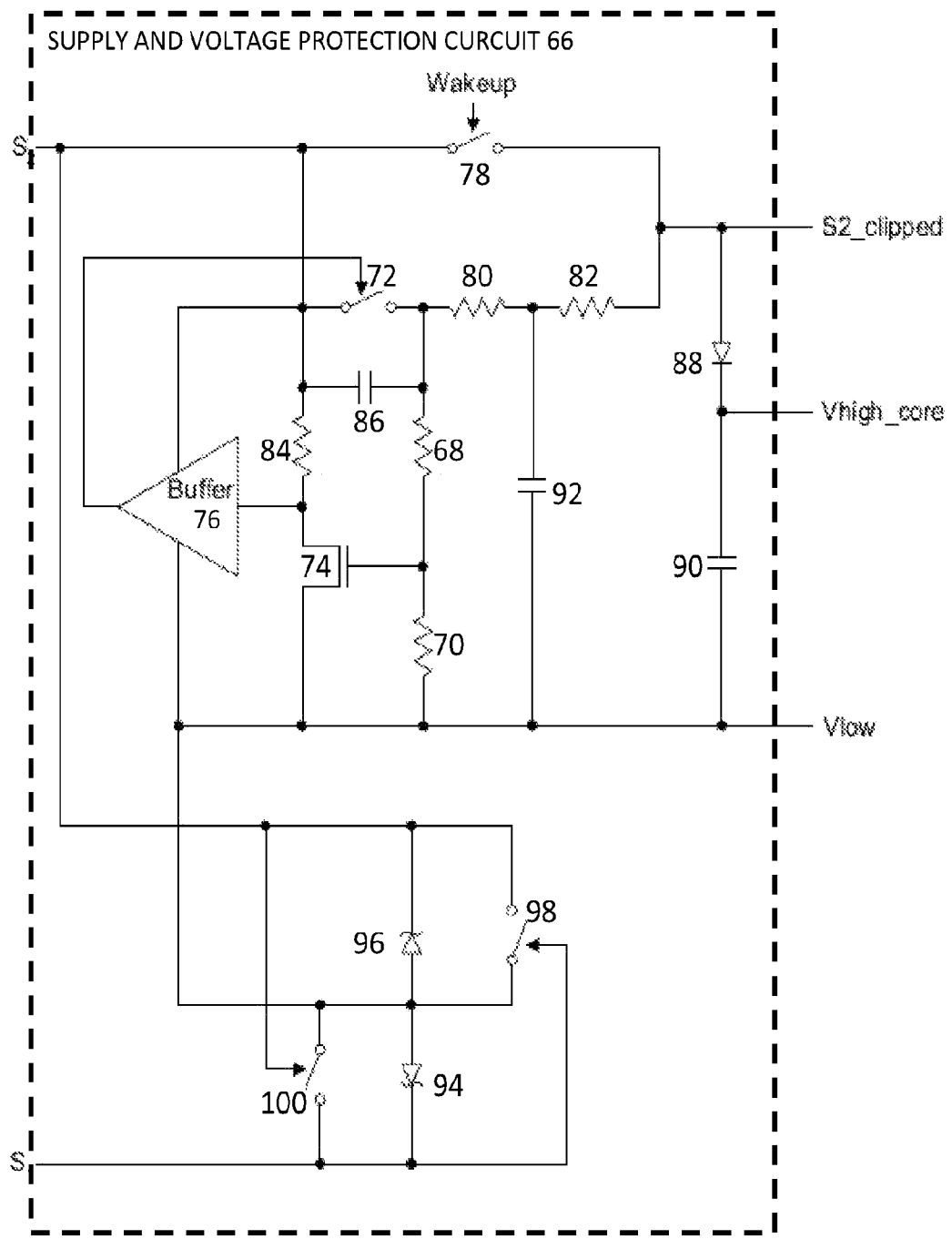
FIG. 10 illustrates a first exemplary supply generator circuit portion in accordance with still additional aspects of the multi-electrode pacing leads of FIG. 4.
Figure 11:
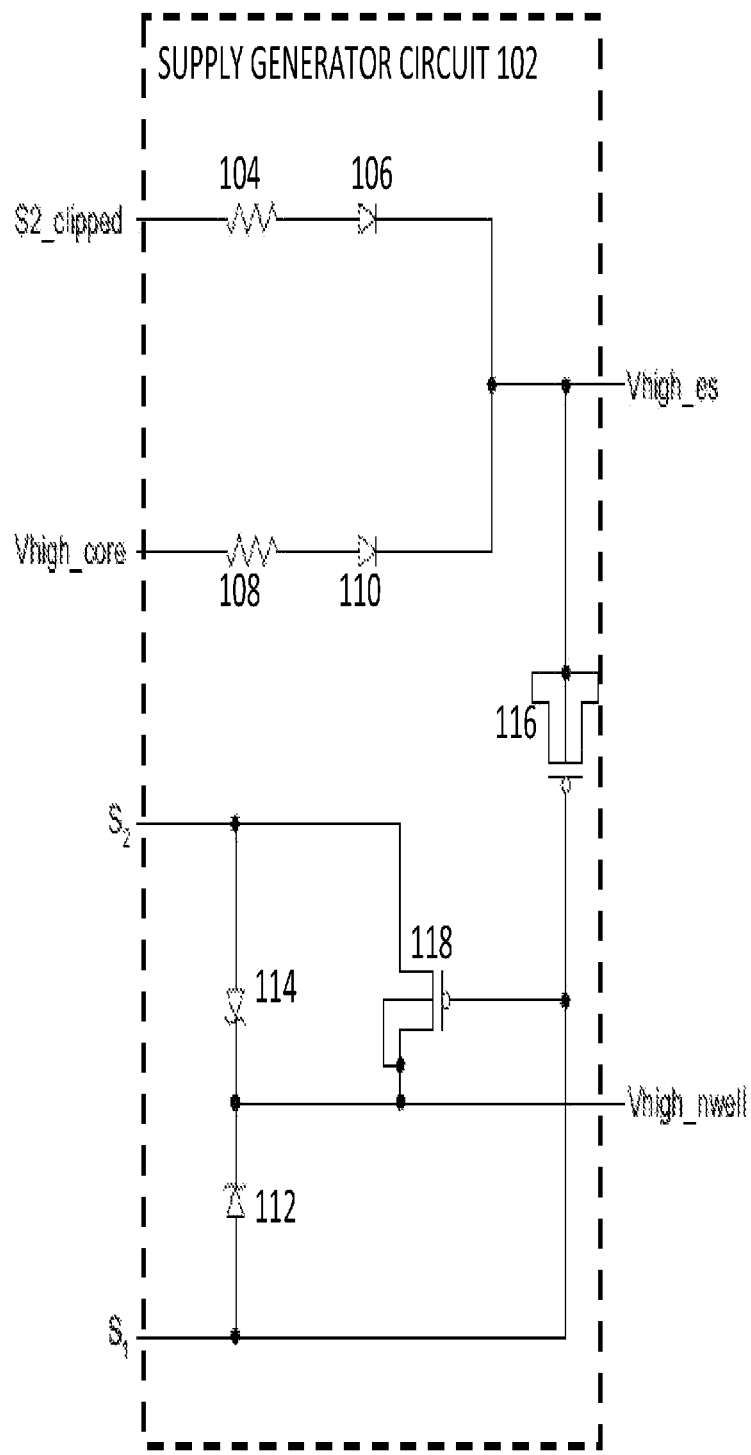
FIG. 11 illustrates a second exemplary supply generator circuit portion in accordance with yet additional aspects of the multi-electrode pacing leads of FIG. 4.
Figure 12:
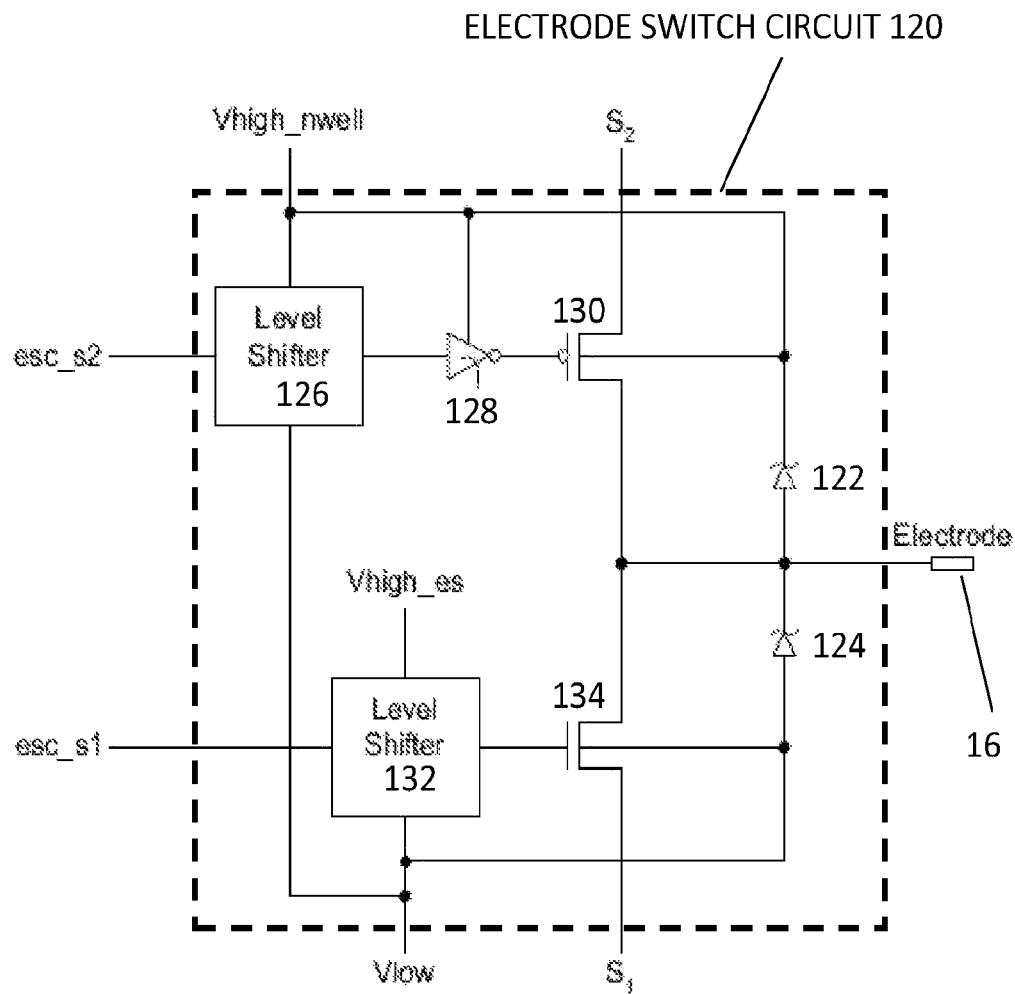
FIG. 12 illustrates an exemplary electrode switch circuit portion in accordance with other aspects of the multi-electrode pacing leads of FIG. 4.

Referring now generally to the Figures and particularly to FIGS. 10, 11 and 12, circuits implementing yet additional aspects of the method of the present invention provide a supply generation and high voltage protection circuit 66 for implantable devices with minimized interfaces, with low IC area requirements, and with latch-up protection, are shown in FIGS. 10, 11 and 12. In particular, FIGS. 10 and 11 show supply generator circuit portions, and FIG. 12 shows electrode switch circuit portions.

Referring now generally to the Figures and particularly to FIG. 10, FIG. 10 shows an exemplary supply generator and voltage protection circuit 66 of the satellite controller 40 and for supplies S2_clipped, Vhigh_core, and Vlow. During pacing, interface signals (e.g., $S_2$) may be raised above about 5.5 V (e.g., to about 10 V, or higher), but output signal S2_clipped can remain less than about 5 V. For example, certain aspects use inducing S2_clipped circuitry in a range of from about 5 V to 12 V, such as from about 5.5 V to 8 V, and more specifically about 6 V. Such high voltage is detected on signal $S_2$ using a resister divider network including resistors 68 and 70 when switch 72 is closed. This high voltage detection results in transistor 74 being turned on, which then closes switch 72 via a buffer control 76. During "signaling" operation (e.g., encoded data transmission from the controller to a satellite device, or return transmission in talkback mode), wakeup signal control closes switch 706 to allow S2_clipped to be substantially equal to interface signal $S_2$.

Thus, switch 78 is normally open during high voltage pacing or testing using signal $S_2$. Further, a delay path between signal S2_clipped and buffer 76 is formed with resistors 80, 82, and 84, as well as capacitor 86, such that buffer 76 transitioning does not substantially affect signal S2_clipped during signaling operation (e.g., when a voltage of lead line $S_2$ is less than about 6 V). When high voltage protection is needed, both of switches 78 and 72 should be open. Thus, signal S2_clipped is supported by a diode 88, and a first capacitor 90. A second capacitor 92 is also used to support signal S2_clipped, as well as to provide signal path delay back to the gate of transistor 74. Further, switch 72 may be implemented as PMOS and NMOS transistors in parallel, and several stages of inversion can form buffer 76.

Signal Vhigh_core is used primarily as the power supply for control logic 60, but the supply can also be used to power other digital logic or circuitry. The first capacitor 90 can be formed using NMOS transistor and other standard capacitor portions (e.g., user programmable or alterable portions), to provide an appropriate level of capacitance on signal Vhigh_core. For example, the first capacitor 90 has any capacitance value in a range of from about 0.2 nF to 2 nF, such as from about 0.5 nF to 1.5 nF, including from about 0.8 nF to 1.2 nF, and more specifically about 1 nF. Of course, higher or lower capacitance values for the first capacitor 90 can be used depending on the particular current and/or switching load on signal Vhigh_core.

Supply Vlow is used to bias the substrate of the satellite CMOS IC for latch-up prevention, given possible polarity variation in the cathode wire S1 and the anode wire S2, e.g., the waveforms 62 and 64 of FIG. 9. Thus, generated supply Vlow is used instead of a dedicated ground line or strict "0 V" level in order to save interface signal width, and also to allow for reversal of interface signals $S_1$ and $S_2$ during pacing. To accomplish this, particular aspects utilize Schottky diodes and switches to generate Vlow from the cathode wire S1 and the anode wire S2.

Generally, Schottky diodes switch faster than regular diodes due to having lower threshold voltages. For example, a Schottky diode may have any threshold value in a range of from about 150 mV to 350 mV, such as from about 200 mV to 300 mV, and more specifically about 250 mV. For example, a regular diode may have any threshold value in a range of from about 600 mV to 800 mV, such as from about 650 mV to 750 mV, and more specifically about 700 mV. Using Schottky diodes 94 and 96, Vlow may not be allowed to go higher than a Schottky diode threshold above the lowest voltage of $S_1$ or $S_2$.

The level of Vlow can be further reduced using switches 98 and 100 to essentially determine which of $S_1$ or $S_2$ has the higher voltage. For example, Vlow reaches about −5 V when $S_2$ equals about 0 V and $S_1$ equals about −5 V. Thus, Vlow can be substantially equated with a lower of the voltages of signals $S_1$ and $S_2$. In this fashion, an effective "ground" level can be derived from interface signals $S_1$ and $S_2$ that can vary in polarity with respect to each other. Despite this, Vhigh_core-Vlow may be held to less than about 5.5V in order to provide high voltage protection for the core logic (e.g., control logic 60). This "ground" level for Vlow can effectively bias the substrate in an n-well (p-substrate) CMOS process used for the satellite IC 40.

Referring now generally to the Figures and particularly to FIG. 11, FIG. 11 shows an exemplary supply generator circuit 102 of the power generation circuit 44 of FIG. 6 for supplies Vhigh_es and Vhigh_nwell. Supply Vhigh_es, which is used in the electrode switch 52, may be derived from supplies S2_clipped and/or Vhigh_core. As shown, a first resister 104 and first diode 106 can be used to sustain supply Vhigh_es at a level of about a diode threshold drop below the voltage of supply S2_clipped. Similarly, second resister 108 and second diode 110 can be used to sustain supply Vhigh_es to within about a diode drop from supply Vhigh_core. Resistors 104 and 108 can also be used in preventing latch-up or other high current issues caused by the parasitic bipolar PNP transistor being turned on at diodes 106 and 110, respectively. Supply Vhigh_nwell, used primarily for latch-up protection in the electrode switch 52, is also not allowed to go below a Schottky diode threshold from the cathode wire S1 and the anode wire S2 via Schottky diodes 112 and 114, respectively. A first PMOS transistor 116 serves as a capacitor between supply Vhigh_es and lead line $S_1$. A second PMOS transistor 118 also turns on to raise supply Vhigh_nwell when a voltage at lead line S2 is greater than a voltage at lead line 51.

Referring now generally to the Figures and particularly to FIG. 12, FIG. 12 shows an exemplary electrode switch circuit 120 of the electrode switch module 52 of FIG. 6 in accordance with aspects of the present invention. In certain aspects, each electrode is either left partially floating (e.g., constrained by diodes 122 and 124), or connects to one of lead lines S1 or S2 in response to control signals, e.g., esc_s1 and esc_s2 from control logic 60. For example, when signal esc_s2 is asserted, level shifter 126 provides a high level (e.g., to Vhigh_nwell) at the input to inverter 128, which is also powered by Vhigh_nwell, thus turning on PMOS transistor 130 to couple the electrode to the second lead line S2. Similarly, when signal esc_s1 is asserted, level shifter 132 provides a high level at the gate of NMOS transistor 134 to couple the electrode to lead line $S_1$.

In this fashion, the electrodes 16.A, 16.B, 16.C and 16.D can be switched to either $S_1$ or $S_2$ based on control signals esc_s1 and esc_s2. Further, supply Vhigh_nwell may typically be used only for the electrode switch and associated PMOS devices, and can be charged to a highest of $S_1$, $S_2$, or the electrode (e.g., using Schottky diode 122). As shown in Table 1 below, switches formed by transistors 134 and 130 can be biased to accommodate avoidance of latch-up issues (e.g., utilizing Vhigh_nwell).

TABLE 1

| Transistor 134 Gate Voltage | | Transistor 130 Gate Voltage | |
|---|---|---|---|
| ON | OFF | ON | OFF |
| Vhigh_es | Vlow | Vlow | Vhigh_nwell |

In order to avoid latch-up during "unipolar" pacing, e.g., where the voltage of concern is between an electrode 16.A, 16.B, 16.C and 16.D and the first buslead line S1, as opposed to being between the cathode wire S1 and the anode wire S2, as in typical pacing), Schottky diodes 122 and 124 are used. Further, another a NMOS transistor can be included in parallel with PMOS transistor 130 in order to contribute additional current in enabling the path between the second lead line S2 and the electrode 16.A, 16.B, 16.C and 16.D when the voltage of the second lead line S2 is relatively low.

Implantable CMOS Device Power Supply Control Methods

Using the present power generation and latch-up protection circuits, methods of generating supplies from interface signals $S_1$ and $S_2$ between a controller device 20 and a satellite 16.A, 16.B, 16.C and 16.D, and methods of controlling an electrode switch 52, will now be discussed. Using these methods, along with the circuitry and interface structure described herein, can support a low cost and robust power generation and voltage protection approach suitable for implantable devices having substantially minimized interfaces.

Figure 13:
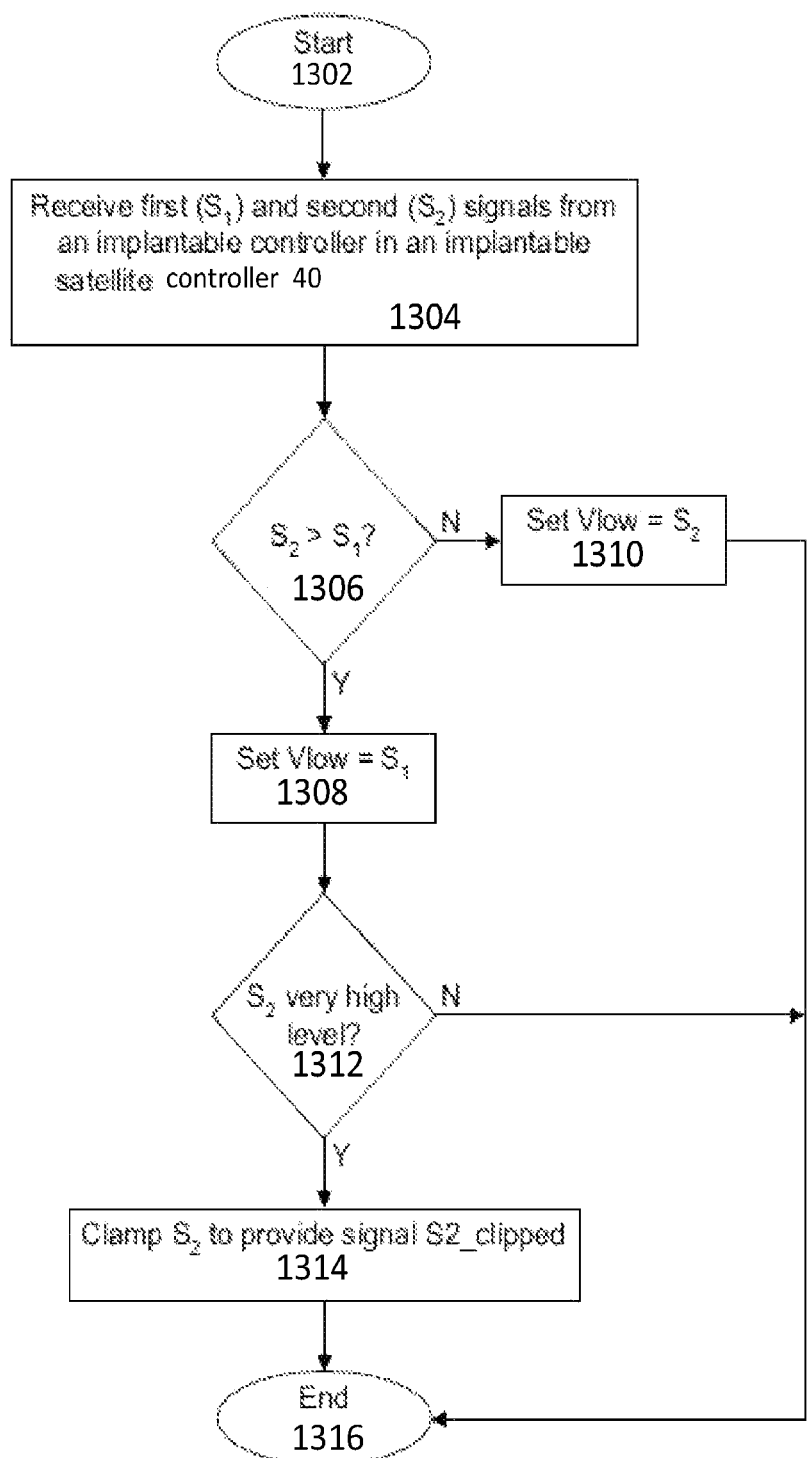
FIG. 13 illustrates a flow diagram for an exemplary method of generating power supplies for the multi-electrode pacing leads of FIG. 4 in accordance with other aspects of the method of the present invention.

Referring now generally to the Figures and particularly to FIG. 13, FIG. 13 shows a flow diagram for an exemplary method of generating supplies in accordance with aspects of the present invention. The flow can begin (1302), and first signal $S_1$ and second signals $S_2$ from the pacemaker controller 54 can be received in a satellite controller 40 coupled to the pacemaker 20 (1304). If a voltage of $S_2$ is greater than that of $S_1$ (1306), substrate supply Vlow can be set at a level of $S_1$ (1308). However, if a voltage of $S_2$ is less than that of $S_1$ (1306), substrate supply Vlow can be set at a level of $S_2$ (1310), completing the flow (1316). If a voltage of signal $S_2$ is at a very high level (1312), such as greater than about 5.5 V, a clipped version of signal $S_2$ (e.g., clipped at about 5 V) can be generated at signal S2_clipped (1014), completing the flow (1316).

Figure 14:
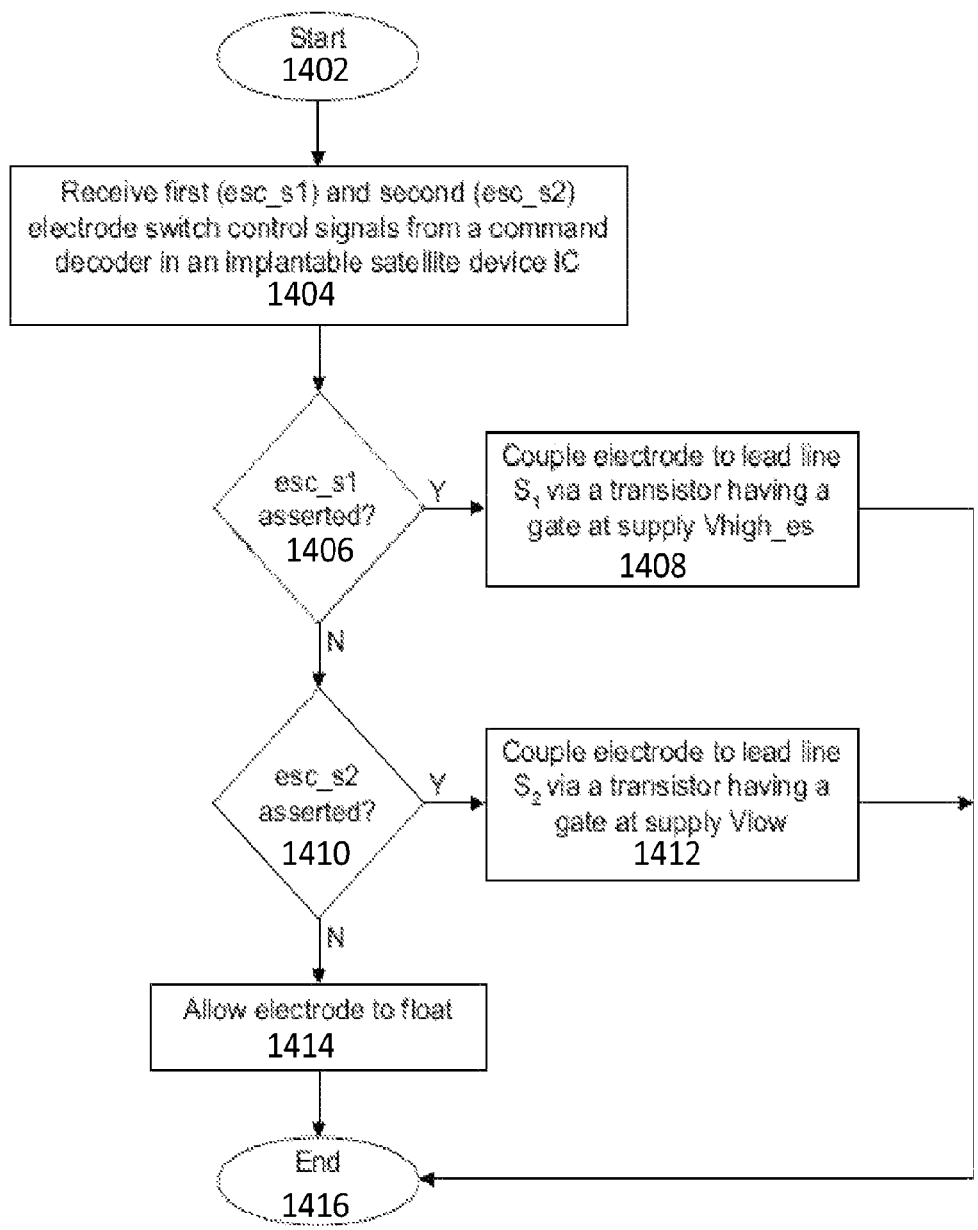
FIG. 14 illustrates a flow diagram for an exemplary method of switching an electrode of FIG. 4 in accordance with still other aspects of the method of the present invention.

Referring now generally to the Figures and particularly to FIG. 14, FIG. 14 shows a flow diagram for an exemplary method of switching an electrode 16.A, 16.B, 16.C and 16.D in accordance with aspects of the present invention. The flow can begin (1402), and first (esc_s1) and second (esc_s2) electrode switch control signals can be received from an implantable satellite controller 40 (1404). If signal esc_s1 is asserted (1406), an electrode can be coupled to lead line $S_1$ (1408). For example, this may be done using an NMOS transistor with a gate biased at supply Vhigh_es, as discussed regarding FIG. 12 and Table 1. If signal esc_s2 is asserted (1410), an electrode can be coupled to lead line $S_2$ (1412). For example, this is done using a PMOS transistor with a gate biased at supply Vlow. If neither of esc_s1 (1106) or esc_s2 (1110) is asserted, the electrode 16.A, 16.B, 16.C and 16.D can be allowed to partially float (1414), completing the flow (1416).

In this fashion, power supply signals can be generated from minimalistic interface signals between a pacemaker controller 54 and a satellite controller 40. Further, the satellite controller 40 can be implemented in CMOS technology, and latch-up concerns can be alleviated in spite of polarity variation in the interface signals. As a result, electrode switching requirements of the satellite controller 40 can be accommodated, along with reduced system costs and satellite controller 40 area savings.

Figure 15:
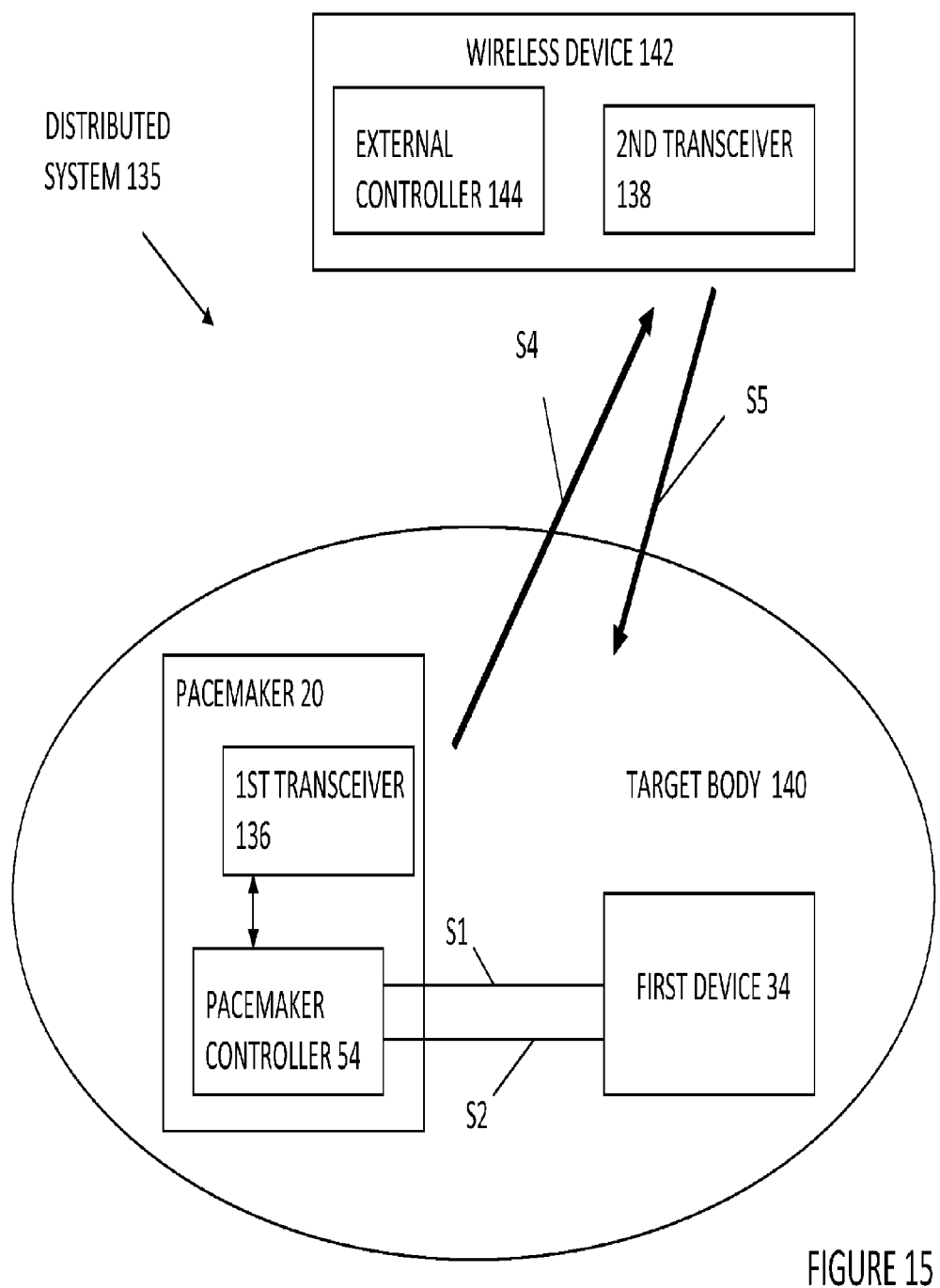
FIG. 15 illustrates wireless communications between an external wireless transceiver and a prior art cardiac pacemaker of FIG. 1, and including the invented implantable device of FIG. 1.

Referring now generally to the Figures and particularly to FIG. 15, FIG. 15 is an illustration of an invented distributed system 135 that includes one more invented devices as described above, such as the implantable device 2 of FIG. 1 and the first device 34 of FIG. 4. The distributed system 135, in accordance with even additional aspects of the invention may be viewed as systems for communicating information acquired from within the target body 140 of subject, e.g., human, where the distributed system 135 includes (1.) the first implantable medical device 34; (2.) the pacemaker 20 further configured with a first transceiver 136 coupled with the pacemaker controller 54, wherein the first transceiver 136 is configured to both transmit an outbound signal S4 to a second transceiver 138 and to receive an external signal S5 from the second transceiver 138 when the pacemaker 20 is implanted within a target animal or mammalian body 140; and (3.) a wireless device 142 comprising an external controller 144 and the second transceiver 138, wherein the second transceiver 138 is configured to receive the outbound signal S4 from the first transceiver 136 and transmit the external signal S4 to the first transceiver 136 when the pacemaker 20 is implanted within the target body 140. The wireless device 142 may be positionable inside the target body 140, on a surface of the target body 140 or separate from the target body 140 during use.

The outbound signal S4 and/or the external signal S5 may be transmitted in any convenient frequency, where in certain aspects the frequency ranges from about 400 to about 405 MHz. The nature of the signal may vary greatly, and may include one or more data obtained from the target body 140 data obtained from the implanted device on device function, control information for the implanted device, power, etc.

Use of the distributed system 135 may include visualization of data obtained with the implantable devices 2 and 34. Some of the present inventors have developed a variety of display and software tools to coordinate multiple sources of sensor information which will be gathered by use of the inventive systems. Examples of these can be seen in international PCT application serial no. PCT/US2006/012246; the disclosure of which application, as well as the priority applications thereof are incorporated in their entirety by reference herein.

Figure 16:
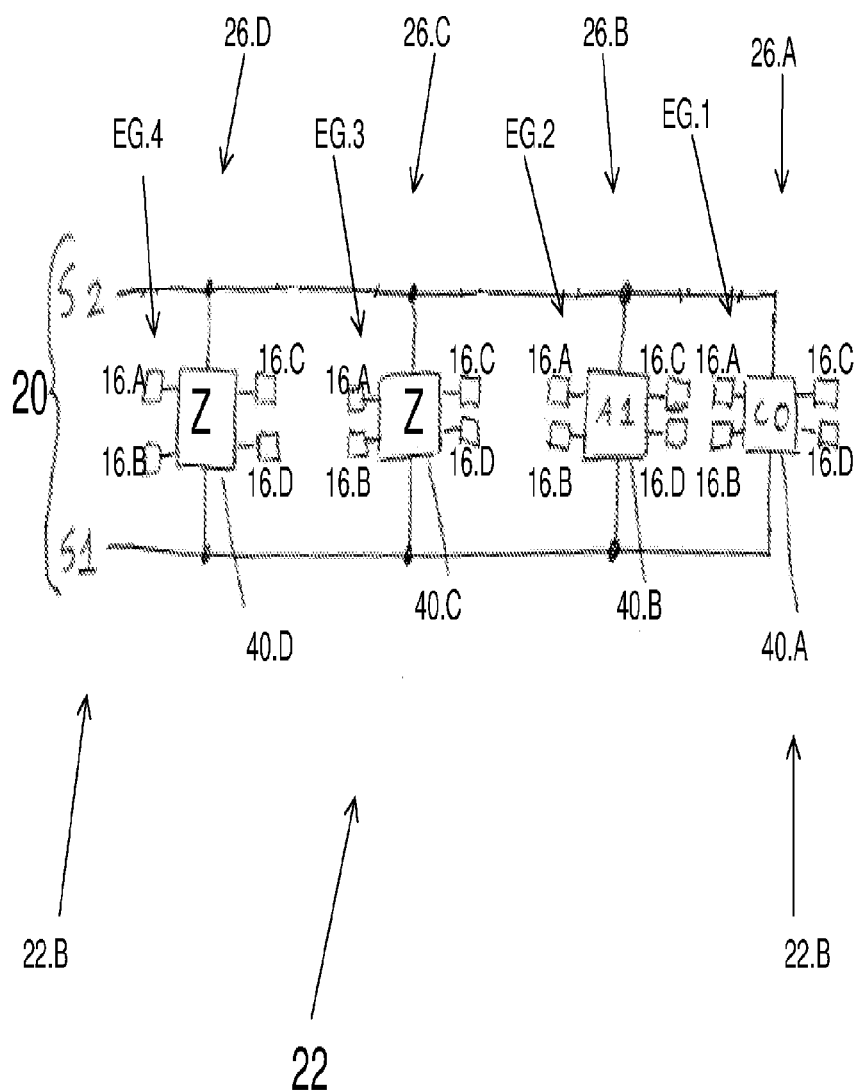
FIG. 16 shows four variations of satellites of FIG. 4 three different types disposed along a lead.

Referring now generally to the Figures and particularly to FIG. 16, FIG. 16 displays an alternate configuration of, in accordance with certain other aspects of the method of the present invention, the satellite controller 40 and the pacemaker controller 54 are configured to be operable in a default mode, e.g., where the satellite controllers 40 are employed in satellites 26 on a lead 22, 24 and 25 In such an configuration, and the satellite controller 40 may include the default-mode functional block 10.G, which enables the comprising satellite 26 to operate in a default mode without the electrodes 16.A, 16.B, 16.C and 16.D of the same satellite 26 being first powered up and configured. As such, in these configurations a device configuration provided by the satellite controller 40 is functional without power being applied to the satellite controller 40. This default-mode operation allows the implantable medical device 2 and 34, such as the pacemaker system 36, to operate without consuming extra power for electrode configuration. Furthermore, the default-mode operation allows the comprising electrode lead 22, 24 and 25 to easily interoperate with conventional pacing systems. In such configurations, the satellite controller 40 may include the first circuit 10 having the default mode functional block 10.G that enables default operation, e.g., as described above.

In certain configurations, the satellite controller 40 is configured to have a default configuration connecting one supply terminal to one or more effectors 8 and/or electrodes 16.A, 16.B, 16.C and 16.D upon power up of the satellite controller 40. As such, in these configurations, upon power up of the satellite controller 40, the satellite controller 40 assumes a default configuration with respect to one or more effectors 8 and/or electrodes 16.A, 16.B, 16.C and 16.D that are coupled to the satellite controller 40, without receiving any configuration data from a remote source.

Discussing this function in greater detail, configurations of the present invention provide implantable devices, such as a satellite 26 of a lead 22, 24 and 26 that are operable in a default mode. Such devices may include the first circuit 10, which is configured such that the first circuit 10 is operational upon power up whether or not the first circuit 10 receives configuration data following power up. Other configurations of devices may alternately or additionally include the satellite controller 40, which is configured such that the satellite controller 40 is operational upon power up whether or not the satellite controller 40 receives configuration data following power up. Other configurations of devices may alternately or additionally include the satellite controller 40 comprising the first circuit 10. For example, a pacemaker lead 22, 24 and 25 of the present invention can operate in a default mode after it is coupled to the pacemaker 20, regardless of whether the pacemaker lead 22, 24 and 25 receives electrode configuration signals from the pacemaker 20. In the default mode, a pacemaker lead 22, 24 and 25 can provide pacing functions in response to pacing signals that fall within an accepted range. The ranges of signals that are accepted by a pacemaker lead 22, 24 and 25 are broad enough to include pacing signals generated by many different models of pacemaker cans 20. As such, the pacemaker lead 22, 24 and 25 of the present invention are not limited to being used with only one pacemaker can model 20 or one class of pacemaker cans 20 made by a particular manufacturer.

The present invention provides the ability to replace the preexisting pacemaker 20 with one from a wide variety of makes and models, should the need arise. This can be accomplished while using the existing pacemaker leads 22, 24 and 25. This is desirable over performing an additional surgical procedure to replace the preexisting pacemaker leads 22, 24 and 25. It would be desirable if an implanted pacemaker lead pacemaker lead 22, 24 and 25 could respond to pacing signals generated by one pacemaker model 20 or a class of pacemaker models 20 made by any manufacturer.

Pacemaker leads pacemaker lead 22, 24 and 25 can include one or more satellite controllers 40. Each of the satellite controllers 40 can include a set of eight switches 52.A-52.N of the electrode-switching module 52, e.g., 4 switches 52.A-52.0 or eight switches 52.A-52.H. Each of the switches 52.A-52.N couple or decouple a cathode bus wire S1 or an anode bus wire S2 in the lead to an electrode 16.A, 16.B, 16.C and 16.D. The switches 52.A-52.N may be implemented by a set of transistors according to any convenient circuit design techniques.

A pacemaker lead 22, 24 and 25 of the present invention is connected to a pacemaker 20. The pacemaker lead 22, 24 and 25 is operable in a default mode. In the default mode, the switches 52.A-52.N in the satellite controllers 40 remain in or switch to a default configuration. When the switches 52.A-52.N are in the default configuration, one or more of the electrodes 16.A, 16.B, 16.C and 16.D are coupled to the anode wire S1 and/or the cathode bus anode wire S2, or "cathode wire" S2. In one approach, the switches 52.A-52.N in one or more satellite controllers 40 can be switched to couple a corresponding electrode 16.A, 16.B, 16.C and 16.D to a cathode wire S1 or an anode wire S2. The switches 52.A-52.N can also decouple a corresponding electrode 16.A, 16.B, 16.C and 16.D from both the anode wire S2 and the cathode wire S1 so that the pacemaker 20 cannot send current to that electrode 16.A, 16.B, 16.C and 16.D. Thus, each of the switches 52.A-52.N can be placed in one of three states: decoupled, coupled to the anode wire S2, or coupled to the cathode wire S1.

Turning momentarily to FIG. 16, what is shown is the left ventricular lead 22, or "first lead" 22 includes four satellites 26.A-26.D and which connects to a pacemaker 20 at a proximal end 22.A of the first lead 22. A distal end 22.B of the first lead 22 is located at end furthest from the proximal end 22.A and is coupled with a distal satellite controller 40.A. Positioned more proximally to the proximal end 22.A is a second satellite controller 40.B, then a third satellite controller 40.C, and finally a proximal satellite controller 40.D that is closest to the pacemaker 20 when the first lead 22 is coupled to the pacemaker 20. It is understood that while the example configuration of the first lead 22 of FIG. 16 shows four satellites 26 each having a satellite controller 40.A-40.C, that more or less quantities of satellites 26 and satellite controllers 40 may be located on the first lead 22 in accordance with even other aspects of the method of the present invention.

Each satellite 26 may comprise a satellite controller 40.A-40.D connected to an individual electrode group EG.1, EG.2, EG.3 and EG.4, wherein each electrode group EG.1, EG.2, EG.3 and EG.4 includes a plurality of electrodes 16.A, 16.B, 16.C and 16.D. For example the distal satellite controller 40.A is connected to a distal group of electrodes EG.1 comprising four electrodes 16.A, 16.B, 16.C and 16.D; the second satellite controller 40.B is connected to a second group of four electrodes EG.2; the third satellite controller 40.C is connected to a third of four electrodes EG.3; and the proximal satellite controller 40.D is connected to a proximal group of four electrodes EG.4.

Within each satellite controller 40.A-40.D are semiconductor switches 52.A-52.N, omitted for clarity from FIG. 16, which can each selectively connect a particular electrode to one of either the cathode wire S1 or to the anode wire S2, or can leave the electrode at a high impedance relative to the wires S1. Each electrode 16.A, 16.B, 16.C and 16.D has may be coupled with two separate switches 52.A-52.N wherein one of the two switches 52.A-52.N is coupled to the cathode wire S1, and the remaining switch 52.A-52.N is coupled with the anode wire S2 (and the other coupled to S2), and thus in this configuration each chip has four electrodes 16.A, 16.B, 16.C and 16.D, so that the electrode-switching module 52 of each of the satellite controllers 40.A-40.D contains eight such switches 52.A-52.H. In the exemplary configuration of the first lead 22, which has four satellite controllers 40.A-40.C, there are thus thirty-two such switches 52.A-52.N.

As shown in FIG. 16, an exemplary configuration of the satellite controllers 40.A-40.C is not identical in their default function. A first type of each satellite controller 40.A-40.C, which, in default, connects electrodes 16.A, 16.B, 16.C and 16.D to the cathode wire S1. A second type of each satellite controller 40.A-40.C, in default, connects electrodes 16.A, 16.B, 16.C and 16.D to the anode wire S2. A third type of each satellite controller 40.A-40.C, in default, does not connect electrodes 16.A, 16.B, 16.C and 16.D to either of the anode wire S2 or the cathode wire S1.

In the configuration of FIG. 16, the distal satellite controller 40.A is of the first device type (here called "c0") namely with a default connection to the cathode wire S1. The second satellite controller 40.B is of the second device type (here called "a1") namely with a default connection to the anode wire S2. The third satellite controller 40.C and the proximal satellite controller 40.D are of the third device type (here called "Z") and in default mode do not connect electrodes 16.A, 16.B, 16.C and 16.D to either the cathode wire S1 and the wire S2.

With a legacy pacemaker 20 sending a cardiac pacing pulse in a single-wire way via the cathode wire S1, and using body tissue as a return for the pulse emitted on the cathode wire S1, then the only active electrodes 16.A, 16.B, 16.C and 16.D are those of the distal satellite group EG.1 of the distal satellite 26.A, which are coupled with the cathode wire S1 in default mode.

With a legacy pacemaker 20 sending a pulse in a two-wire way on the cathode wire S1 and the anode wire S2 then in default mode the active electrodes include distal satellite group EG.1 of the distal satellite 26.A, which are coupled with the cathode wire S1 in the c0 default mode; and the second satellite group EG.2 of the second satellite 26.C, which are coupled with the anode wire S2 in the a1 default mode.

Some types of pacemaker cans 20 are able to generate configuration signals that can control the states of the switches 52.A-52.N in the satellite controllers 40.A-40.D that are in an implantable pacemaker lead 22, 24 and 25. These types of pacemaker cans 20 are able to change the states of the switches 52.A-52.N in order to stimulate any of the electrodes 16.A, 16.B, 16.C and 16.D in the lead 22, 24, and 25 in any desired pacing configuration.

However, other types of pacemaker cans 20 cannot generate configuration signals for controlling the states of the switches 16.A, 16.B, 16.C and 16.D. According to the present invention, one or more of the electrodes 16.A, 16.B, 16.C and 16.D are coupled to the anode wire S2 and/or cathode wire S1 in a default mode. Therefore, a pacemaker 20 that is not able to generate configuration signals for changing the states of the switches 52.A-52.N is still able to send current to at least one of the electrodes 16.A, 16.B, 16.C and 16.D in a default mode. The default configuration of the switches 52.A-52.N allows any pacemaker 20 that is able to generate pacing signals within an accepted range to stimulate the cardiac tissue and provide at least a basic pacing function.

According to some configurations of the present invention, an implantable pacemaker lead 22, 24 and 25 is already in a functional default mode before the lead 22, 24 and 25 is coupled to the pacemaker 20. According to other configurations of the present invention, an implantable pacemaker lead 22, 24 and 25 enters a functional default mode after the lead 22, 24 and 25 is coupled to a pacemaker 20, and the power supply voltage reaches or exceeds a predefined threshold voltage. As mentioned above in connection with FIG. 10, the satellite controller 40 on a pacemaker lead 22, 24, and 25 can be classified as three types of default mode satellite controllers 40: anode default a1, cathode default c0, and off default. The anode default second satellite controller 40.B contains switches 52.A-52.N that couple one or more electrodes 16.A, 16.B, 16.C and 16.D to the anode wire S2 in default mode. The direct electrical current lead impedance for an anode default satellite controller 40.B can be, for example, in the range of about 20 to about 225Ω, such as from about 112 to about 225Ω, such as about 120Ω.

Cathode default distal satellite controller 40.A contains switches 52.A-52.N that couple one or more electrodes 16.A, 16.B, 16.C and 16.D to the cathode wire 51 in default mode. The direct electrical current lead impedance for a Cathode default distal satellite controller 40.A, for example, in the range of about 15 to about 80Ω, such as from about 20 to about 80Ω, including about 40Ω. If the pulse amplitudes of the pacing signals are increased, the lead impedances are reduced.

The satellite controllers 40 that are off by default, e.g., the third satellite controller 40.C and the proximal distal satellite controller 40.D of FIG. 16, contain switches 52.A-52.N that disconnect all coupled electrodes 16.A, 16.B, 16.C and 16.D from the anode wire S2 and the cathode wire S1 when in default mode. A satellite controller 40 that may be decouple electrodes 16.A, 16.B, 16.C and 16.D from power sources by default can be, for example, in the range of about a megohm impedance until turned on using a pacemaker 20.

A pacemaker lead 22, 24 and 25 of the present invention can have satellite controllers 40 with any number of switches 52.A-52.N that are coupled to a corresponding number of electrodes 16.A, 16.B, 16.C and 16.D. For example, in one instance, an electrode configuration can be set to provide the patient an effective therapeutic procedure. In another instance, the electrode configuration can be reset to provide the same patient a more effective therapeutic procedure.

Figure 17:
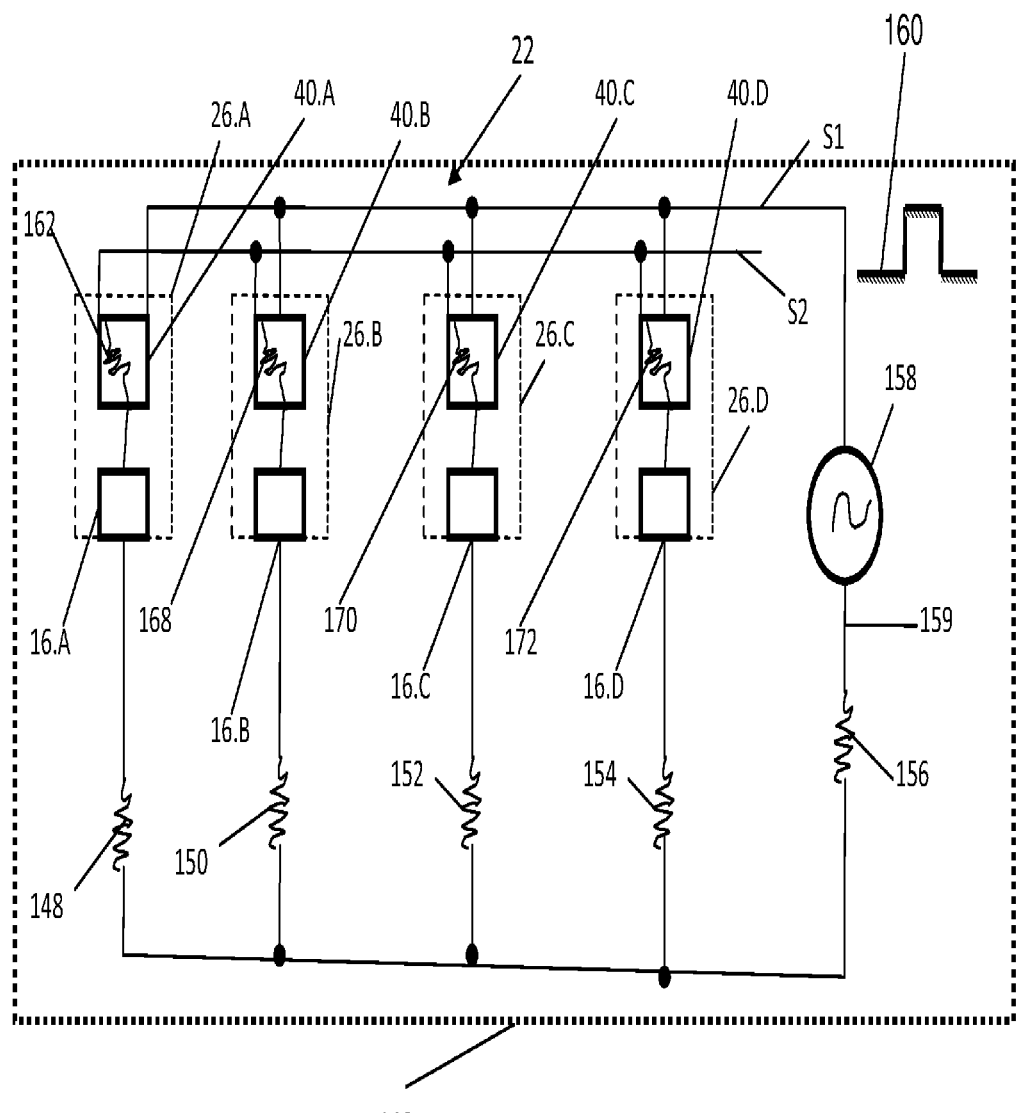
FIG. 17 shows a lead of FIG. 4 with several satellites of FIG. 16 along with an impedance model for a human subject.

Referring now generally to the Figures and particularly to FIG. 17, FIG. 17 shows an impedance model 146 for the first lead 22, in relation to the human target body 140. The impedance model of FIG. 17 is helpful in understanding an extended bipolar pacing capability according to other aspects of the method of the present invention. The human target body 146 is modeled by impedances 148, 150, 152, 154, and 156 as will be discussed below. An arbitrary electrical potential source 158, or "source potentiometer" 158, is shown, which might be the first pacemaker system 36.

The first lead 22 in FIG. 17 has the exemplary four satellites 26.A, 26.B, 26.C and 26.D. Each satellite has a satellite controller 40.A, 40.B 40.C and 40.D. Each satellite controller 40.A, 40.B and 40.D provides an interface between the cathode wire S1 and the anode wire S2 on the one hand, and a respective electrode 16.A, 16.B, 16.C and 16.D. It is understood that although each satellite 26.A, 26.B, 26.C and 26.D might have four or more electrodes or 16.A, 16.B, 16.C and 16.D and that only one such electrode 16.A, 16.B, 16.C and 16.D is shown in FIG. 17 for clarity of explanation.

In the impedance model 146 of FIG. 17 we can discuss what happens when a pulse is emitted by the source potentiometer 158, for example with the source potentiometer 158 coupled to the human target body 140 at a location 159 in a way that is omitted for clarity in FIG. 17. The source potentiometer 158 might, for example, include of a metal housing of that is in electrical contact with the human target body 140. The source potentiometer 158, in this example being a two-terminal device, is also coupled to the cathode wire S1. In a simple case, the distal satellite 26.A is active, meaning that the first electrode 16.A of the distal electrode group EG.1 is coupled to the cathode wire S1 during most or all of the duration of the pulse. At the same time, it may thus be that none of the other satellites 16.B, 16.C and 16.D is active, meaning that none of their electrodes is strongly coupled to the cathode wire cathode wire S1 or the anode S2 during most or all of the duration of the pulse. As such, the distal controller 40.A of the distal satellite 26.A is serving as a "c0" device as described above in connection with FIG. 16.

Meanwhile, in this configuration, the second satellite controller 40.B may act as an "a1" device as described above in connection with FIG. 17, i.e., coupling electrodes to the anode wire S2 luring most or all of the duration of a cardiac pacing pulse 160. The third satellite controller 40.C and the proximal satellite controller 40.D may leave their respective electrodes 16.C and 16.D and electrode groups EG.3 and EG.4 at a high impedance relative to both of the cathode wire S1 and the anode wire S2 during most or all of the duration of the pulse, thus for example being Z devices as described in connection with FIG. 16.

In such a case, we model the electrical environment for a pulse 160 traveling from the source potentiometer 158 to the target body 140 as follows. The distal electrode group EG.1 of the first satellite 26.A is coupled to the cathode wire S1, and thus to the source potentiometer 158, with an impedance internal to the distal satellite controller 40.A that is low in comparison to the assumed impedances 148 (nominally 100 ohms) and 156 (nominally 1000 ohms). It is desired that this impedance that is internal to the distal satellite controller 40.A be low so that nearly all of the energy of the pulse may be delivered to tissue nearby to the electrode, such as heart muscle tissue. In an exemplary configuration, the internal impedance of the distal satellite controller 40.A, coupled between the cathode wire S1 and the distal electrode group EG.1 might be only fifty ohms or so.

A problem, however, is that if the impedance internal to the satellite controller 40.A between the cathode wire S1 and the distal electrode group EG.1 is too small, then satellite controller 40.A will not be able to develop electrical power of the in power extraction module 44 of FIG. 6 and thus the distal electrode group EG.1 will not be able to effectively function. The various impedances being discussed above serve as a voltage divider, and the voltage divider will thus allocate only a small portion of the direct electrical current potential to the satellite controller 40.A because the internal impedance of the satellite controller 40.A between the cathode wire S1 and each electrode 16.A, 16.B, 16.C and 16.D of the distal electrode group EG.1 is small.

For example if a cardiac pacing pulse 160 produced by the source potentiometer 158 has a voltage of about two volts, then the series connection of 1000 ohms, 100 ohms, and fifty ohms will leave only around 83 millivolts developed at the distal satellite controller 40.A. This may not be enough voltage to power the distal satellite controller 40.A.

It might thus be thought that the way to proceed is to make the internal impedance of the distal satellite controller 40.A between the cathode wire S1 and the electrodes 16.A, 16.B, 16.C and 16.D of the distal electrode group EG.1 rather larger, for example some tens of thousands of ohms, in an exemplary configuration 40 kilohms. The result would be that nearly the full voltage from source potentiometer 158 would be developed across the distal satellite controller 40.A, thereby enough potential to permit the power extraction module 44 to extract enough power to power the distal satellite controller 40.A. Unfortunately, however, an impedance this high will result in an unacceptable degradation of the potential delivered to the tissue of the target body 140, represented for example by the modeled impedance 156.

According to an aspect of the method present the invention, the following may be instantiated. The distal satellite controller 40.A initially presents a large enough impedance between cathode wire S1 and electrodes 16.A, 16.B, 16.C and 16.D of the distal electrode group EG.1 so as to permit the extraction and storage of operating power. When the distal satellite controller 40.A detects the beginning of a pulse, the distal satellite controller 40.A may count between about 30 microseconds and about 50 microseconds, and then close a switch 52.A which reduces the impedance of the distal satellite controller 40.A as defined by at least one active electrode 16.A, 16.B, 16.C and 16.D of the distal electrode group EG.1 and the cathode wire S1 to a very small value, characteristically around 50 ohms. This smaller impedance may be maintained for the remaining duration of the pulse.

Figure 18:
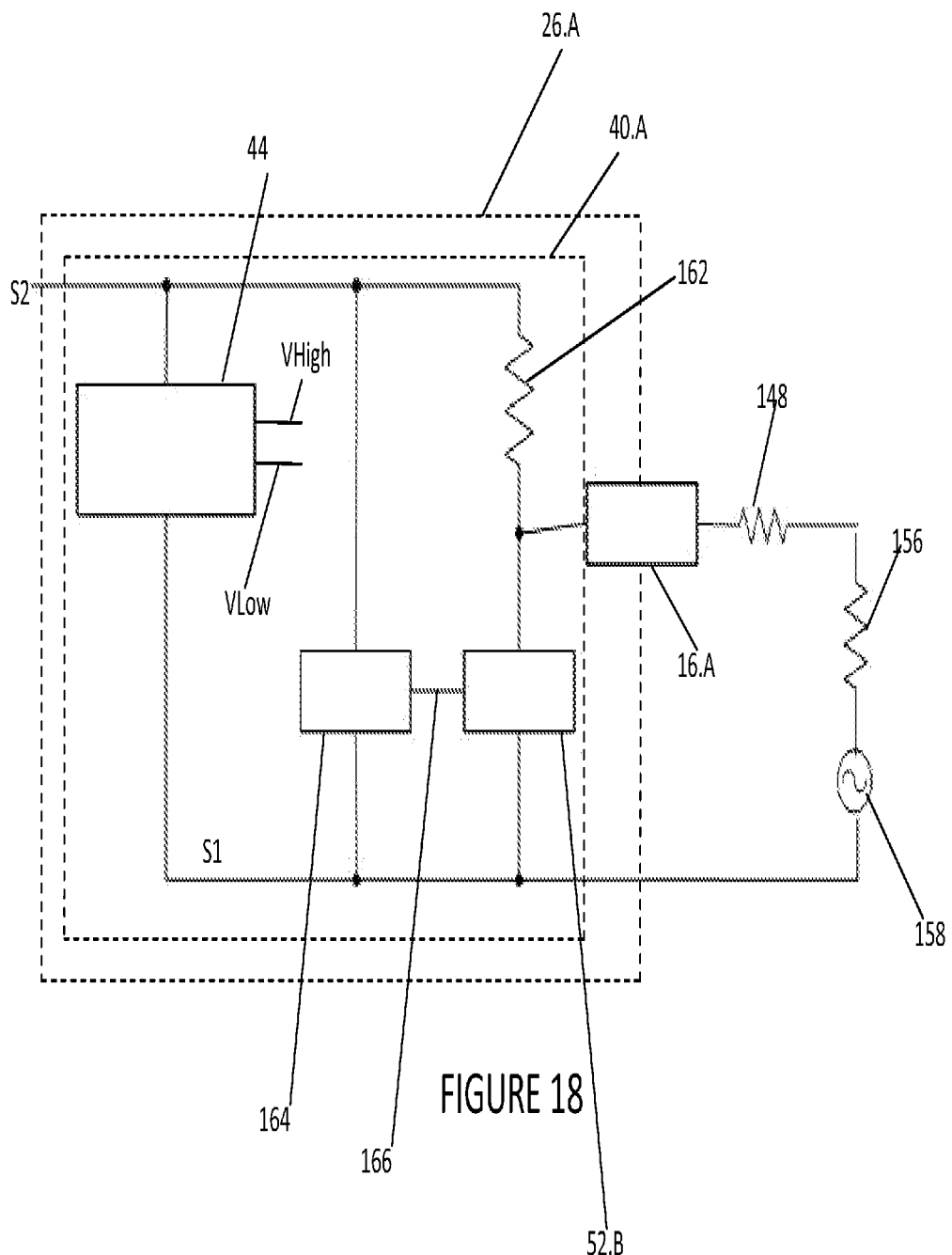
FIG. 18 shows one of the satellites of FIG. 17 in greater detail.
Figure 19:
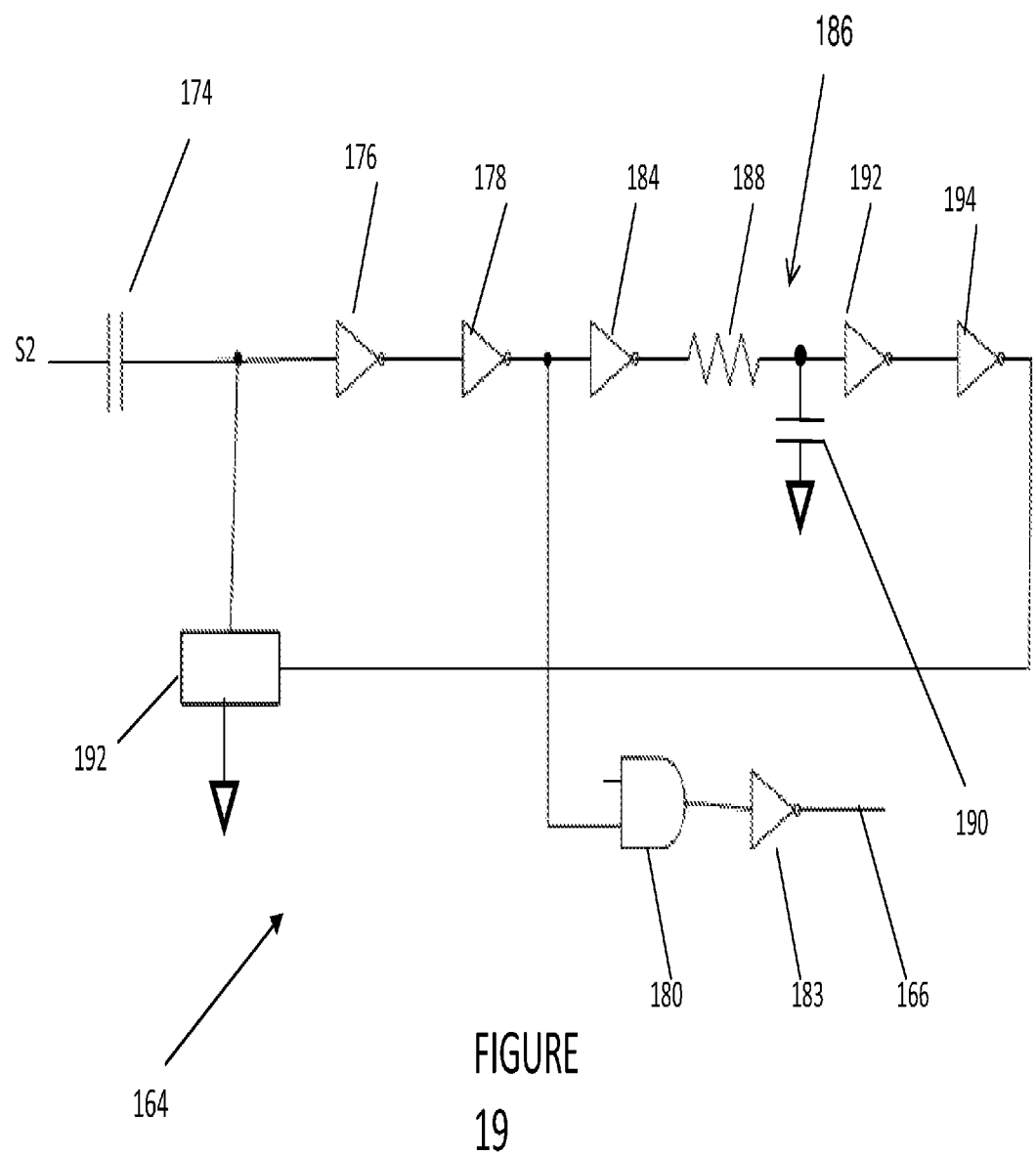
FIG. 19 shows a timing and control circuit such as might be used in the satellite of FIG. 18.

Referring now generally to the Figures and particularly to FIG. 18 and FIG. 19, FIG. 19 shows a current path comprising the voltage potentiometer 158, the modeled target body impedances 156 and 154, the electrode 16.A of the satellite 26.A which connect to the cathode wire S1 and the current path passing back to the voltage source potentiometer 158. As noted previously, the distal satellite controller 40.A is located within the exemplary distal satellite 26.A. The distal satellite controller 40.A further includes the power extraction module 44 of FIG. 6 that develop power signals for the distal satellite controller 40.A including the power signal Vhigh.

Initially switch 52.B is open, and thus the voltage presented at the first electrode 16.A of the distal electrode group EG.1 passes through an impedance 162 to the anode wire S2 and thence to the power extraction module 44, which also connects to the cathode wire S1. As discussed further below, voltage present at electrodes 16.A, 16.B, 16.C and 16.D of other satellite controllers 16.B-16.D likewise pass through respective impedances to the anode wire S2, may also be passing some charge to the power extraction module 44. Thus the power extraction module 44 is able to develop power for the distal satellite controller 40.A, and distal satellite controller 40.A may include power storage capacity.

The arrival of the pacing pulse 160 arrives at an edge detector and timer 164. After the passage of about 30 microseconds, or as long as 50 microseconds, an electrically conductive first line 166 is asserted by the distal satellite controller 40.A, and this assertion turns on a second switch 52.B. This enablement of the second switch 52.B by the distal satellite controller 40.A electrically connects the electrode 16.A to the cathode wire S1 with a relatively low impedance, nominally 50 ohms. This low impedance at the second switch 52.B means that the full potential available from the cathode wire S1 is available at the electrode 16.A, and thus nearly the entire pacing pulse 160 is now presented across the modeled target body impedances 148 and 156. Stated differently, nearly the full pacing pulse reaches the heart muscle adjacent the first electrode 16.A of the distal electrode group EG.1 of the distal satellite 26.A.

As is portrayed in FIG. 18, the distal satellite controller 40.A has the internal impedance 162 which permits the voltage presented at the first electrode 16.A of the first electrode group EG.1 by the cathode wire S1 to pass through impedance 162 to the anode wire S2 and thence through the power extraction module 44. It will be recalled, however, that in the exemplary configuration of FIG. 17, the distal satellite controller 40.A is not the only satellite controller 40.A-40.D in the system. Each of the additional satellite controllers 40.B-40.D also have some impedance corresponding to impedance 162, which couples the electrodes 16.A, 16.B, 16.C and 16.D of the electrode group EG2-EG.4 of each remaining satellite controller to the anode wire S2. For example, the second satellite controller 40.B will have some impedance 168 coupling electrode 16.B with anode wire S2; the third satellite controller 40.C will have some impedance 170 coupling electrode 16.D with anode wire S2; and the proximal satellite controller 40.D will have some impedance 172 coupling electrode 16.C with anode wire S2.

The impedances 162, 168, 170, and 172 each couple with respective modeled impedances 148, 150, 152 and 154 to help in coupling the body tissue of the target body 140 through the electrodes 16.A, 16.B, 16.C and 16.D of the electrode groups EG.1-EG.4 to the anode wire S2, and from there to the power extraction module 44, shown in FIG. 5. In this way, all four of the satellite controllers 40.A-40.C can contribute to the charging-up of the power extraction module 44.

It will be appreciated that while this configuration shows four satellite controllers 40.A-40.D total, of which three assist in charging the power extraction module 44 of the fourth chip, it is not required to have this number of four satellite controllers 40.A-40.D to enjoy the teachings of the invention. The number of satellite controllers 40.A-40.D might be lesser or greater without departing from the invention.

Referring now to the Figures and particularly to FIG. 19, FIG. 19 details the edge detector and timer 164, or "EDT" 164. The cardiac pacing pulse 160 arriving at S2 by way of the first electrode impedance 162 of the first electrode 16.A passes through a first EDT capacitor 174, a first EDT gate 176 and a second EDT gate 178, and through a third EDT gate 180 and a fourth EDT gate 182, rendering first line 166 low, i.e. "low" in this case means the state leaving the second switch 52.B open. The cardiac pacing pulse 160 passes through the first EDT gate 176 and the second EDT gate 178 to reach a fifth EDT gate 184, where an RC circuit 186 comprising an RC circuit resistor 188 and an RC capacitor 190 and may exhibit an exemplary time constant of 7.8 microseconds. After several a period of time equal to time constants of the RC time constant have passed, preferably adding up to adding up to about an exemplary 30 microseconds, the output of a sixth EDT gate 192 and a seventh EDT gate 194 reaches a first EDT switch 196 which then turns on. This change propagates through the first EDT gate 176 and a second EDT gate 178, a third EDT gate 180 and a fourth EDT gate 182 and asserts first line 166. This assertion of the first line 166 turns on the second switch 52.B which ties the exemplary first electrode 16.A and the cathode wire S1 together, as previously mentioned.

It will be appreciated that the teachings of the invention offer their benefits regardless of the exact circuitry employed to bring about the results described. For example the edge detector and timer 164 could be the circuitry shown in FIG. 6, or could be any other suitable circuitry known in the art.

Returning briefly to FIG. 6, the power extraction or power generation module 44 is shown. The cathode wire S1 and the anode wire S2 receive power from outside of the satellite controller 40. The power extraction module 44 has the task of developing an appropriate power supply for use within the satellite controller 40, shown in FIG. 6 with voltage outputs denoted as Vhigh and Vlow respectively.

Figure 20:
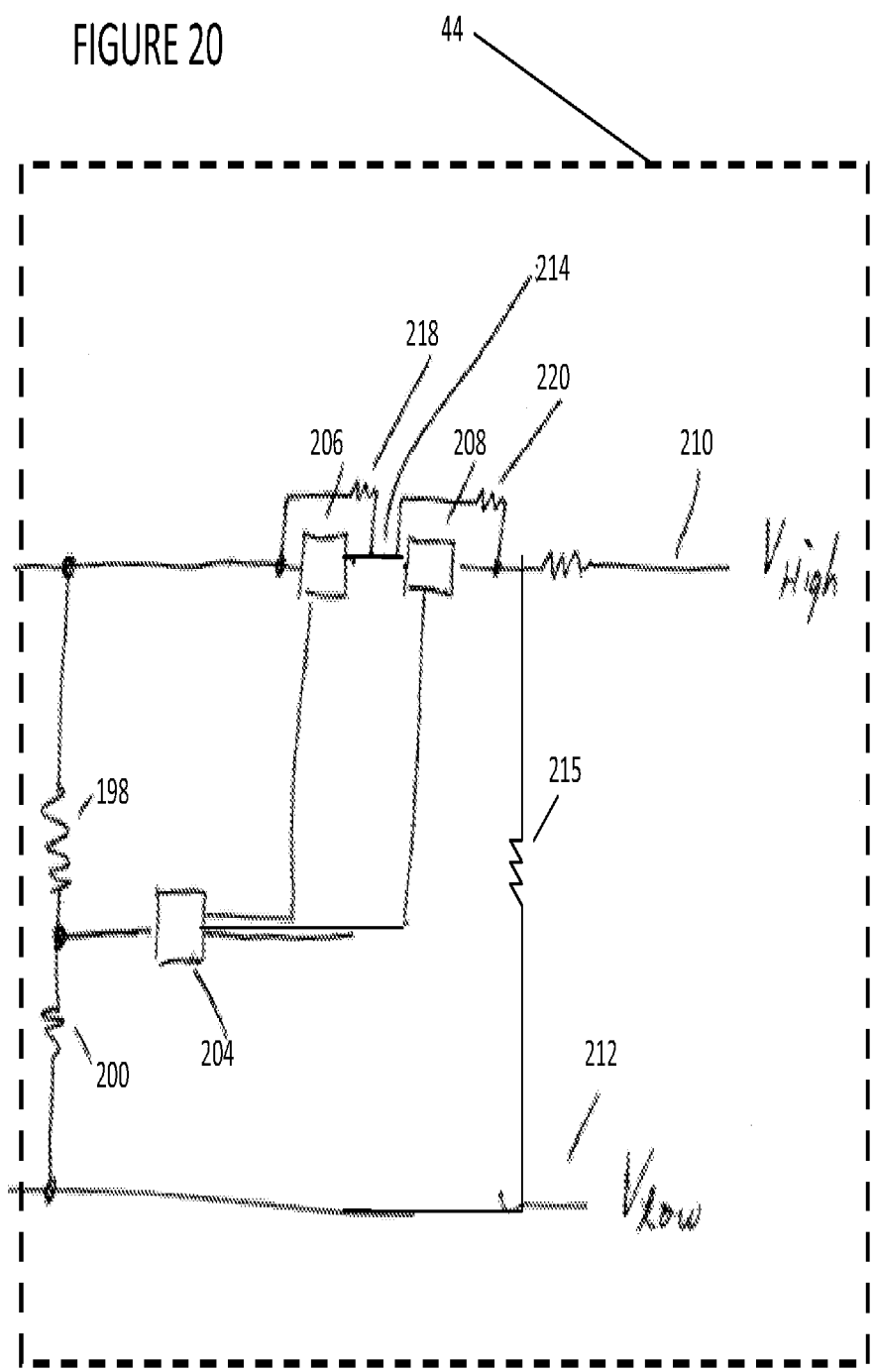
FIG. 20 shows a power extraction circuitry as might be used in the integrated circuit of the satellite of FIG. 18.

Referring now generally to the Figures and particularly to FIG. 20, FIG. 20 details a portion of the power generation module 44 in a variation of the exemplary satellite controller 40.A according to the invention. A voltage divider 196 defined by a first resistor 198 and a second resistor 200 provides an input to a first control circuitry 204 which controls a first PMOS transistor 206, or first PMOS switch 206, and a second PMOS transistor 208, or a second PMOS switch 208. In this way the voltage at the cathode wire S2 is selectively delivered to a second electrically conductive second line 210, while the voltage at the cathode wire S1 is connected to a third electrically conductive third line 212.

The design challenge is that the power provided from the cathode wire S1 and at the anode wire S2 to the exemplary satellite controller 40 in FIG. 6 may be as small as two volts. What's more, it is preferable is that the satellite controller 40 should withstand as much as ten volts present between the cathode wire S1 and at the anode wire S2.

In prior-art power a high-voltage PMOS transistor was employed in the current path from anode wire S2 of the vhigh_core signal of the power generation module 44. The voltage threshold of the prior-art high-voltage PMOS transistor was typically about 1.6 to 1.7 volts. Experience showed, however, that it was not possible to count on the threshold being reached for this prior-art transistor. In this prior art design, that the high-voltage PMOS transistor would fail to reach its threshold, would fail to conduct, and thus would fail to develop the Vhigh power line.

The first control circuitry 204 turns on the first PMOS transistor switch 206 and the second PMOS transistor switch 208 conducts because the available input of at least two volts, e.g., at the cathode wire S2, is well over the voltage required (0.9 volts) to cause the second switch transistor 208 to conduct, even with some impedances elsewhere in the power generation module 44. In the apparatus according to the invention, the first PMOS transistor 206 and the second PMOS transistor 208 are provided in series, each of which in this configuration is a PMOS transistor. Each of the first PMOS transistor 206 and the second PMOS transistor 208 has a threshold of about 0.9 volts.

The first PMOS switch 206 once turned on, supplies potential at a first location point 214 to the first PMOS switch 206 and thus a control signal from the first control circuitry 204 is able to provide gate potential to the second PMOS transistor switch 208. Again the available input at a first location 214 is on the order of at least two volts an slightly less due to impedances elsewhere in the circuit, but well over the 0.9 volts required to cause second PMOS transistor switch 208 to conduct.

In a steady state after both the first PMOS switch 206 and the second PMOS switch 208 are conducting, a third resistor 218 and a fourth resistor 220 help to balance the voltage drop across the first PMOS switch 206 and the second PMOS switch 208, so that each of the first PMOS switch 206 and the second PMOS switch 208 shoulders about half of the burden (here, about half of the potential across the series of two switches). The first PMOS switch 206 and the second PMOS switch 208 are each rated for as much as 5.5 volts, meaning that the switch first PMOS switch 206 and the second PMOS switch 208 in series can withstand about eleven volts. The electrical load ruggedness of the first PMOS switch 206 and the second PMOS switch 208 satisfies the design goal of the satellite controller 40 being able to withstand as much as ten volts across the cathode wire S1 and the anode wire S2. In the circuit layout of FIG. 20, it is preferable that the first PMOS switch 206 and the second PMOS switch 208 be laid out with as close as possible a physical match.

More particularly, the third resistor 218 and the fourth resistor 220 are used to balance the voltage drop across the first PMOS switch 206 and the second PMOS switch 208 when the first PMOS switch 206 and the second PMOS switch 208 are both in the off state, i.e. not carrying current. For example, when the pacing voltage pulse 160 is applied across the anode wire S2 and the cathode wire S1 is larger than 5 Volts, a voltage divider effect of the first resistor 198 and the fourth resistor 200 will direct the control circuitry 204 to turn the first PMOS switch 206 and the second PMOS switch 208 into the off state, i.e., not carrying current in parallel with the third resistor 218 and the fourth resistor 220. Therefore, in this example the third resistor 218 and the fourth resistor 220 are used to bias the first PMOS switch 206 and the second PMOS switch 208. In addition, a fifth resistor 215, connects from a right side terminal of the fourth resistor 208 to the Vlow signal. i.e., the s2_clipped signal of FIG. 10. The impedance value of the fifth resistor 215 equals the combined impedance value of the third resistor 218 plus the impedance value of the fourth resistor 220. Therefore, the impedance value of the third resistor 218 plus the impedance value of the fourth resistor 220 together with the fifth resistor 215 form another 1:1 ratio resistor divider to protect the node s2_power signal from seeing a higher than 5.5 voltage when the incoming pacing voltage rating is at 10 V maximum clipped What is described, then, is a cascade of PMOS switches in a power extraction application.

Referring now generally to the Figures and particularly to FIG. 6, the switching module 52 is shown. The cathode wire S1 and the anode wire S2 receive signals from one or more of the exemplary satellite controllers 40. The switching module 52 provides a tri-state driver for each electrode 16.A, 16.B, 16.C and 16.D. The term "tri-state driver" means that a particular electrode 16.A, 16.B, 16.C and 16.D might be connected to the cathode wire S1 or to the anode wire S2 or might be at a high impedance relative to both of the cathode wire S1 and the anode wire S2, i.e., "floating". The drivers are controlled by the control lines 51 from the command interpretation circuitry 50.

Figure 21:
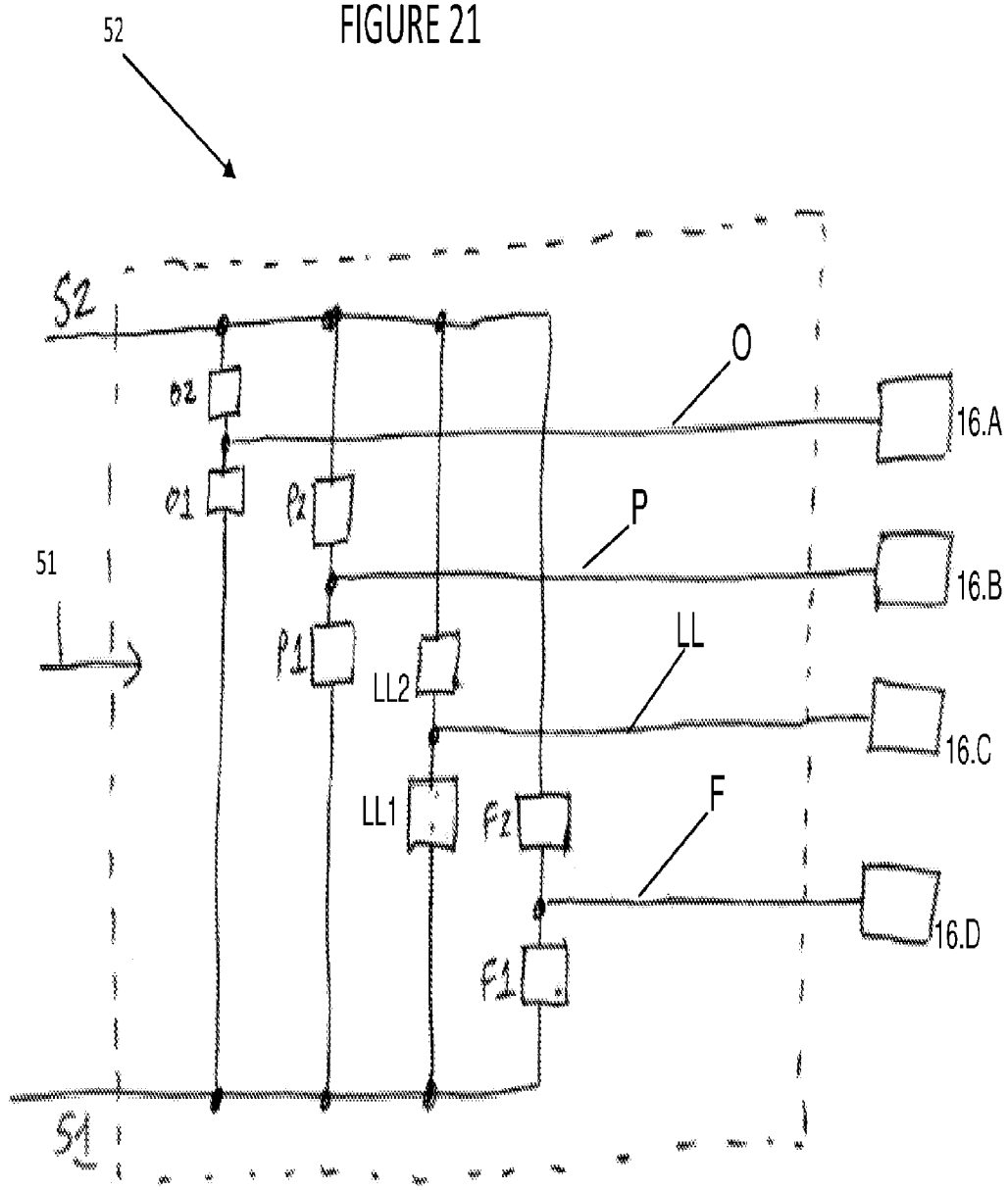
FIG. 21 shows a switching circuitry as might be used in the integrated circuit of the satellite of FIG. 18.

Referring now generally to the Figures and Particularly to FIG. 21, FIG. 21 details a portion of the switching module 52 in a system according to certain aspects of the method of the invention. Electrode 16.A is connected by an electrically conductive third line O with switches O2 and O1 which together comprise a tri-state driver. Electrode 16.B is connected by an electrically conductive fourth line P with switches P2 and P1 which together comprise a tri-state driver. Electrode 16.C is connected by a line LL with switches LL2 and LL1 which together comprise a tri-state driver. Finally, the representative electrode 16.A is connected by a fifth line F with switches F2 and F1, which together comprise a tri-state driver.

Figure 22:
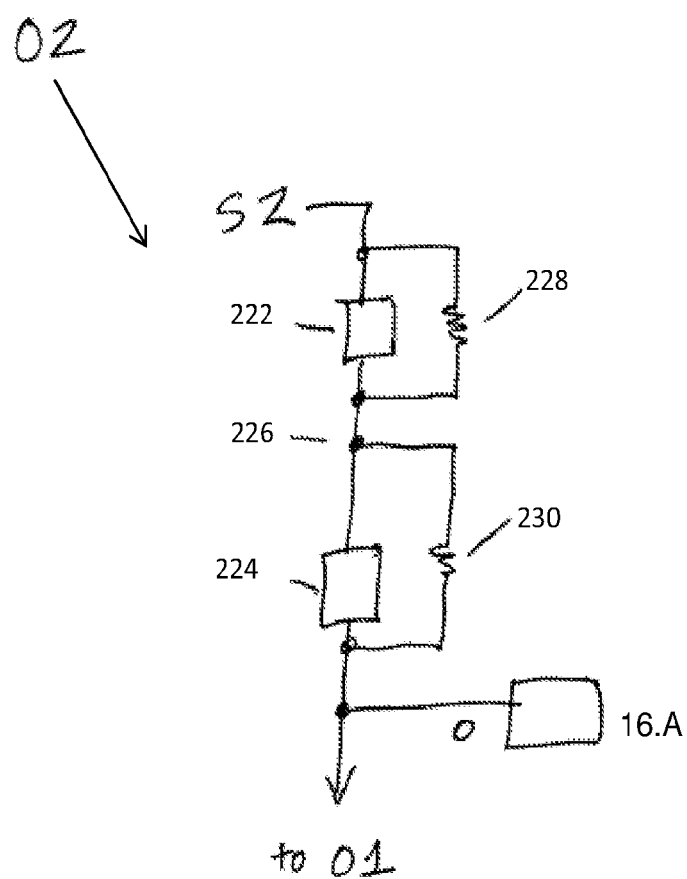
FIG. 22 shows a switch such as might be used in the switching circuitry of FIG. 21.

Referring now generally to the Figures and particularly to FIG. 22, in FIG. 21, each tri-state driver O1 and O2, P1 and P2, LL1 and LL2, P1 and P2 is controlled by control lines 51, the details of which are omitted for clarity in FIG. 21. As with any tri-state driver, it is important that at most one of the switches be "on" at a particular time. Stated differently, it should never happen that both switches are on at the same time. Thus, for example, it is preferable switches O2 and O1 should never be simultaneously "on".

The design challenge is that the power provided at the cathode wire S1 and the anode wire S2 externally to satellite controller 40 in may be as small as two volts. What's more, the design goal is that the satellite controller 40 should withstand as much as ten volts present at the cathode wire S1 and the anode wire S2. Likewise the designer must be prepared for the possibility that the potential difference between a particular electrode and either of S2 and S1 may again be as little as two volts or as much as ten volts.

In prior-art switching circuitry, a high-voltage PMOS transistor was employed in the current path from S2 to an electrode. Stated differently, in the portrayal of FIG. 21, each of switches 02, P2, L2, and F2 was, in the prior art, a high-voltage PMOS transistor.

The voltage threshold of the prior-art high-voltage PMOS transistor was typically about 1.6 to 1.7 volts. Experience showed, however, that it was not possible to count on the threshold being reached for this prior-art transistor. Instead, what would sometimes happen is that the transistor would fail to reach its threshold, would fail to conduct, and thus would fail to provide the desired connection between S2 and the respective electrode.

Referring now generally to the Figures and particularly to FIG. 22, FIG. 22 shows an exemplary switch O2 according to the invention. What is provided is a third PMOS transistor switch 222 and a fourth PMOS transistor switch 224 in series. Each of the third PMOS transistor 222 and the fourth PMOS transistor 224 has a threshold of about 0.9 volts. The control circuitry 52 turns on one of the third PMOS transistor switch 222 and the fourth PMOS transistor switch 224, and the third PMOS transistor switch 222 and the fourth PMOS transistor switch 224 conduct because the available input of at least two volts available at the node wire S2 is well over the voltage required (0.9 volts) to cause the switch to conduct, even with some impedances elsewhere in the circuit O2.

One of the switches third PMOS transistor switch 222, fourth PMOS transistor switch 224 having turned on, it supplies potential at second location 226 to the other of the switches third PMOS transistor switch 222, fourth PMOS transistor switch 224 and thus a control signal from the switch module 52 is able to provide gate potential to the other switch. Again the available voltage at the second location 226 is on the order of at least two volts, slightly less due to impedances elsewhere in the circuit, but in any event well over the 0.9 volts required to cause the switch to conduct.

In a steady state, after both the third PMOS transistor switch 222 and the fourth PMOS transistor switch 224 may be in an off state. A sixth resistor 228 is placed in parallel across the third PMOS transistor switch 222, and a seventh resistor 230 is placed in parallel across the fourth PMOS transistor switch 224. The sixth resistor 228 and the seventh resistor 230 balance a voltage drop when the switch 222 and the switch 224 are in the off state, i.e., when the third PMOS transistor switch 222 and the fourth PMOS transistor switch 224. The sixth resistor 228 and the seventh resistor 230 help to balance the voltage drop across the two switches, so that each of the third PMOS transistor switch 222 and the fourth PMOS transistor switch 224 shoulder about half of the burden, i.e., about half of the potential across the series of two switches. Both the third PMOS transistor switch 222 and the fourth PMOS transistor switch 224 are rated for as much as 5.5 volts, meaning that the third PMOS transistor switch 222 and the fourth PMOS transistor switch 224 in series can withstand about eleven volts. This satisfies the design goal of the switch O2 being able to withstand as much as ten volts across its switching terminals. In the circuit layout, it is preferable that the third PMOS transistor switch 222 and the fourth PMOS transistor switch 224 be laid out with as close as possible a physical match.

What is described, then, is a cascade of PMOS switches, e.g., the third PMOS transistor switch 222 and the fourth PMOS transistor switch 224 between the anode wire S2 and an electrode 16.A, 16.B, 16.C and 16.D.

The methods, systems and programming of the invention may be incorporated into a variety of different types of lead systems. Lead systems of interest include, but are not limited to, those described in: U.S. application Ser. Nos. 11/664,340; 11/731,786; 11/562,690; 12/037,851; 11/219,305; 11/793,904; 12/171,978; 11/909,786; the disclosures of which are herein incorporated by reference.

Aspects of the invention include methods of making a vascular lead electrode satellite 26, where the method includes providing an electrode support 11 as described above and positioning an electrode 16.A, 16.B, 16.C and 16.D in a recess of the support 11, and in certain aspects additionally includes placing an integrated circuit 6 and 10 in the support 11 such that the integrated circuit 6 and 10 is electrically coupled to the electrode element(s) 16.A, 16.B, 16.C and 16.D in the recess(es) of the support 11. In certain aspects, the positioning step includes fitting a premade electrode into the recess, e.g., by sliding the electrode 16.A, 16.B, 16.C and 16.D into the recess. As such, a prefabricated electrode 16.A, 16.B, 16.C and 16.D, such as a petal electrode as described in PCT/US2005/46811 titled "Implantable Addressable Segmented Electrodes" filed on Dec. 22, 2005, may be slid into the recess to produce the desired electrode structure. In certain aspects, the methods include producing electrodes 16.A, 16.B, 16.C and 16.D in recesses of the support 11, e.g., via a deposition protocol, such as cathodic arc deposition. Further descriptions of methods of producing electrode assemblies are provided in provisional application Ser. No. 60/865,760 filed on Nov. 14, 2006, the disclosure of which is herein incorporated by reference.

Figure 23:
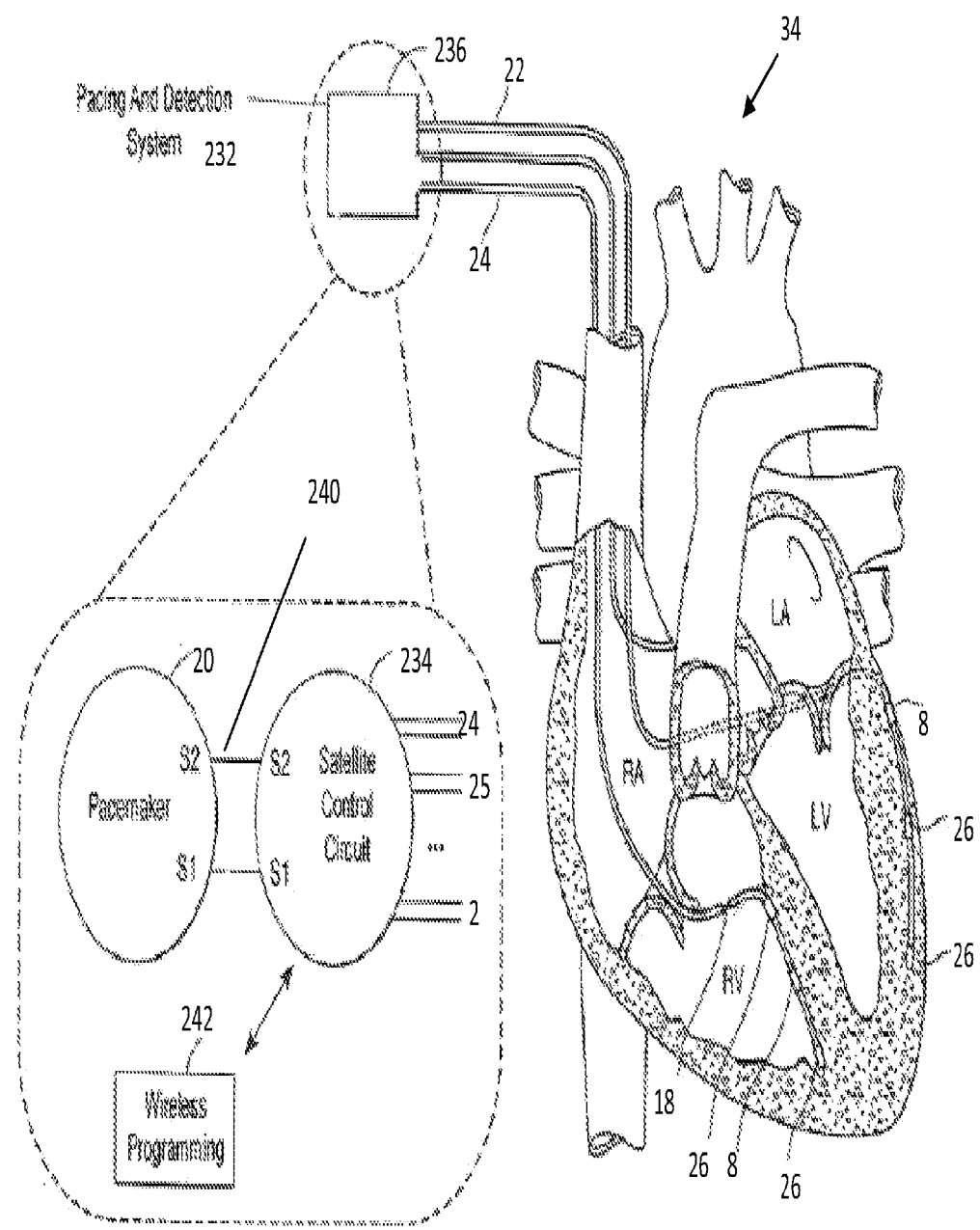
FIG. 23 illustrates the locations of a number of the satellites of FIG. 5 and incorporated in multi-electrode pacing leads of FIGS. 4 and 5, in accordance with an embodiment of the present invention.

Referring now generally to the Figures and particularly to FIG. 23, FIG. 23 is a high level schematic of a second cardiac pacing and signal detection system 232 in which a number of the satellites 26 are dispersed on one or more pacing leads 22, 24 and 25 and communicate with a satellite control circuit 238. The second cardiac pacing and signal detection system 232, or "second system" 232, provides a unified extra-cardiac communication and control element 236 for the overall system of FIG. 1, and may include, for example, a pacemaker 20, typically implanted under a patient's skin away from the heart 38. In the specific configuration shown, there are three pacing leads 22, 24 and 25, including the left ventricular lead 22 and the right ventricular lead 24.

The unified extra-cardiac communication and control element 236 is shown in an enlarged detail to be a distributed system, wherein multiplexing and switching capabilities are provided by the satellite control circuit 238 that augments the pacemaker 20, which may be any conventional pacemaker. The satellite control circuitry 238 includes at least one active device, and is typically includes an integrated circuit 10. In this case, referring now to FIG. 24, a satellite control circuit 238 is an active device comprised within the satellite control circuitry 236. The satellite control circuit 238 is coupled to a system bus 240, and thus interfaces with the pacemaker 20. The satellite control circuit 238 acts as an interface between the pacemaker 20 and a plurality of leads 22, 24 and 25, ranging from about 1-10 leads, such as from about 4-7 leads, including about 5 leads. The arrangement described above with respect to leads 22, 24 and 25 is essentially representative.

Satellite control circuit 238 is electrically coupled to pacemaker 20 via the cathode wire S1 and the anode wire S2 of the system interface 240, wherein the cathode wire S1 may be applied as an electrical ground and anode wire S2 may be applied as a power supply feed. The cathode wire S1 and the anode wire S2 may be configured at the pacemaker end and separately include connectors 32.D which can be plugged into standard pacemaker lead plug receptors.

The second system 232 may be configured to perform a number of functions. The precise division of labor between satellite control circuit 238 and pacemaker 20 can be a matter of design choice. To the extent that it is desired to implement embodiments of the present invention, the pacemaker 20 can be considered to provide a supply of power from the source potentiometer 158 to the plurality of leads 22, 24 and 25 and the ability to generate pacing pulses 160 of desired voltage and duration. It id understood that the pacemaker 20 and the satellite control circuit 238, along with a wireless programming module 242 can be implemented within the single housing unified extra-cardiac communication and control element 236.

In short, the satellite control circuit 238 multiplexes the pacemaker signals among the various leads, although some signals may go to multiple leads 22, 24 and 25. The switching circuit also sends signals to, and receives signals from, the satellites on the bus. Additionally, the control circuit 238 provides a communication link to external devices via the, such as the wireless programming module 242, which can remotely control and program the switching circuit with operating or functional parameters, certain parameters of which can then be communicated to pacemaker 20 by the switching circuit. The switching circuit gets its power from pacemaker 20, but could be provided with the separate battery 12 if desired.

Each satellite 26 may also contain the satellite control circuit 238 as, or comprised within, a satellite controller 40 which communicates with the unified extra-cardiac communication and control element 236 and receives configuration signals via the cathode wire S1 and/or the anode wire S2 that determine which of the separately coupled four electrodes 16.A, 16.B, 16.C and 16.D are to be coupled to the cathode wire S1 and/or the anode wire S2. In particular, the configuration signals, the subsequent pacing pulse signals 160, and the analog signals collected by the electrodes 16.A, 16.B, 16.C and 16.D can all be communicated through the cathode wire S1 and the anode wire S2, in either direction. The various quadrant arrangements of electrodes 16.A, 16.B, 16.C and 16.D allows administering pacing current via electrodes 16.A, 16.B, 16.C and 16.D oriented at a preferred direction, for example, away from nerves, or facing an electrode 16.A, 16.B, 16.C and 16.D configured to sink the current of the pacing pulse 160. Such precise pacing allows low-power pacing and minimal tissue damage caused by the pacing pulse 160.

Figure 24:
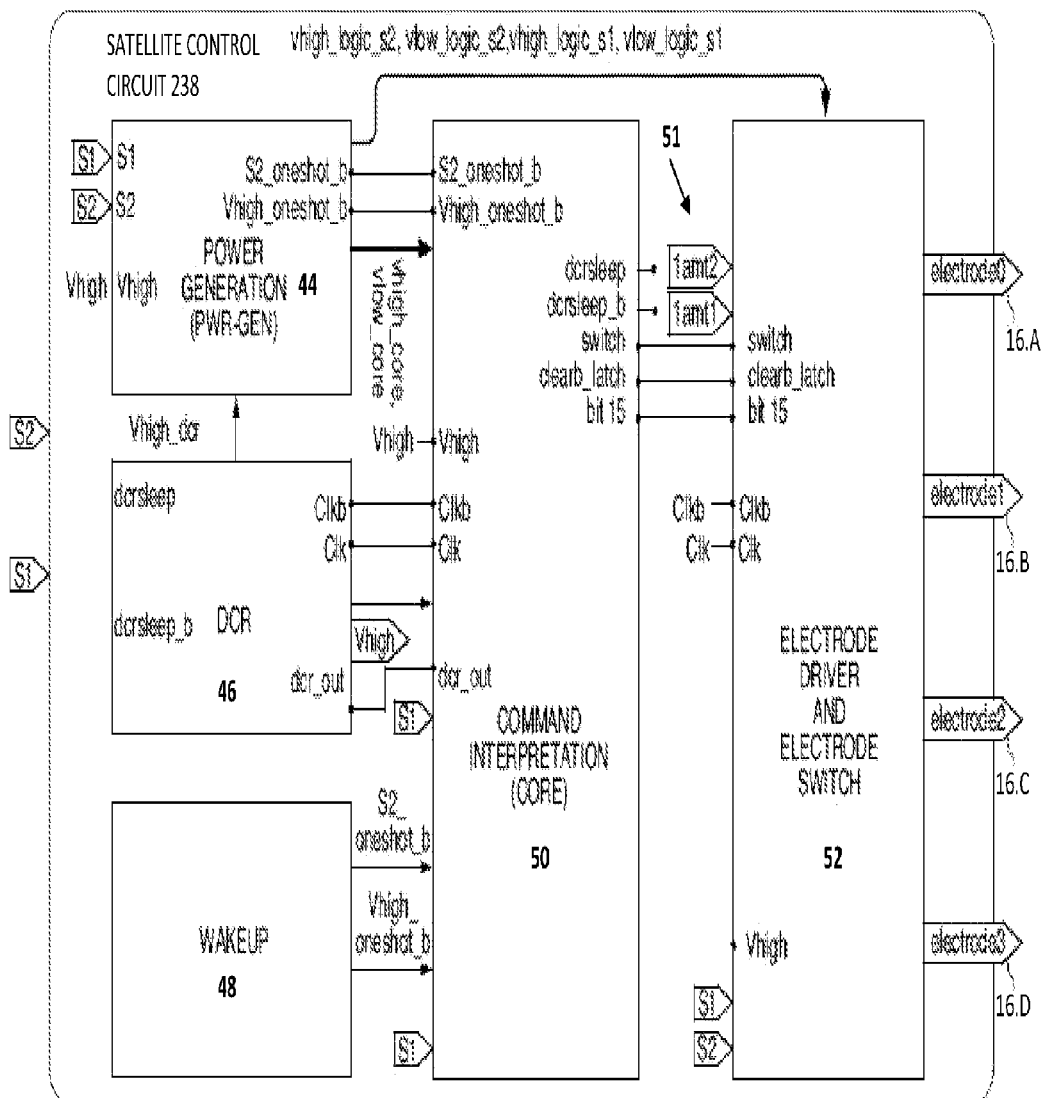
FIG. 24 illustrates a high level block diagram for circuitry within a satellite control circuit on a multi-satellite lead of FIG. 4, in accordance with an embodiment of the present invention.

Referring now generally to the Figures and particularly to FIG. 24, FIG. 24 is a high-level block diagram of the satellite control circuit 238 as configured on a lead 22, 24 and 25, in accordance with an aspect of the present invention. The satellite control circuit 238 comprises the power generation ("PWR-GEN") module 44, the data-clock recovery ("DCR") module 46, the wake-up ("WAKEUP") module 48, a command interpretation ("CORE") module 50, and an electrode driver and electrode switch module 52 which is coupled to four electrodes 16.A, 16.B, 16.C and 16.D. The satellite control circuit 238 is not limited to these particular circuits, or one control circuit and may be a distributed system with any number of circuits.

The PWR-GEN module 44 generates the power-supply voltages for CORE module 50 and electrode driver and electrode switch module 52. The PWR-GEN module 44 derives initialization signals "s2_oneshot_b" and "vhigh_oneshot_b" from the voltage across bus conduction paths of the cathode wire S1 and the anode wire S2. These initialization signals are asserted when "Vs2" and signal "vhigh" rise above their respective predetermined voltage thresholds. This supply voltage is used to operate the digital circuits in the satellite chip. Specifically, PWR-GEN module 44 provides two voltages, vhigh_core and vlow_core, to command interpretation module 50.

The command interpretation module 50 receives the bits in digital data signal "dcr_out" from DCR module 46 and maps these bits to control commands. Based on these control commands, the command interpretation module 50 generates control signals designated "switch" for effectuating the configurations specified for the electrodes 16.A, 16.B, 16.C and 16.D, "clearb_latch" for clearing the registers storing the configurations of the electrodes 16.A, 16.B, 16.C and 16.D electrode driver and switch module 52, and "dcrsleep" and "dcrsleep_b" for turning off DCR module 46.

The DCR module 46 provides the correct clock signals recovered from signals carried on the cathode wire S1 and the anode wire S2 to the rest of digital circuitry within control chip 100. DCR module 46 also recovers the data signals carried on the cathode wire S1 and the anode wire S2 into a digital format that can be used by command interpretation module 50. DCR module 46 also receives complementary sleep signals from initialization generation and wake-up module 48 which turn off and on DCR module 46 respectively, such as configuration phases or pacing phases and send those signals to command interpretation module 50 to turn on or turn off satellite control circuit 238 or to turn on or turn off electrodes 16.A, 16.B, 16.C and 16.D The electrode driver and electrode switch module 52 then selects and switches the electrodes 16.A, 16.B, 16.C and 16.D, as configured, so that the desired electrodes 16.A, 16.B, 16.C and 16.D can couple to the cathode wire S1 or the anode wire S2 for pacing and/or signal-detection purposes. During configuration, the satellite control circuit 238 sends configuration signals to specify which satellite or satellites to activate and which electrode on each activated satellite to are to be coupled to which bus conduction path, such as the cathode wire S1 or the anode wire S2.

Figure 25A:
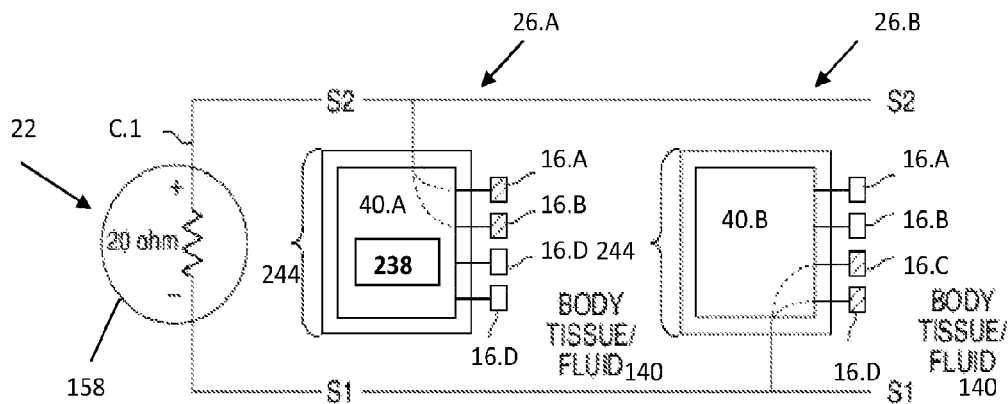
FIG. 25A is a block diagram illustrating a circuit formed by four electrodes of FIG. 5 as configured by the satellite control circuit, in accordance with an embodiment of the present invention.

Referring now generally to the Figures and particularly to FIG. 25A, FIG. 25A is a block diagram illustrating a first impedance circuit C.1 formed 238 in electrical combination of the second system 232 with the target body 140, wherein the four electrodes 16.A, 16.B, 16.C and 16.D of the first electrode group EG.1 of the distal satellite 26.A as configured by the satellite control circuit 238. The satellite control circuit 238 may comprise, or be comprised within, the distal satellite controller 40.A of FIGS. 16 and 17, in accordance with an aspect of the present invention. It is understood that one or more additional satellites 26.B, 26.C and 26.D may comprise a separate satellite control circuit 238.

Each satellite control circuit 238 is electrically coupled to the unified extra-cardiac communication and control element 236 via the cathode wire S1 and the anode wire S2, wherein the cathode wire S1 represents ground and the anode wire S2 represents a power supply. Vsource 242 is the source voltage supplied by the source potentiometer 158 and Vcircuit 244 is the actual voltage delivered to the electrodes 16.A, 16.B, 16.C and 16.D and the control circuit. It is understood that the value of Vcircuit 244 depends on the value of (a.) Vsource 242, (b.) the internal impedance 246 contribution of the second system 232 (or "internal impedance"), and (c.) the external impedance 248. The anode wire S2 is coupled to the first electrode 16.A and the second electrode 16.B, which are shaded in the FIG. 25A. Note that although distal satellite 26.A contains four electrodes 16.A, 16.B, 16.C and 16.D, only the first electrode 16.A and the second electrode 16.B of the first electrode group EG.1 are coupled to the anode wire S2. The third electrode 16.C and the fourth electrode 16.D of the first electrode group EG.1 are simultaneously turned off.

The cathode wire S1 is the ground line for the first lead 22 and is coupled to the third electrode 16.C and the fourth electrode 16.D, which are also shaded in FIG. 25A, of the second electrode group EG.2 of the second satellite 26.B. As demonstrated in FIG. 25A, all electrodes 16.A, 16.B, 16.C and 16.D are surrounded by body tissue of the target body 140. It is understood that contact resistance between the electrodes 16.A, 16.B, 16.C and 16.D and the target body 140 may contribute to the impedance that is external to the electrodes 16.A, 16.B, 16.C and 16.D.

Figure 25B:
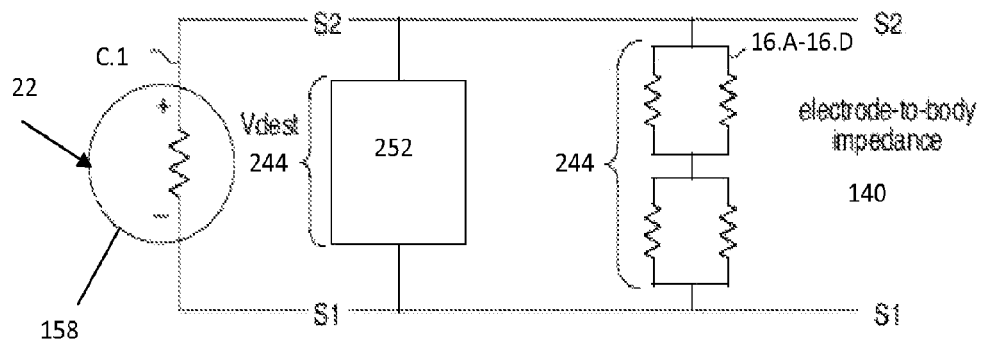
FIG. 25B is an equivalent circuit for the electrode configuration illustrated in FIG. 25A, in accordance with an embodiment of the present invention.

Referring now generally to the Figures and particularly to FIG. 25B, FIG. 25B is a second impedance circuit diagram of the first impedance circuit C.1 illustrated in FIG. 25A, in accordance with another aspect of the present invention. In the first electrode pacing configuration C.1 as shown in FIG. 25A, the first electrode 16.A and the second electrode 16.B of the first electrode group EG.1 of the distal first satellite 26.A are coupled to the cathode wire S2 and the third electrode 16.C and the fourth electrode 16.D from the second satellite 26.B are coupled to the anode wire S1. The Vcircuit 244 for this circuit depends on a value of Vsource 242, the internal impedance 246 and the external impedance 248. Where Zelec 250 is per-electrode-to-body impedance (part of the external load impedance), the external impedance contribution $Z_o$ attributable to the electrodes 16.A, 16.B, 16.C and 16.D, $Z_o$, would be:

$$Z_o = 2*Z_{elec}/2 = Z_{elec}$$

The external impedance 248 is further reduced by the impedance of a summed impedance 252 of current pathways passing through the distal satellite controller 40.A, the second satellite controller 40.B, which is coupled between the cathode wire S2 and the anode wire S1 and with the first electrode 16.A and the second electrode 16.B of the first electrode group EG.1 and the third electrode 16.C and the fourth electrode 16.D of the second electrode group EG.2. As stated above, different electrode configurations will produce different an external impedance 248. Consequently, Vcircuit 244 can vary with different electrode configurations. Furthermore, as shown below, FIG. 25C is just one example of how a change in electrode configuration can change Vcircuit 244 dramatically.

Figure 25C:
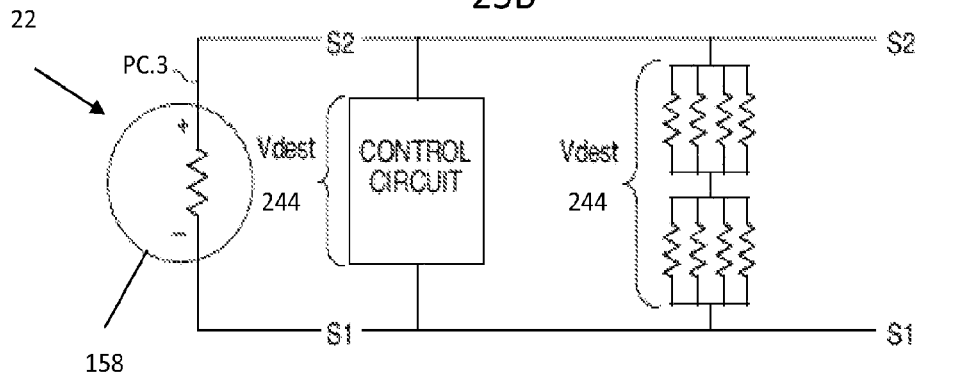
FIG. 25C is an equivalent circuit for a pacing circuit wherein four electrodes FIG. 5 are coupled to a power source of FIG. 17, in accordance with an embodiment of the present invention.

FIG. 25C is a third impedance circuit diagram for a second pacing circuit C.2 wherein four electrodes 16.A, 16.B, 16.C and 16.D of one satellite 26 are coupled to the anode wire S2 and four electrodes 16.A, 16.B, 16.C and 16.D of another satellite are coupled to the cathode wire S1, in accordance with an aspect of the present invention. In the electrode configuration set forth in FIG. 25C, all four electrodes 16.A, 16.B, 16.C and 16.D from first satellite 26.A are coupled to the anode wire S2 and all four electrodes 16.A, 16.B, 16.C and 16.D from the second satellite 26.B are coupled to the cathode wire S1. The Vcircuit 244 for this circuit C.1 depends on the value of Vsource 246, the internal impedance 246 and the external impedance 248. The external impedance attributable to the electrodes 16.A, 16.B, 16.C and 16.D would be:

$$Z_o = 2*Z_{elec}/4 = 0.5 Z_{elec}$$

Hence, the Vcircuit 244 in FIG. 25C is approximately one half of the Vcircuit 244 in FIG. 25B. The above Figures and equations illustrate just two configurations of connection patterns of the electrodes 16.A, 16.B, 16.C and 16.D of the satellites 26 of the leads 22, 24, and 25 of the second system 232. The number of differing electrode configurations is considerable.

Accordingly, different electrode configurations may result in a different external impedance 248 in any circuit loop that includes the target body 140 and the second system 232, which results in unpredictable voltage supplied to the implanted satellite controllers 40 and the satellite control circuits 238. When the voltage supplied to the satellite controller 40 is unpredictable, the satellite controller 40 may malfunction.

Uncertain external impedance 248 in the circuit due to electrodes 16.A, 16.B, 16.C and 16.D coupled to the cathode wire S1 or the anode wire S2 can lead to many issues. For example, if Vsource 246=5V, internal resistance 246 is $Z_{internal}=20\Omega$ and the external impedance 248 $Z_{internal}=200\Omega$, then the equation becomes:

$$V\text{circuit } 244 = 5V*200\Omega/(200\Omega+20\Omega) = 4.5V$$

This reduced voltage supplied to the satellite controller 40 could result in many problems. For example, even a small voltage change due to a number of variables can disrupt satellite control circuit 238 significantly and leave doctors and patients with undeterministic results. A change as small as, for example 1-2V, bringing the 4V voltage down to 3-2V is enough to cause unpredictable results.

For instance, during the configuration phase, the command interpretation module 50 may not have sufficient voltage to configure the electrodes 16.A, 16.B, 16.C and 16.D properly. Another issue is that the switching transistors in the circuits of the second system 232 may not have sufficient voltage to couple or decouple the electrodes 16.A, 16.B, 16.C and 16.D to the to the cathode wire S1 and the anode wire S1, thus it is unknown if they will change from one state to another, causing various switch circuits 52.A-52.N, 72, 196, 206, to be constantly on or constantly off. Consequently, there could be leakage current through the electrodes 16.A, 16.B, 16.C and 16.D when the electrodes 16.A, 16.B, 16.C and 16.D are meant to be decoupled from the source potentiometer 158, or extra impedance in the circuit electrodes 16.A, 16.B, 16.C and 16.D that are meant to be coupled to the source potentiometer 158. Thus, an unknown state can produce current leakage and insufficient pacing voltage.

Figure 26:
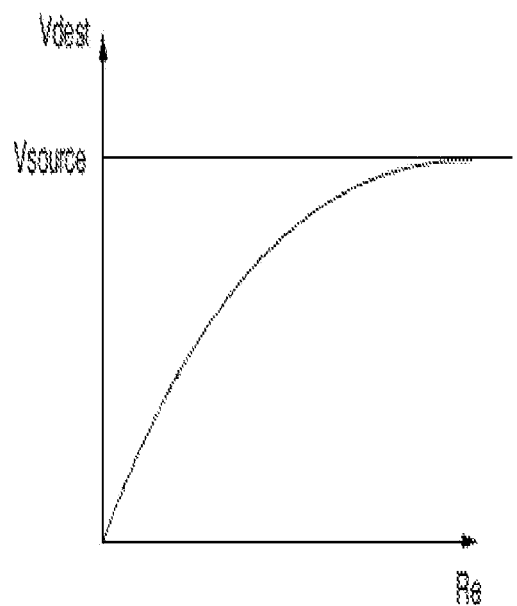
FIG. 26 is a graph showing an exemplary relation between voltage and the external impedance of a closed control/pacing circuit of FIGS. 25A, 25B and 25C.

Referring now to FIG. 26, FIG. 26 is a graph showing an exemplary relation between Vcircuit 244 and the external impedance 248 of a closed control/pacing circuit. The equation set forth above and below is the basis for the graph in FIG. 26. The equations states that the voltage supplied to the satellite control circuit 238 and pacing electrodes 16.A, 16.B, 16.C and 16.D is determined by the external impedance 248 and the internal impedance of the circuit, $$V\text{circuit } 244 = V\text{source } 246 * Z_{external}/(Z_{external} + Z_{internal})$$

As seen in the graph of FIG. 26, given a source voltage, Vsource 246, when the external impedance 248 increases, the external voltage Vcircuit 244, also increases. When the external impedance 248 is sufficiently large and the internal impedance 246 becomes negligible, the external voltage Vcircuit 244 becomes substantially similar to Vsource 242. Thus, when the electrodes 16.A, 16.B, 16.C and 16.D are reconfigured, the voltage supplied to the satellite control circuit 238 could drop significantly, the second system 232 could malfunction and/or fail.

To achieve the formation of a closed circuit through the electrodes 16.A, 16.B, 16.C and 16.D during the configuration phase, the method the present invention optionally provides for isolation of one, many, or all electrodes 16.A, 16.B, 16.C and 16.D from the source potentiometer 158 during a configuration phase. Decoupling all electrodes 16.A, 16.B, 16.C and 16.D from the power source 158 during the configuration phase ensures that the source voltage is supplied only or primarily to the satellite control circuit 238. By decoupling all electrodes 16.A, 16.B, 16.C and 16.D during configuration of satellite control circuit 238, the external impedance 248 is stable, and the voltage supplied to the satellite control circuit 238 is stable for configuration. After configuration, the selected electrodes 16.A, 16.B, 16.C and 16.D may be turned on and coupled to the cathode wire S2 and the anode wire S2, so that the source voltage, Vsource 246, which is now used for pacing, is delivered to the electrodes 16.A, 16.B, 16.C and 16.D.

This provides a stable external impedance 248 to the first lead 22 without additional complex circuitry. Due to the extremely small nature of the first lead 22, even slight additions in circuitry would not be able to fit. For example, some integrated circuits 10 may range from 0.01 mm$^2$-1 mm$^2$, such as from 0.1 mm$^2$-0.5 mm$^2$, including about 0.1 mm$^2$. In addition, the external impedance 248 stabilizer produces stable impedance without a temperature change to the human tissue and without changing the composition of human tissue.

Referring now generally to the Figures and particularly to FIG. 24, in one aspect, the DCR module 46 derives and recovers complementary clock signals "clk" and "clkb", and a digital data signal "dcr_out" from the voltage across the conduction paths provided by The cathode wire S1 and the anode wire S2. A signal "dcr_out" is a digital signal using 0 volts and voltage "vhigh" to encode logic states of the output bits. The DCR module 46 also receives complementary sleep signals "dcrsleep" and "dcrsleep_b," which turn off DCR module 46 at times when there are no data or clock signals that need to be recovered from the bus, such as during pacing and signal collection phases, or when the satellite has determined that it is not being addressed by digital signals on the bus.

At the beginning of the pacing phase, the DCR module 46 receives complementary sleep signals "dcrsleep" and "dcrsleep_b," to turn off all data, clock signals. At the same time, the selected electrodes 16.A, 16.B, 16.C and 16.D are turned on to facilitate the subsequent pacing. However, during the configuration phase, the electrodes 16.A, 16.B, 16.C and 16.D are temporarily decoupled from the cathode wire S1 and the anode wire S2 so that sufficient voltage is delivered to the satellite control circuit 238.

The command interpretation module 50 receives the bits in digital data signal "dcr_out" from the DCR module 46 and maps these bits to control commands. Based on these control commands, it generates control signals designated "switch" for effectuating the configurations specified for the electrodes 16.A, 16.B, 16.C and 16.D, "clearb_latch" for clearing the registers storing the configurations of the electrodes 16.A, 16.B, 16.C and 16.D in electrode driver and switch circuit 108, and "dcrsleep" and "dcrsleep_b" for turning off DCR module 46. In one aspect, when signal "s2_oneshot_b" is asserted, command interpretation circuit 106 de-asserts signal "dcrsleep" to wake up DCR module 46. When "vhigh_oneshot_b" is asserted, command interpretation module 50 asserts signal "clearb_latch" to reset the configuration of the electrodes 16.A, 16.B, 16.C and 16.D.

Command interpretation module 50 receives control signals "switch," "clearb_latch," and "bit15" from signals "iamit1" and "iamit2" from electrode driver and switch module 52, and uses these control signals to identify and configure the electrodes 16.A, 16.B, 16.C and 16.D. In the present invention, command interpretation module 50 issues a command to turn off all electrodes 16.A, 16.B, 16.C and 16.D. Command interpretation module 50 then receives a control signal to initiate a configuration phase.

The unique environment of an in-body computing system raises never-before-known challenges. According to alternate aspects of the method of the present invention, a provided method of external impedance stabilization allows for new devices, and improvements to known devices which would otherwise not be possible, such as muscle stimulators and tissue regeneration devices.

The invented external impedance stabilization process may include two stages: an instruction signal and a decoupling function. An instruction signal informs an in-body computing system when to decouple body tissue from the circuitry. The instruction signal may be an analog square wave, other analog waves, digital waves, and/or software instructions, among others. The instruction signal may also be modulated via amplitude modulation or frequency modulation, among others. The source of the instruction signal may be from inside or outside the body, e.g. an implanted second system 232 or the wireless device 142. Furthermore, the instruction signal may be programmed into a programmable device 242 (e.g. the integrated circuit 10, a cell phone, computer, etc.).

The decoupling function decouples body tissue of the target body 140 from the circuitry in an in-body computing system, e.g., the second 232. The decoupling function may be performed by a transistor switch, analog and digital switches, organic switches, and/or MEM switches, among others.

A stable external impedance 248, provided by certain aspects of the method of the present invention, is important for proper circuit operation. Stable impedances allow for constant power consumption and minimal voltage swings. Furthermore, certain aspects of the method of the present invention enable external impedance stabilization in a large range of varying external impedance without changing the temperature, without adding complex circuitry, and without altering the composition of the surrounding body tissue.

An important benefit of external impedance stabilization is the application of a stable external voltage Vsource 244. The external voltage Vsource 244 is a function of a voltage source (e.g. the battery 12, pacemaker 20, lead lines L1 and L2, other sources, or any combination thereof, etc.), the external impedance 248, and the internal impedance 246. In other words:

$$V_{external} = V\text{source } 246 * Z_{external}/(Z_{external} + Z_{internal})$$

Where:

$V_{external}$ is the external voltage (e.g. the voltage across the external impedance);

Vsource 246 is the voltage provided by a source (e.g. the voltage of a battery 12, pacemaker 20, lead lines L1 and L2, other sources, or any combination thereof, etc.);

$Z_{external}$ is the external impedance 248 (e.g. all impedances which are not internal impedance); and $Z_{internal}$ is the internal impedance 246 (e.g. the impedance of all the voltage sources and the cathode wire S1 and the anode wire S2).

Since the voltage source potentiometer 160 and the internal impedance 246 are usually stable, the external voltage Vcircuit 244 is primarily a function of the external impedance 248. As a result, a stable external impedance 248 provides a stable external voltage Vcircuit 244.

A stable external voltage Vcircuit 244 is particularly beneficial because an in-body computing system, e.g., the second system 232, will no longer have to tolerate a "voltage swing." A voltage swing occurs when the voltage supplied to an external component "swings" from its acceptable voltage to a lower or higher voltage. If the voltage swings too low, the circuitry in an in-body computing system may not properly function due to a lack of voltage. If the voltage swings too high, the circuitry in an in-body computing system may physically deteriorate due to heat, among other problems. By stabilizing the external impedance 248, external impedance stabilization also protects the circuitry in an in-body computing system from voltage swings.

External impedance stabilization also stabilizes power consumption. The power consumed by the circuitry in an in-body computing system is a function of the external impedance 248 and the square of the external voltage Vcircuit 244. In other words:

$$P_{external} = (V_{external})^2 / Z_{external}$$

Where:

$P_{external}$ is the external power consumed (e.g. the power consumed across the external impedance 248);

$V_{external}$ is the external voltage (e.g. the voltage across the external impedance 248); and $Z_{external}$ is the external impedance 248 (e.g. all impedances which are not internal impedance).

Since external impedance stabilization stabilizes the external impedance 248 and consequently the external voltage Vsource 242, the external power consumed is also stabilized. By stabilizing the external power consumed, external impedance stabilization protects the circuitry in an in-body computing system from consuming too much or too little power. If the circuitry in an in-body computing system consumes too much power, the life of the voltage source (e.g. the battery 12, pacemaker 20, lead lines L1 and L2, other sources, or other combinations thereof, etc.) may be significantly shortened. Voltage source life can be critical in small systems such as in an in-body computing system. If the circuitry in an in-body computing system consumes too little power, the circuitry may not function properly due to insufficient power.

External impedance stabilization can stabilize the voltage, via stabilizing the impedance, without additional complex circuitry. In an in-body computing system, chip area space is typically a crucial consideration when developing circuitry. This is due to the very small environment in which an in-body computing system must operate. As mentioned above, power consumption is a crucial consideration when developing circuitry in an in-body computing system. This is due to the lack of a long-lasting voltage source inside the target body 140. Any additional circuitry not only consumes more chip space, but also needs more power to perform logic and operate. The invented method of external impedance stabilization does not require any additional complex circuitry, and is beneficial to help lower chip area space and power consumption.

External impedance stabilization can stabilize both real and imaginary components of the external impedance 248. The external impedance 248 in an in-body computing system may come from body tissues, which have real and imaginary impedance components.

Impedance, in general, can be expressed as:

$$Z = R + jX$$

Where:

Z is the impedance;

R is the resistance (e.g. the "real" component of impedance);

jX is the "imaginary" component of impedance, where:

j is the square root of negative 1 (e.g. $\sqrt{-1}$); and

X is the reactance.

Each of the components may individually have a significant affect on the total impedance. Stabilizing one component may not be sufficient to stabilize the total impedance. The invented external impedance stabilizer decouples all real and imaginary impedances due to body tissue from the voltage source. Thus, the invented external impedance stabilizer can more fully stabilize the external impedance 248, and protect the circuitry in an in-body computing system from voltage swing and variations in power consumption.

The invented external impedance stabilizer can safely stabilize the external impedance 248 without changing the composition of the body tissue, which requires doping. Doping body tissue with hydrogen atoms, electrons, and/or other materials may cause great harm to the body tissue. For example, a sudden increase in hydrogen ions in the blood may lead to dangerous pH levels. By decoupling body tissues from in-body computing system, the invented external impedance stabilizer does not alter the composition of the body tissue while providing stable external impedances.

External impedance stabilization can stabilize a wide range of impedances. Body tissue impedances can vary greatly. On one extreme is bone and ligament which have very high impedances. On the other extreme are blood and other body fluids which have much lower impedances. The range of impedance variation is further increased if one or more tissues and fluids are combined (e.g. heart, then blood, then liver, etc.). Furthermore, the impedance of body tissues themselves may vary. For example, blood composition is altered after ingesting food or drinks (e.g. alcohol), and depending on the blood composition, the impedance of the blood can vary.

Furthermore, external impedance stabilization can work in a wide range of temperatures. The temperature of different parts of the target body 140 can vary. The temperature near the outer areas of the body (e.g. skin, eyes, nails, etc.) may be much lower than temperature near the inner areas of the body (e.g. heart, stomach, intestines, brain, etc.).

Additionally, external impedance stabilization can be applied to a wide variety of electrical contacts, such as electrodes 16.A, 16.B, 16.C and 16.D. In particular, in-body computing systems use a variety of electrical contacts, such as electrodes 16.A, 16.B, 16.C and 16.D, among others. Electrical contacts can vary with regard to composition and surface area. Depending on the composition and surface area, the impedance of the electrode can vary.

Regardless of which body tissue of the target body 140 is electrically in contact with the in-body computing system, certain aspects of the method of the present invention can stabilize the external impedance 248. The invented external impedance stabilizer can achieve this by decoupling some or all body tissue impedances of the target body 140 from the second system 232. Therefore, whether the in-body computing system is connected to blood, or whether it is connected to bone, the invented external impedance stabilizer can quickly and efficiently stabilize the real and imaginary components of the impedance without damaging or altering the surrounding body tissue.

To achieve the formation of a closed circuit through the electrodes 16.A, 16.B, 16.C and 16.D during the configuration phase, the invented external impedance stabilizer provides for isolation of all electrodes 16.A, 16.B, 16.C and 16.D from the power source 28 during the configuration phase. Decoupling all electrodes 16.A, 16.B, 16.C and 16.D from the source potentiometer 158 during the configuration phase ensures that the source voltage Vsource 242 is supplied only or primarily to one or more satellite control circuits 238. By decoupling all electrodes 16.A, 16.B, 16.C and 16.D during configuration of satellite control circuit 238, the external impedance is stable, and the voltage supplied to the satellite control circuit 238 is stable for configuration. After configuration, the selected electrodes 16.A, 16.B, 16.C and 16.D may be turned on and coupled to the cathode wire S1 and the anode wire S2, so that the source voltage, Vsource 246, which is now used for pacing, is delivered to the electrodes 16.A, 16.B, 16.C and 16.D.

This provides a stable external impedance to the first lead 22 without additional complex circuitry. Due to the extremely small nature of the first lead 22, even slight additions in circuitry would not be able to fit. For example, some integrated circuits 10 may range from 0.01 mm$^2$-1 mm$^2$, such as from 0.1 mm$^2$-0.5 mm$^2$, including about 0.1 mm$^2$. In addition, the invented external impedance stabilizer produces stable external impedance 248 without a temperature change to the human tissue and without changing the composition of human tissue.

The invented external impedance stabilizer can stabilize a very wide range of body tissue impedance of the target body 140. The target body impedance may vary greatly, ranging from about 10Ω-5000Ω, such as from about 100Ω-2500Ω, e.g. about 1500Ω. Furthermore, the temperature of the body tissue can affect the impedance of the body tissue. The body tissue temperature may vary, ranging from about 50°-110° F., such as about 75°-100° F., including about 98.6° F. Furthermore, the invented external impedance stabilizer can stabilize the impedance of a wide variety of electrical contacts (e.g. electrodes 16.A, 16.B, 16.C and 16.D). Electrical contacts have their own impedance, and may vary depending on a number of factors. These factors include chemical composition, and surface area, among others.

For example, the impedance of an electrical contact composed of pure platinum may be different than the impedance of an electrical contact composed of platinum with gold impurities.

The impedance of an electrical contact can also be quantified as a function of its surface area.

$$Z=I*p/A$$

Where:
Z=the impedance of the electrical contact;
I=the length of the electrical contact;
p=the resistivity of the electrical contact (e.g. chemical composition); and
A=the cross sectional area (e.g. surface area) of the electrical contact.

By accounting for the variations in length, chemical composition, and surface area, the invented external impedance stabilizer can stabilize the impedance of a wide variety of electrical contacts.

By stabilizing the external impedance 248, certain aspects of the method of the present invention can minimize the voltage swing in an in-body computing system and stabilize the voltage. The voltage swing of an in-body computing system may vary, and in some embodiments ranges from about 0.1V-10V, about 0.1V-4V, including about 3V.

The invented external impedance stabilizer may operate with a wide range of in-body computing system voltage sources. The voltage source may be a battery, chemical reaction, and/or bio sources, among others. The voltage source may vary, and in certain embodiments ranges from about 0.75V-12V, such as from about 1V-10V, including about 5V. With further miniaturization and advances in nanotechnology and biology, it is conceivable that voltage sources may become very small.

The invented external impedance stabilizer consists of two parts: an instruction signal and a decoupling function.

An instruction signal informs an in-body computing system when to decouple body tissue of the host body from the second system 232. The instruction signal may be an analog square wave, other analog wave, digital waves, and/or software instructions, among others.

In one embodiment, the instruction signal takes the form of an analog square wave. The analog square wave may range from a low of 3V to a peak of 5V, with a frequency of 1 MHz. However, depending on the necessities of an in-body computing system, this analog square wave may have very different wave characteristics. The low value in the analog square wave may range from about 0-3 V, such as from about 1 mV-1V, including about 500 mV. The high value in the analog square wave may range from about 3-15 V, such as from about 5-10 V, including about 7 V. The frequency may range from about 500 Hz-100 MHz, such as from about 100 kHz-50 MHz, including about 1 MHz. In in-body computing systems dealing with the heart, the frequency may range from about 10 kHz-100 MHz, such as from about 100 kHz-50 MHz, including about 1 MHz.

The instruction signal described above need not be a square wave or an analog wave. Furthermore, the instruction signal described above may be frequency modulated or amplitude modulated, or unmodulated. Depending on the specific requirements of an in-body computing system, the instruction signal may be a digital wave, or software instructions, among others. For example, instead of using peaks and troughs in an analog signal, an in-body computing system can use a stream of data (e.g. bytes). To illustrate, a sequence of "0 1 0 1 0 0" would be the digital equivalent of an analog wave characterized by "trough peak trough peak trough." This is but one example of an instruction signal. The number of variations is considerable.

Though an instruction signal may take many forms, an instruction signal must be a unique signal to an in-body computing system. This is so that an in-body computing system will not mistake a rogue signal for an instruction signal. For example, in one embodiment of the present invention, the external impedance stabilizer stabilizes the impedance in a multi-electrode lead system used for pacing, e.g., the second system 232. If the second system 232 mistook a signal for an instruction signal, a second system 232 would decouple the body tissue of the target body 140 from the circuitry and interrupt pacing prematurely.

An instruction signal may come from sources inside or outside the target body 140. In one aspect, the instruction signal comes from a pacemaker 20 in the second system 232. Other sources inside the target body 140 include batteries 12, implantable devices 3, 20 and 232, chemical reactions, and/or bio sources, among others. Sources outside the body include the wireless device 142, radio devices, cell phones, and/or computers, among others.

Sources of an instruction signal may use wires and/or radio frequency, among others, as a medium to convey an instruction signal to an in-body computing system.

An instruction signal may be sent at predetermined intervals or as needed. For example, it may be desirable to decouple the second system 232 from the target body 140 every week. In this case, the instruction signal may be preprogrammed onto an in-body computing system transmitter (e.g. the second system 232, pacemaker 20, cell phone, computer, etc.) to decouple every week.

In one embodiment of the present invention, an instruction signal is used to instruct the second system 232 when to decouple from the target body 140. It will be obvious to one skilled in the art that the instruction signal may also be used to instruct an in-body computing system when to couple to the body tissue.

A decoupling function may be a transistor switch, analog switches, digital switches, organic switches, and/or MEM switches, among others. A decoupling function may decouple one or more components of the second system 232 from the body tissue of the target body 140 simultaneously.

For example, in one aspect of the method of the present invention, the second system 232 is connected to the body tissue of the target body 140 via the electrodes 16.A, 16.B, 16.C and 16.D. The number of electrodes 16.A, 16.B, 16.C and 16.D may vary, ranging from about 1-500 electrodes, such as from about 20-100 electrodes, including about 64 electrodes. The decoupling function may decouple 1 electrode, or it may decouple all electrodes 16.A, 16.B, 16.C and 16.D, or it may decouple any number in between, depending on the instruction signal.

A decoupling function must be able to operate at a lower voltage than the voltage source. Before a decoupling function decouples an in-body computing system from the body tissue, a large voltage swing may exist in an in-body computing system. The voltage may be very low when a decoupling function decouples the body tissue.

For example, in one aspect of the method of the present invention, the voltage source may be 3V, and the voltage swing in the second system 232 may be 2V. In this case, the decoupling function would need to be able to operate at 1V. A transistor switch may be sufficient in this case, as many transistor switches can operate at very low voltages, ranging from about −2 V-7 V, such as from 0.5 V-5 V, such as from 0.75 V-2 V, including about 1V.

Furthermore, given the rapid development in nanotechnology and bioengineering, a MEMs switch, and/or organic switch, among others, may operate at sufficiently low voltages to tolerate the wide voltage swing in an in-body computing system.

In one aspect of the method of the present invention, a decoupling function is used to decouple the second system 232 from the body tissue. It will be obvious to one skilled in the art that the decoupling function may also be used to couple an in-body computing system to the body tissue.

Prior to the present invention, it was not known that the body tissue impedance would contribute to the impedance of an in-body computing system. Furthermore, it was not known that the impedance of the electrodes 16.A, 16.B, 16.C and 16.D themselves would contribute significantly to the external impedance. When building circuitry for an in-body computing systems, e.g., the second system 232, some of the present inventors discovered that the varying values of body tissue and electrode impedance contributed to the impedance of an in-body computing system. The varying value of body tissue and electrode impedance caused voltage swings in an in-body computing system, which ultimately resulted in malfunction.

Implanting multiple electrodes 16.A, 16.B, 16.C and 16.D gives rise to challenges associated with the body's relatively low electrical conductivity. Since the satellite control circuit 238 and the pacing electrodes 16.A, 16.B, 16.C and 16.D are typically coupled between the cathode lead wire S1 and the anode lead S2 in parallel, and the voltage applied to the satellite control circuit 238 and the pacing electrodes 16.A, 16.B, 16.C and 16.D is determined by the external impedance in relation with the internal impedance at the power source, the voltage supplied to the control logic and/or the pacing voltage supplied to the electrodes 16.A, 16.B, 16.C and 16.D may fluctuate depending on different electrode configurations.

In one aspect of the method of the present invention, a closed circuit can be formed from the source potentiometer 158, the cathode lead wire S1, the first electrode 16.A, the target body 140, the second electrode 16.B, the anode lead wire S2, and back to the source potentiometer 158. Meanwhile, the satellite control circuit 238 is also coupled between the two lead wires. The voltage supplied to the satellite control circuit 238, the first electrode 16.A, and the second electrode 16.B is determined by the internal impedance 246 and the impedances of (1.) the satellite control circuit 238, (2.) the first electrode 16.A, (3.) the second electrode 16.B and the target body 140 (e.g. all impedances which are not internal). In other words:

$$V\text{circuit } 244 = V\text{source } 246 * Z_{external}/(Z_{external} + Z_{internal})$$

Where:

Vcircuit 244 is the voltage supplied to the satellite control circuit 238 and pacing electrodes 16.A, 16.B, 16.C and 16.D;

$V_{source}$ is the voltage source (e.g. the voltage of a battery, pacemaker, lead lines, other sources, or any combination thereof, etc.);

$Z_{external}$ is the external impedance (e.g. all impedances which are not internal impedance); and $Z_{internal}$ is the internal impedance (e.g. the impedance of all the voltage sources 158, the cathode wire S1 and the anode wire S2).

Hence, the actual voltage supplied to the first electrode 16.A and the second electrode 16.B may be determined by the following factors: the patient's body tissue, the voltage of the power source (e.g., the battery 12, the pacemaker 20, other sources, or combinations thereof, etc.), the internal impedance 246, and the external impedance 248.

The resistance of the voltage supply may vary, and in certain embodiments ranges from about 0.1 nΩ-100Ω, such as from about 1 mΩ-50Ω, including about 20Ω. The resistance of the wires, e.g., Cathode wire S1 and the anode wire S2, may vary, and in certain embodiments ranges from about from about 0.1 nΩ-50Ω, such as from about 1 mΩ-20Ω, including about 10Ω.

Note that the external impedance may further depend upon the electrode construction, the number of electrodes 16.A, 16.B, 16.C and 16.D coupled to the body tissue, and the number of electrodes 16.A, 16.B, 16.C and 16.D. For example, the first electrode 16.A may be doped with hydrogen atoms, electrons, or other elements which would alter the first electrode's impedance.

The number of satellites 26 may vary, and in certain embodiments ranges from about one to two hundred satellites 26, about ten to one hundred satellites 26, including about thirty-two satellites 26. The satellites 26 may be configured in different combinations for different purposes which affects the external impedance. Each satellite 26 has a number of electrodes 16.A, 16.B, 16.C and 16.D. The number of electrodes 16.A, 16.B, 16.C and 16.D on each satellite 26 may vary, and in certain configurations ranges from about one to ten electrodes 16.A, 16.B, 16.C and 16.D, about three to eight electrodes 16.A, 16.B, 16.C and 16.D, including about four electrodes 16.A, 16.B, 16.C and 16.D.

Therefore, different electrode configurations may result in different external impedances and hence different voltages supplied to the satellite control circuit 238 and electrodes 16.A, 16.B, 16.C and 16.D.

Note that the satellite control circuit 238 which is used to configure the electrodes 16.A, 16.B, 16.C and 16.D is typically coupled between the cathode wire S1 and the anode wire S2. When the voltage supplied to the electrodes 16.A, 16.B, 16.C and 16.D varies so does the voltage supplied to the satellite control circuit 238. As a result, the satellite control circuit 238 may malfunction due to insufficient voltage with certain electrode configurations. When insufficient voltage is supplied to the switching transistors used to couple or decouple the electrodes 16.A, 16.B, 16.C and 16.D, these switching transistors may not be sufficiently turned on or turned off, resulting in leakage current and insufficient pacing voltage. Furthermore, when the external voltage Vcircuit 244 applied supplied varies, the power of consumed by the satellite 26 accordingly varies.

An invented fault recovery and detection system 254 for implantable devices provides an implantable device system design that achieves a lower device failure rate with component specific fault detection. The method of invented fault recovery and detection system 254 may be implemented by software encoded instructions stored on the computer-readable medium 32.E in combination with the pacemaker controller 54 and/or one or satellite controllers 40.

also provides for correction mechanisms which can be employed even when the fault is detected by alternative methods. One use of this invention is to avoid false shock to the patient or failure to shock the patient when it is necessary. Of course, the fault recovery and detection system 254 for implantable devices can be used in fault situations with other devices than automatic implantable defibrillators.

The primary features of this invention are fault recovery and fault detection. The fault recovery algorithm in the fault recovery and detection system 254 couples closely with detection algorithms, such as those provided by example, to provide faulty component replacement/reprogramming, normalization of sensors, and circuit fault correction. The fault detection algorithm in the fault recovery and detection system 254 focuses on creating a predictive profile 256 of component-based sensor sensitivity and electrode response.

The key to both features is the generation of the component profile 256 and the use of that component profile 256.

Figure 27:
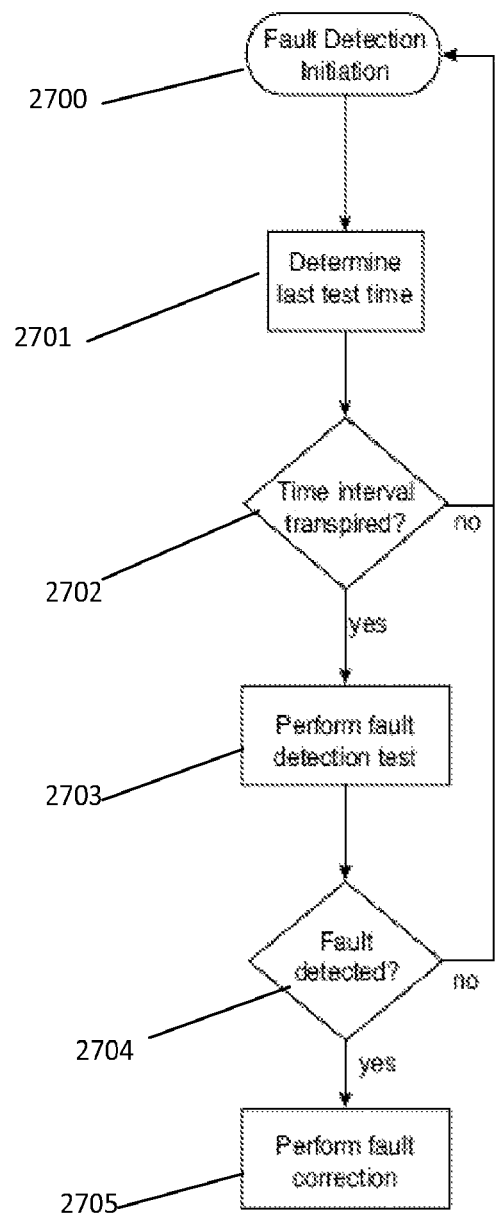
FIG. 27 is a flow chart of an embodiment of the present invention where the fault detection algorithm and fault recovery algorithm work together.

Referring now generally to the Figures and particularly to FIG. 27, FIG. 27 shows a flow chart illustrating an aspect of the method of the present invention wherein a fault detection algorithm and the fault recovery algorithm may work together in certain embodiments of the invention.

The two algorithms can work together synergistically in a variety of designs. The fault detection algorithm in the invented fault recovery and detection system 254 can give a complex profile of the fault location and deterioration rate of elements of the second system 232. The fault recovery algorithm in the present invention may be designed to save computation time and trial-and-error time using the complex profile to accurately correct faults.

In step 2700 a fault detection process is initiated by the second system 232. The satellite controller 238 of the unified extra-cardiac communication and control element 236 of FIG. 23 determines a last test time of the first device 34 in step 2701. The satellite controller 238 of then determines the length of time that has passed between the current time and the last test time in step 2702, and proceeds onto step 2703 when a predetermined interval time T1 since a last system test has been exceeded.

The second system 252 then initiates a fault detection test in step 2704 of the first device 34 in step 2703, and determines in step 2704 whether a new fault in the first device 34 has been detected. When the second system 34 determines in step 2704 that a new fault has been detected, the second system 232 proceeds onto step 2705 and to perform a fault correction.

When implementing and selecting particular embodiments of the fault recovery and detection system 254 for implantable devices, the complexity, cost, energy consumption and size of the embodiment are balanced. Methods of detection can range between a plain and simple clinical guesswork to a highly component-specific fault detection algorithm. Methods of fault recovery can range between trial-and-error fixes to component specific fixes. The higher complexity of a particular algorithm usually means the need for higher energy consumption, higher cost and more additional space in implantable devices.

Usually, the complexities of the two algorithms in the fault recovery and detection system 254 are inversely proportional. Typically, a highly complex fault recovery algorithm needs a plain and simple fault detection algorithm. This is because the complex fault recovery algorithm might deploy trial-and-error fixes when little information is known about where the fault is. If the fault detection algorithm is highly specific, then the fault recovery algorithm can be simple and efficient. With detail knowledge of where the fault has occurred and where functional replacement components are, the fault recovery algorithm will be able to quickly pin point the fault and find a proper replacement.

Figure 28:
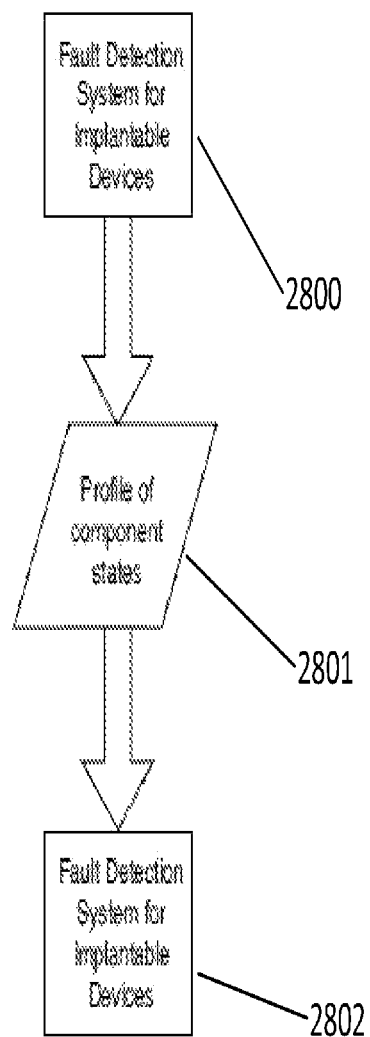
FIG. 28 is an illustration of a high level view of an invented fault detection process that can be implemented by the process of FIG. 27.

Referring now generally to the Figures and particularly to FIG. 28, FIG. 28 is an illustration of a high level view of the invented fault detection process. In step 2800 the invented fault detection system 254 initiates the process of FIG. 27. In step 2801 the invented fault detection system 254 accesses a profile of states of components of the first device 34, such as the electrodes 16.A, 16.B, 16.C and 16.D, the plurality of satellites 26, and the plurality of leads 24, 25 and 26. The profile of component states maintained by the invented fault detection system 254 is updated in step 2801 in accordance with the determinations mad in the most recent execution of step 2703. The invented fault detection system 254 proceeds from step 2801 to step 2802 and to continue periodic monitoring of the second system 232.

Referring now generally to the Figures and particularly to FIG. 29, FIG. 29 shows an example of component status profile 256 used by the invented fault recovery and detection system 254. The left columns 258 illustrate examples of what types of components may be tested and corrected under the algorithms herein. The right columns 260 illustrate the possible information to be stored in the component status profiles.

The fault recovery algorithm of FIGS. 27 and 28 of the fault recovery and detection system 254 increases the probability of a successful fault correction.

Different embodiments of the fault recovery and detection system 254 may provide features including capability of signal re-programming for failed electrodes 16.A, 16.B, 16.C, and 16.D, virtual component replacement through component re-selection, weighted selection of component replacement based on weighted failure probability and faultiness level, signal normalization for deteriorating sensors 18, and circuit fault re-routing and isolation.

To provide for fault recovery of various kinds, re-use of existing components or installation of additional components can be useful.

Referring now generally to the Figures and particularly to FIG. 30, FIG. 30 illustrates an example of possible additional circuitry 261 configured to implement the fault recovery system 254. For example, the additional circuitry includes logic 262, the connections of logic 262 to lead 264 and lead 266 at junctions 268 and 270, and local power source or power storage devices, such as diode 272 and capacitor 274. The additional circuitry also includes switches 276-278.

Another essential criterion is having a logic element with the ability to communicate with the pacemaker 20. The pacemaker 20 will store the profiles 256 of component states and the re-programming software algorithms. Logic 262 can communicate with a pacemaker 20 through a mechanism described by Zdeblick, PCT Patent Application "Methods And Apparatus For Tissue Activation And Monitoring", PCT/US05/031559, Sep. 1, 2005.

Under the control of the pacemaker 20, or potentially under the control of logic 262 acting autonomously, switches 276 and 278 can be opened or closed, isolating or providing satellite 26 from the power provided through leads 264 and 266. Logic elements and switches 262-278 between satellites 26 and electrodes 16.A, 16.B, 16.C, and 16.D can be included to switch on and off particular electrodes 16.A, 16.B, 16.C, and 16.D (not shown). The combination of switches and logic elements in electrical pathways 262-278 and active components of the first system 34 reconnect and reprogram deteriorating or failed first electrode 16.A, connect alternative or redundant electrical pathways, isolate a failed first electrode 16.A, open a short, and more.

Software algorithms and component profiles can be stored in the pacemaker 20, or other parts of the second system 232. Under ideal condition, the software will send signals to components of the first device 34 to accomplish a particular task, such as delivering a cardiac pulse 160 the patient or returning the data of the sensors 18. Under non-ideal condition, such tasks either cannot be accomplished at all, or cannot be accomplished correctly. The software can reprogram components such that when a particular task is required of a component, the command triggers other components to act instead of the original intended component. For example, a defective electrode 16.A might be instructed to deliver a cardiac pulse 160 the patient. However, the software can reprogram its instructions such as whenever the defective electrode 16.A is instructed to deliver a cardiac pulse 160 the patient, the first electrode 16.A will be isolated from the circuitry, and instead a second electrode 16.B or a third electrode 16.C will be activated as to reconstruct the signal intended to originate from defective first electrode 16.A. This type of software reprogramming opens up new possibilities for higher accuracy fault correction mechanisms within the invented fault recovery and detection system 254.

When the fault detection algorithm delivers the information that a particular component such as a satellite 6 or electrode 16.A has a hard failure, the fault recovery algorithm in the fault recovery and detection system 254 will be able to select a neighboring component 26, 16.A as a direct replacement for the failed first electrode 16.A automatically. If such direct replacement cannot be found, a combination of multiple satellites 26 sensors 18 and/or electrodes 16.B, 16.C and 16.D to reconstruct the intended signal then will be necessary.

For example, if the failed electrode is the first electrode 16.A or a sensor 18, the goal of the fault recovery system 254 is to find the closest replacement of a failed shocking/modulating electrode. Depending on the complexity of the fault detection algorithm used, it is possible to know exactly which electrode 16.A failed. If the complexity of the fault detection algorithm is low, the fault recovery algorithm can perform a trial-and-error test until the entire second system 232 performs the same as observed before. If the fault detection algorithm is comprehensive, the component profile 256 of FIG. 29 will show exactly which component 16.A has failed, and if it is a degradation or a complete hard failure.

To accomplish the goal of finding the closest replacement electrode 16.B, 16.C and 16.D of the failed first electrode 16.A, the fault recovery algorithm can use one or more of the distal or proximal electrodes 16.B, 16.C and 16.D to recreate the pulse signal 160 that would be most similar to that of the failed first electrode 16.A. If there are functional and non-deteriorated electrodes 16.B, 16.C and 16.D nearby, a single alternate electrode 16.B, 16.C and 16.D might be able to replace the failed electrode 16.B, 16.C and 16.D.

If there are two or more electrodes 16.B, 16.C and 16.D in the proximity but cannot individually function as a direct replacement, the fault recovery algorithm will attempt to use the two or more electrodes 16.B, 16.C and 16.D together to recreate the pulse signal 160 as delivered by the failed first electrode 16.A. The fault recovery algorithm accomplishes this by iterating through combination of signals in two or more proximate electrodes 16.B, 16.C and 16.D and comparing this combined signal to the historical states of the failed first electrode 16.A, back when the failed first electrode 16.A was still functioning effectively.

If the historical state of the failed first electrode 16.A is not available, the fault recovery algorithm may simply run consistency tests or request clinical observations to see if the replacement components create a consistent pacing pulse profile subject to clinical doctors' and engineers' affirmation.

This type of reprogramming and replacement algorithm may also be applied to sensors 18 of the first device 34. However, instead of iterating through a single neighboring sensor 18 or electrode 16.B, 16.C and 16.D for replacement, the algorithm can iterate through single neighboring sensors 18 or electrodes 16.B, 16.C and 16.D for replacing the function of the failed first electrode 16.A or failed sensor 18. When a single replacement sensor 18 cannot be found, the fault recovery algorithm will iterate through combination of sensing data from two or more proximate sensors 18 given a static control signal. Then the fault recovery algorithm compares the resulting signals with the historical sensing data from the failed sensor 18. As with the failed first electrode 16.A, if the historical state of the failed sensor 18 is not available, the fault recovery algorithm may simply run consistency tests or request clinical observations.

When more information is provided from a supplemental fault detection algorithm, a fault recovery algorithm can provide fault correction with higher accuracy. A failure of an electrode 16.A or a sensor 18 can be a hard failure. However, it is possible that an electrode 16.A or a sensor 18 might only have degraded capabilities, and have not failed completely.

For example, where the first electrode 16.A or a sensor 18 is impaired, the signal gain/strength might have deteriorated to 70% of its original level. If the neighboring sensors 18 and electrodes 16.B, 16.C and 16.D have all deteriorated below 50% of their original performance levels, the intelligent fault recovery algorithm will not choose to implement a replacement sensor 18 or a replacement electrode 16.B, 16.C and 16.D. Even though the impaired sensor 18 or impaired first electrode 16.A exhibits degraded performance, the intelligent fault recovery algorithm may elect to accept continued application of the impaired sensor 18 or impaired first electrode 16.A as being superior to the performance achievable by The fault recovery algorithm will function differently when there is a proximate direct replacement sensor 18 or electrode 16.B, 16.C and 16.D that is still functioning close to its original 100% capacity. The intelligent fault recovery algorithm might choose to switch to this sensor 18 or electrode 16.B, 16.C and 16.D for all future signals intended to be sent to or from the impaired first electrode 16.A or a sensor 18.

Furthermore, in some scenarios, a deteriorating first electrode 16.A or a sensor 18 might need a supplemental proximate component to accomplish its function. For example, if a sensor is deteriorating, the fault recovery algorithm might not find a direct replacement, but instead select a proximate sensor 18 or electrode 18, 16.B, 16.C and 16.D to supplement or backup this deteriorating component. By combining the deteriorating first electrode 16.A or sensor 18 performance with one or more proximate sensors 18 or electrodes 18, 16.B, 16.C and 16.D, it is possible to approximately or fully substitute what the deteriorating sensor 18 or first electrode 16.A would have sensed or pulsed given its full capacity.

By weighing the probability of future fault and the present level of degradation, the reprogramming algorithm described above will be able to isolate the best subset of all components in the first device 34 to replace or substitute for the lacking performance of a deteriorating or failed first electrode 16.A or sensor 18.

Complex fault detection algorithms that supplement a fault recovery algorithm can include noise level detected in sensors 18. Using this information, the fault recovery algorithm of the fault recovery and detection system 254 will be able to subtract out the background noise from the data received in the sensors 18. Furthermore, instead of just recording noise floor amplitude, the fault detection algorithm can continuously construct and store a noise signal model that analyzes the features of the noise data in the temporal and frequency domain. This type of comprehensive model can normalize signals generated by the noisy environment in which the implantable devices reside. The accuracy and consistency of the sensors 18 can be improved even as the capabilities of a sensor 18 deteriorate.

Mechanisms in Provisional Patent Application "Fault Recovery for Implantable Device", 60/753,598 filed on Dec. 22, 2005 by Leichner, et al., provides many other methods of fault recovery for circuit faults. The methods of recovery include opening and closing switches to bypass circuit shorts, to isolate power from components, to open a short and more.

Figure 31:
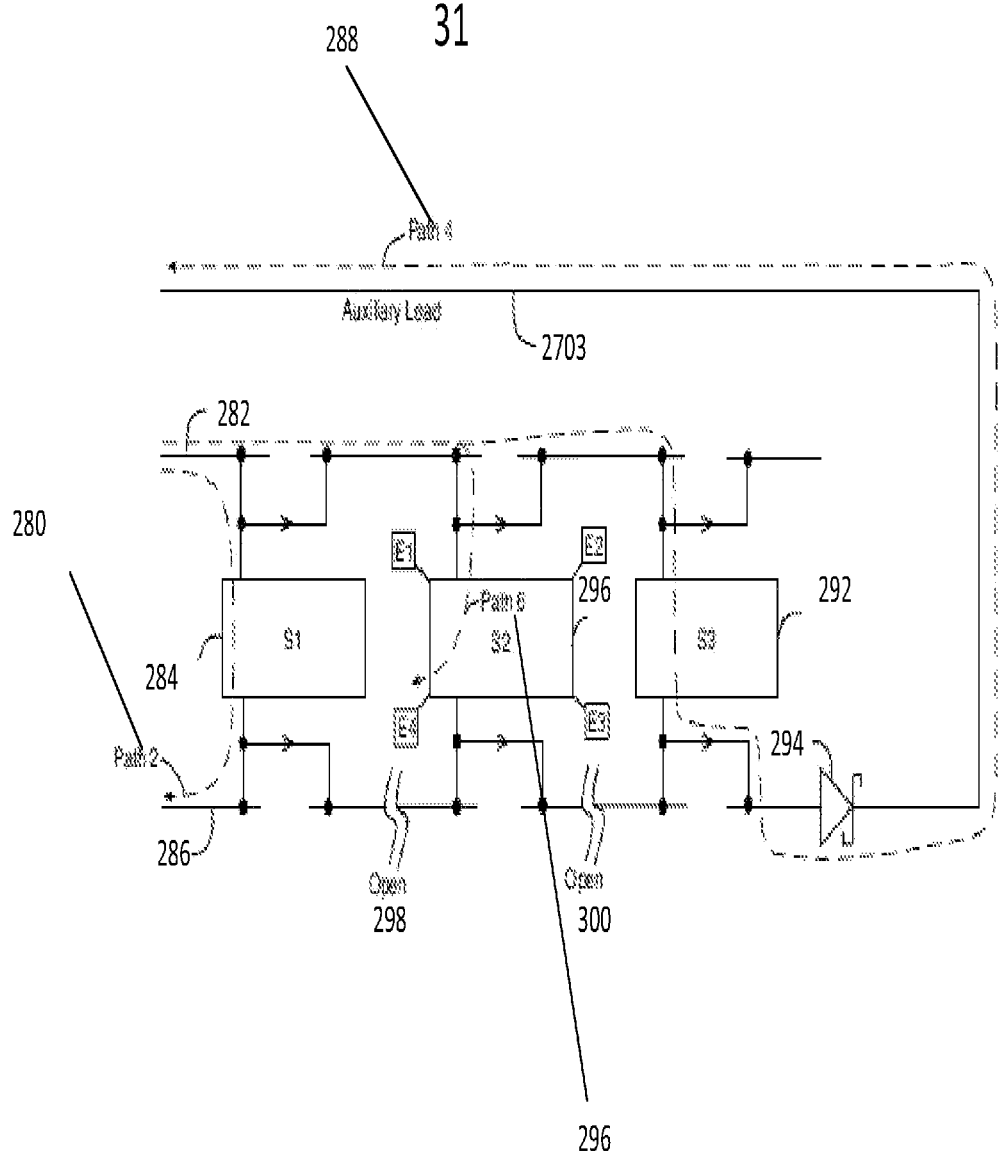
FIG. 31 illustrates one of the techniques for recovering from a fault, according to the fault recovery process of FIG. 27.

Referring now generally to the Figures and particularly to FIG. 31, FIG. 31 illustrates one of the techniques for recovering from a fault, according to a further embodiment of the present invention. Redundant circuit pathways are shown. In a second path 280, control flows from lead 282 through satellite 284 and returns on lead 286 following the second path 280. An additional recovery fourth path 288 uses the auxiliary lead 290. The recovery fourth path flows from lead 282 through satellite 292, through diode 294, and returning on auxiliary lead 290.

A third path 296 shown in FIG. 31 enables a satellite 302 to function even though open circuits 298 and 300 exists on lead 286, both proximal and distal to satellite 302. In this failure mechanism, no return paths exist along either lead 286 or auxiliary lead 290. In this situation, satellite 302 can revert to one-wire operation using just lead 282, while the remainder of the system, including satellites 284 and 292 continue to operate in a normal two-wire mode. Other circuit fault recovery mechanisms are described in Leichner et al. application referenced above.

Figure 32:
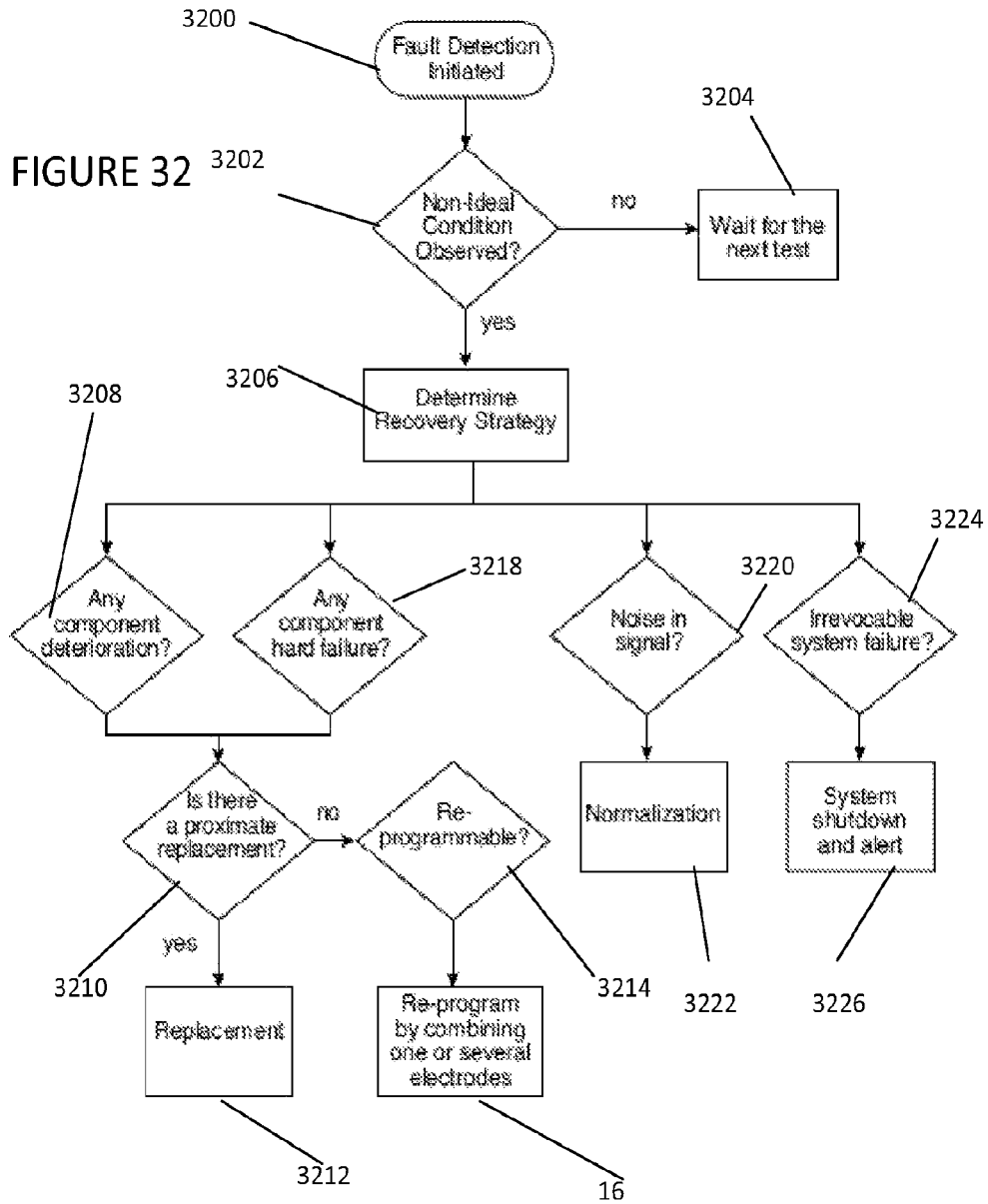
FIG. 32 illustrates the flow chart of one aspect of a fault recovery logic given the electrical component profile of the invented fault detection process of FIG. 27.

Referring now generally to the Figures and particularly to FIG. 32, FIG. 32 illustrates the flow chart of one embodiment of the fault recovery logic given the electrical component profile. FIG. 32 illustrates how when determining the recovery strategy, many parallel algorithms may be deployed to optimize the accuracy of fault correction.

The invented fault detection method is initiated in step 3200. The second system 232 determines whether any non-ideal conditions or performance is being observed in the first system 34. When the second system 232 does not detect non-ideal conditions or performance in step 3202, the second system 232 proceeds to step 3204 and to execute step 3200 at the next failure detest. When the second system 232 detects non-ideal conditions or performance in step 3202, the second system 232 proceeds to step 3206 to determine a recovery strategy.

Upon determining a recovery strategy in step 3206, the second system 232 may proceed to step 3208 to examine the first device 34 for deterioration of a lead 22, 24, and 25, a sensor 18, satellite 26, or an electrode 16.A, 16.B, 16.C and 16.D.

The second system 232 proceeds from step 3208 to step 3210 to search for a substitute sensor 18, satellite 26, or an electrode 16.B, 16.C and 16.D to substantially compensate for the deterioration of the impaired sensor 18 or the first electrode 16.A. The second system 232 may proceed from 3210 to step 3212 to effect one or more replacement sensors 18, satellites 26, or an electrodes 16.B, 16.C and 16.D as selected in step 3210. Alternatively, The second system 232 may proceed from 3210 to step 3214 to determine whether one or more lead 22, 24 and 25, satellite 26, sensor 18 and/or electrode 16.A, 16.B, 16.C and 16.D may be reprogrammed to compensate for the impaired performance observed in step 3202. The second system 34 may proceed from step 3214 to step 3216 to reprogram one or more lead 22, 24 and 25, satellite 26, sensor 18 and/or electrode 16.A, 16.B, 16.C and 16.D selected in the previous step 3214.

The second system 232 may alternatively proceed from step 3206 to step 3218 to examine the first device 34 for a total failure of a lead 22, 24, and 25, a sensor 18, satellite 26, or an electrode 16.A, 16.B, 16.C and 16.D. The second system proceeds from step 3218 to step 3210.

The second system 232 may still alternatively proceed from step 3206 to step 3220 to determine whether the non-ideal condition observed in step 3202 comprised electrical noise. The second system 232 may proceed from step 3220 to step 3222 to normalize observed noise.

The second system 232 may yet alternatively proceed from step 3206 to step 3224 to determine whether the non-ideal condition observed in step 3202 indicates an irrevocable system failure. When the second system 3224 determines that the non-ideal condition or performance observed in step 3202 indicates an irrevocable system failure, the second system 232 proceeds from step 3224 to step 3226 and to shut down the first device 34 and issue an alert message.

The fault detection algorithm in the fault recovery and detection system 254 improves the accuracy in arrhythmia detection and delivery of electrical pulses 160 by early detection of device component failures. The fault detection features component based fault detection, predictive trend analysis of component deterioration and failure probability weight profile.

There are two reasons to include the profile system in this invention. First, the component profile 256 can keep tracks historical characteristics of each component (such as signal strength, noise level and noise model) of each component in a database. Second, the component profile 256 keeps track of the current state of each component.

The first feature is useful in increasing the accuracy of the invented fault detection system 254. The signal strength, noise level and conductivity of each component relative to the profile of the past iteration give a good indication of deterioration of that particular electrical component. The second feature of the component profile 256 links together the fault detection algorithm and fault recovery algorithms to increase the effectiveness of the fault recovery algorithms. Historical states of each component allow the intelligence in the can to decide the best alternative in the reprogramming of the electrodes 16.A, 16.B, 16.C, and 16.D, replacement of failed first electrode's 16.A, normalization of sensor signals, and re-routing paths of circuit failures.

Figure 33:
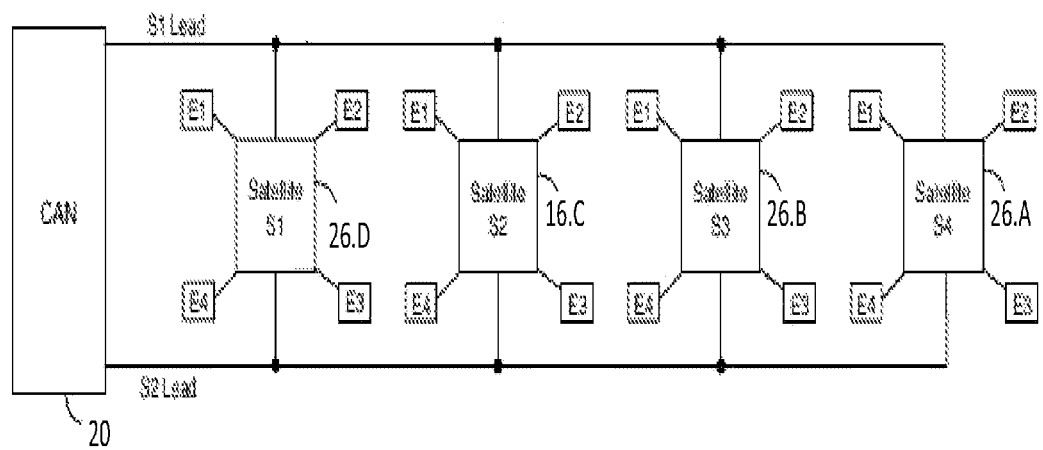
FIG. 33 shows a portion of the second system on which this invention can be implemented having the cathode wire and the anode wire that are coupled to multiple satellites of FIG. 5.

The fault detection in the present invention is useful in improving the detection mechanisms in implantable devices. Connections between sensing electronics and sensors 18 may be broken or operating with diminished effectiveness due to mechanical failure of connections, electrical failure of semiconductor devices, overgrown tissues or surface chemistry effects such as corrosion. Referring now generally to the Figures and particularly to FIG. 33, FIG. 33 shows a portion of the second system 36 on which this invention can be implemented having the cathode wire S1 and the anode wire S2 that are coupled to multiple satellites 26.A-26.D. Each of the satellites 26.A-26.D is coupled to four electrodes 16.A, 16.B, 16.C, and 16.D. A pacemaker 20 at the left of FIG. 33 drives the cathode wire S1 and the anode wire S2. Distributed along the cathode wire S1 and the anode wire S2 are four satellites 26.A-26.D, each of which has four pacing electrodes 16.A, 16.B, 16.C, and 16.D. The normal flow of control and power is from pacemaker 20 through the cathode wire S1 to each of the satellites 26.A-26.D and returning onto the anode wire S2 to the pacemaker 20.

Numerous failures are possible on a satellite's 26.A-26.D constellation of electrodes 16.A, 16.B, 16.C, and 16.D. A sensor 18 might fail completely due to an intervening event. The noise level on a selected sensor 18 of the first lead 22 of FIG. 4 might increase over time. Due to various reasons including tissue build-up, the sensitivity of these electrodes 16.A, 16.B, 16.C, and 16.D might also decrease. Shocking electrodes 16.A, 16.B, 16.C, and 16.D can fail completely due to an intervening event as well. Shocking electrodes 16.A, 16.B, 16.C, and 16.D can also fail gradually losing its signal strength or start producing signals that are not conforming to the instructions.

Numerous circuit failures are also possible on a lead system 22, 24 and 25.

Figure 34:
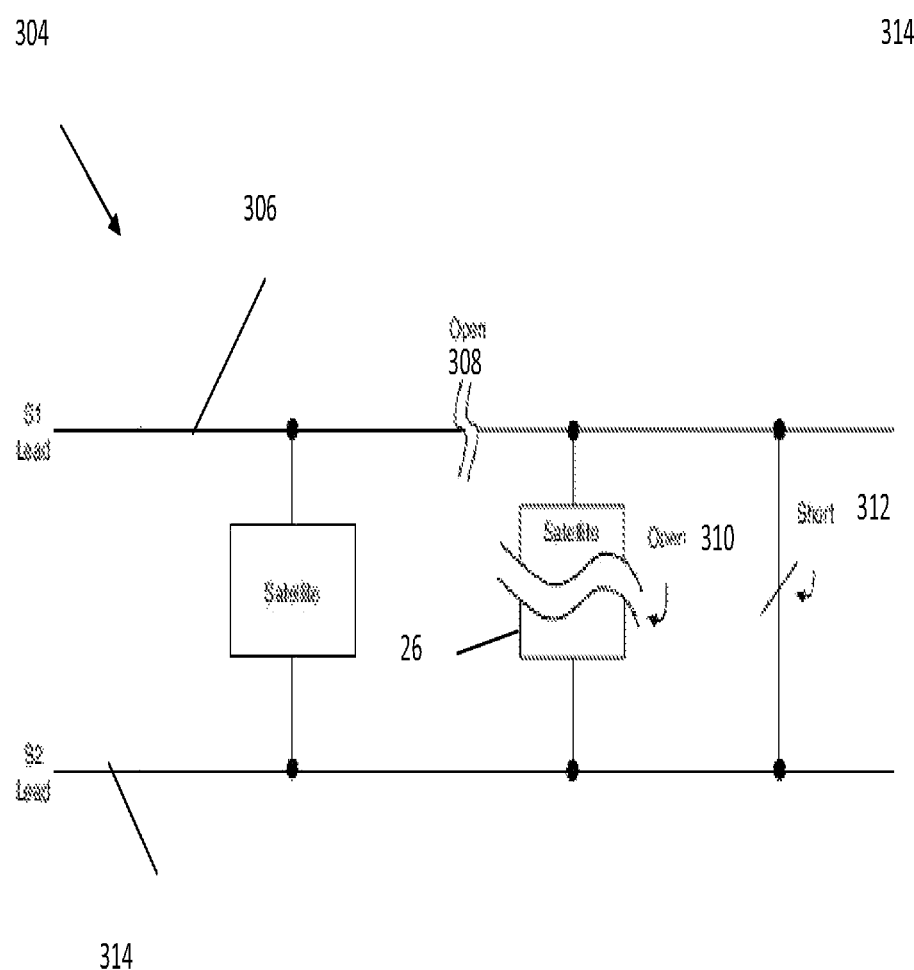
FIG. 34 shows an optional aspect of the exemplary first lead of FIG. 4.

Referring now generally to the Figures and particularly to FIG. 34, FIG. 34 shows an open circuit 304, where the cathode wire S1 providing a first lead 306 has an open fault 308. FIG. 34 also shows an open circuit 310 that has occurred in one of the satellites 26. A short 312 is a direct short between the first lead 306 and a second lead 314, wherein the second lead 314 is provided by the anode wire S2. The short 312 is a short circuit in one of the satellites 26 in the first device 34.

Partial faults are also possible. As an example, on the way to becoming a full short, a lead 306 and 314 may gradually fail, or conduction may gradually change. On the other hand, on the way to becoming a full open, partial lead breakages might be observable by noticing increase resistance over time.

In order to detect these failures, software containing this fault detection algorithm will need to interact with logic elements within the circuitry of the implantable first device 34. After assembling the information from turning on and off each component to measure the level of deterioration, the states (historical and current states) of the components is then stored in memory. Storage of this component profile can be located in memory of the can, or another place capable of communicating with the fault detection and fault recovery algorithms.

In order to generate a component state profile 256, the fault detection algorithm will iterate through isolated testing of individual components every year, month, day or other user defined time duration. This is illustrated by the possible parameter settings in FIG. 35. Users should be able to define the frequency of each testing scan, and the group of components to scan for each iteration. Different methods may be used to detect whether each component is deteriorating or is experiencing a hard failures.

Figure 36:
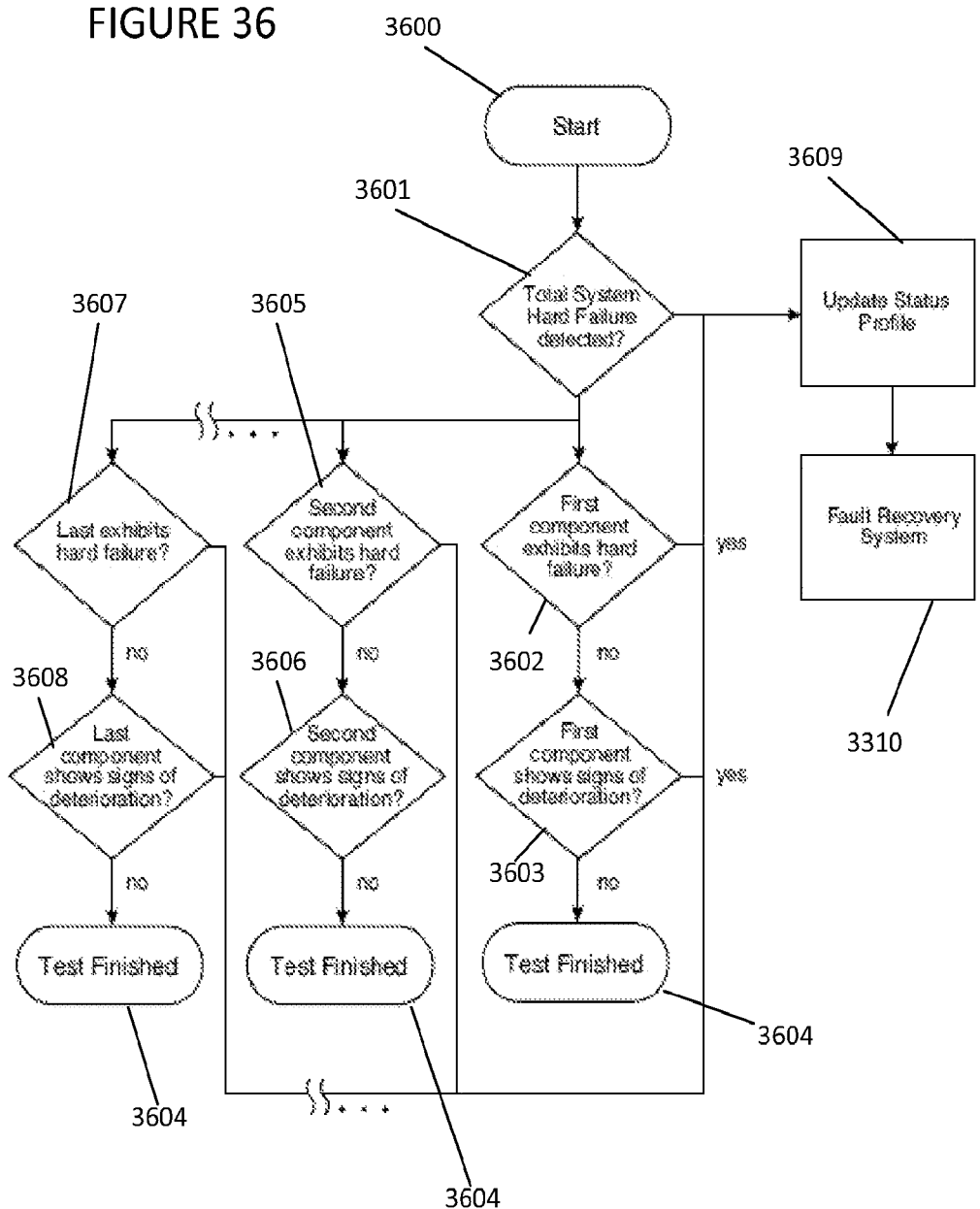
FIG. 36 is a flowchart of alternate aspects the invented fault detection algorithm of the method of FIG. 27.

Referring now generally to the Figures and particularly to FIG. 36, FIG. 36 is a flowchart of alternate aspects the invented fault detection algorithm in accordance with the method of the present invention. FIG. 36 shows an iterative process that checks one or more leads 22, 24 and 25, satellites 26, sensors 28, and/or electrodes 16.A, 16.B, 16.C and 16.D either in parallel or in series in terms of functional status and to update this information to the component status profile 256.

In step 3600 the process of the alternate aspects the invented fault detection algorithm, or "alternate method", is initiated by the second system 232. The second system 232 determines in step 3602 whether a total failure the second system 232 is detected. When the second system 232 does not observe a system hard failure, the second system 232 proceeds to step 3604 and updates the component status profile 256. The second system 232 further proceeds from step 3604 to step 3606 and to initiate the invented fault recovery process.

Alternately, when the second system 232 does not detect a system failure in step 3602, the second system 232 proceeds to serially execute steps 3608, 3610 and 3612 to separately determine whether indications of a hard failure in leads 22, 24 and 25, electrodes 16.A-16.D, sensors 18 have been observed. When the second system 232 determines in the steps 3608, 3610 and 3612 that a selected leads 22, 24 and 25, satellites 26, sensors 28, and/or electrodes 16.A, 16.B, 16.C and 16.D exhibits a hard failure, the second system proceeds from steps 3608, 3610 and 3612 to step 3604.

Alternately, when the second system 232 does not determine a hard failure in the steps 3608, 3610 and 3612 of a selected lead 22, 24 and 25, satellite 26, sensor 28, and/or electrode 16.A, 16.B, 16.C and 16.D, the second system 232 the second system proceeds respectively from step 3608 to step 3614, from step 3610 to step 3616, and/or from step 3612 to step 3618.

In steps 3614, 3616, and 3628 to separately determine whether indications of a performance deterioration in leads 22, 24 and 25, electrodes 16.A-16.D, sensors 18 have been observed. The second system 232 proceeds respectively from step 3614 to step 3620 and to update the component profile 232 with the results of step 3616. The second system 232 proceeds respectively from step 3616 to step 3622 and to update the component profile 232 with the results of step 3616. The second system 232 proceeds respectively from step 3618 to step 3624 and to update the component profile 232 with the results of step 3618.

One aspect of the invented fault detection system is disclosed in a mechanism described in commonly-assigned Provisional Patent Application "Fault Recovery for Implantable Device", 60/753,598 filed on Dec. 22, 2005 by Leichner, et al. By detecting the existence of an open circuit or a short, one would be able to locate which part of the first device 34 has a hard failure.

Another method of fault detection of components such as electrodes 16.A, 16.B, 16.C and 16.D, sensor 18 and satellites 26 is by utilizing the signal modulation capability of the components. For a signal generating component, the fault detection algorithm can shut off all signal generating as one or more electrodes 16.A, 16.B, 16.C and 16.D, sensors 18 and satellites 26 and measure the background signal with one or more sensors 18 of the first device 34. Then the fault detection algorithm can initiate test signal generation and send a test signal through it and measure the data received through the sensors 18.

If the sensors 18 do not detect the test signal, then a hard failure may be recorded in the component profile 256. If the signal strength of a sensor 18 is low or if there is noise in the data received through the sensors 18, then the level of degradation can be recorded keyed to this particular sensor 18 in the component status profile 256.

To prevent the possibility of a false positive, for each signal generating electrodes 16.A, 16.B, 16.C and 16.D, sensors 18 and satellites 26 under test, several sensors 18 should be used to guarantee that a detected failure does not arise out of a failed sensor 18. This acts as a consistency check to make sure that the failure detected occurred in the invented process is not due to the equipments of testing.

To test a sensor 18, the invented fault detection algorithm can first shutoff all sensors 18 of the first device 34. Then the fault detection algorithm can turn on several signal generating components known to be working. When the fault detection algorithm turns on a selected sensor 18, electrical signals should be detected through the selected sensor 18. If no signal is detected, then a hard failure of the sensor 18 should be recorded in the component profile 256. If some signal is detected during the test, but the noise in the signal is high or if the signal strength is low, then values of the amount of degradation should be recorded in the component profile 256.

To prevent a false positive determination, several patterns of generated signals should be used to test against individual sensors 18. This insures that the failure detected is specific to the sensor 18 under test and not to the signal generating electrodes 16.A, 16.B, 16.C and 16.D, sensors 18 and satellites 26 acting as test equipments.

If the signal strength of the past differs from the signal strength observed, then the fault recovery algorithm should record the possibility of degradation. By looking at ranges of signal strength between months, weeks, or days, the system will be able to calculate the slope of degradation and use this to modify the predictive profile status of the system.

Whenever a slow degradation is detected in a signal generating or sensor 18 instead of a hard failure, the degree of degradation and the rate of degradation can be recorded in certain embodiments of this invention. Degree of degradation can be recorded as a percentage of signal strength with respect to the initial signal strength or in signal to noise ratio. The rate of degradation can be recorded as a percentage over a period of time in the component profile 256.

In the more complex embodiments of the fault detection algorithm for the invented fault recovery and detection system 254, predictive deterioration trends are calculated and stored. By measuring intervals of signal strength and sensor sensitivity, the invented fault detection algorithm can calculate the rate of deterioration for electrical components such as shocking electrodes 16.A, 16.B, 16.C, and 16.D and sensing electrodes 18.

Complicated algorithms for electrical component deterioration trends are available in the art. Simple algorithms can also be implemented such as a linear trend analysis by measuring the difference in value between each trial divided by the time between each trial.

For example, if there is an initial signal strength that is expected out of a particular signal generating electrodes 16.A, 16.B, 16.C and 16.D, sensors 18 and satellites 26, and over a period of one year, the signal strength in amplitude decreases by half, then the rate of deterioration can be recorded as 50% over one year. Usually if over years, months, weeks or days the strength of signal decreases, then it can be assume that the slope of degradation will continue.

The deterioration rate of electrodes 16.A, 16.B, 16.C and 16.D, sensors 18 and satellites 26 can be useful in different fault recovery algorithms. In the synergistic mode of operation between the fault recovery algorithm and the fault detection algorithm described herein, the deterioration rates can be useful in eliminating bad alternatives in the selection of replacements for a failed or failing electrodes 16.A, 16.B, 16.C and 16.D, sensors 18 and satellites 26. This process eliminates possible alternative components that the fault recovery algorithm may use. Each electrode 16.A, 16.B, 16.C and 16.D, sensor 18 and satellite 26 may work now, but will likely fail later.

There are various failure mechanisms that may result in a changed impedance between the cathode wire S1 and the anode wire S2 conductors of the exemplary first lead 22. The invented fault recovery and detection method has the capacity to distinguish these failure mechanisms, as well as predict potential failure breaches between the cathode wire S1 and anode wire S2.

The impedance measurements of the inverted fault recovery and detection method are a result of passing a current between the cathode wire S1 and anode wire S2 and measuring the amount of current that flows when a voltage is impressed across the cathode wire S1 and anode wire S2. That voltage may be in the form of an electric tomography signal or a pacing pulse, among others.

Figure 37:
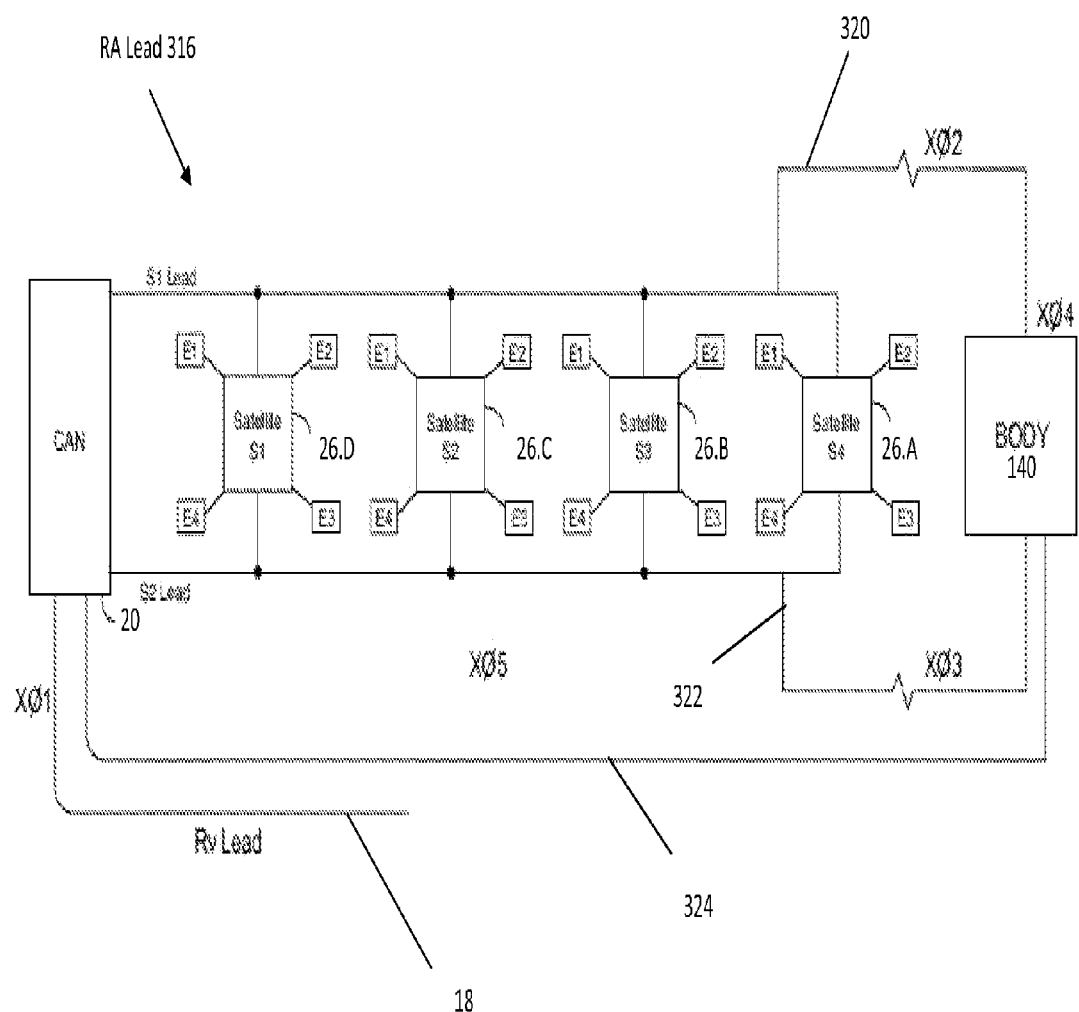
FIG. 37 is an example of possible impedance pathways of the first device of FIG. 4.

Referring now generally to the Figures and particularly to FIG. 37, FIG. 37 is an example of the first device 34 showing an RA lead 316 comprising the cathode wire S1 and the anode wire S2 and an RV lead 318, two unintended current paths to the target body 140 from the cathode wire S1 and anode wire S2, i.e. a first unintended current path 320, a second unintended path 322, and a third unintended current path 322 pass from the target body 20 to the pacemaker 20 The impedance measurements between the cathode wire S1 and the anode wire S2 can show a drop as a result of a number of different failure mechanisms. For example, one of the satellite controllers 40 that bridges the cathode wire S1 and the anode wire S2 may have an internal fault. In this case, there is no breach at the exemplary first lead 22 but one of the satellite controllers 40 has failed in a way that draws high current between the cathode wire S1 and the anode wire S2.

In another failure mechanism, there may be a breach in the outer conductors of the pacing leads 22, 24 and 25. In this case, internal conductors of the cathode wire S1 and the anode wire S2 are both exposed to conductive fluids or tissue of the target body 140. This mode of failure creates a low impedance path between the cathode wire S1 and the anode wire S2, as represented by the first unintended current path 320 and the second unintended current path 322.

Typically, the impedance measurements are conducted with all of the pacing electrodes 16.A-16.D disabled. In this alternate embodiment of the invnetd fault recovery and detection system 254, one or more electrodes 16.A-16.D are connected to the cathode wire S1 and the anode wire S2. This approach is possible where the pacing electrodes 16.A-16.D, and/or sensors 18, are in contact with fluids and tissues of the target body 140. By disconnecting the pacing electrodes 16.A-16.D and sensors 18, the first unintended current path 320 and the second unintended current path 322 to the target body 140 are eliminated. What remains is only the third unintentional path 324 with a connection to body fluid. Impedances is then measured between S1 and S2.

The results of this testing configuration will illustrate or uncover a low impedance situation between the leads. Running individual impedance measurements between cathode wire S1 and the pacemaker 20, and that anode wire S2 and the pacemaker 20 will disclose whether there were breaches in the lead sheath of the cathode wire S1 or the anode wire S2 that connected the cathode wire S1 or the anode wire S2 to the target body 140.

There is a predictive value to this embodiment as well. For instance, a detection that only the cathode wire S1 has predictive value. If there is a breach that has exposed one of the two conductors, the cathode wire S1 or the anode wire S2, the probability of a breach exposing the other conductor is higher once a first breach has occurred.

Increased impedance may also indicate a fault condition. As an example, an increased impendence between two pacing or sensing electrodes 16.A, 16.B, 16.C and 16.D may indicate a failing connection to one of the electrodes 16.A-16.D. Measuring impedance values between multiple pair of electrodes 16.A-16.D and comparing values to previously measured values may allow failures or changes in electrical characteristics to be isolated. Consider three electrodes 16.A, 16.B and 16.C with previous and current impedances measurements as shown below.

| Electrode Pair | Previous Impedance | Current impedance |
| --- | --- | --- |
| 16.A-16.B | 1000 Ω | 1200 Ω |
| 16.B-16.C | 1000 Ω | 1200 Ω |
| 16.A-16.C | 1000 Ω | 1000 Ω |

These values indicate a increase of 200Ω on the second electrode 16.B. The increased impedance on the second electrode 16.B may be an indication of a degrading electrode 16.B which over time will fail (predictive value). The increase may also trigger software to select another electrode, possibly the first electrode 16.A, to replace the function of second impaired electrode 16.B. A third option is using the increased impedance measured for the inter-electrode test to adjust one or more parameters associated with the signals sensed by the second electrode 16.B. It is understood that this invented technique may be adapted to a drift in the sensor 18.

Figure 38:
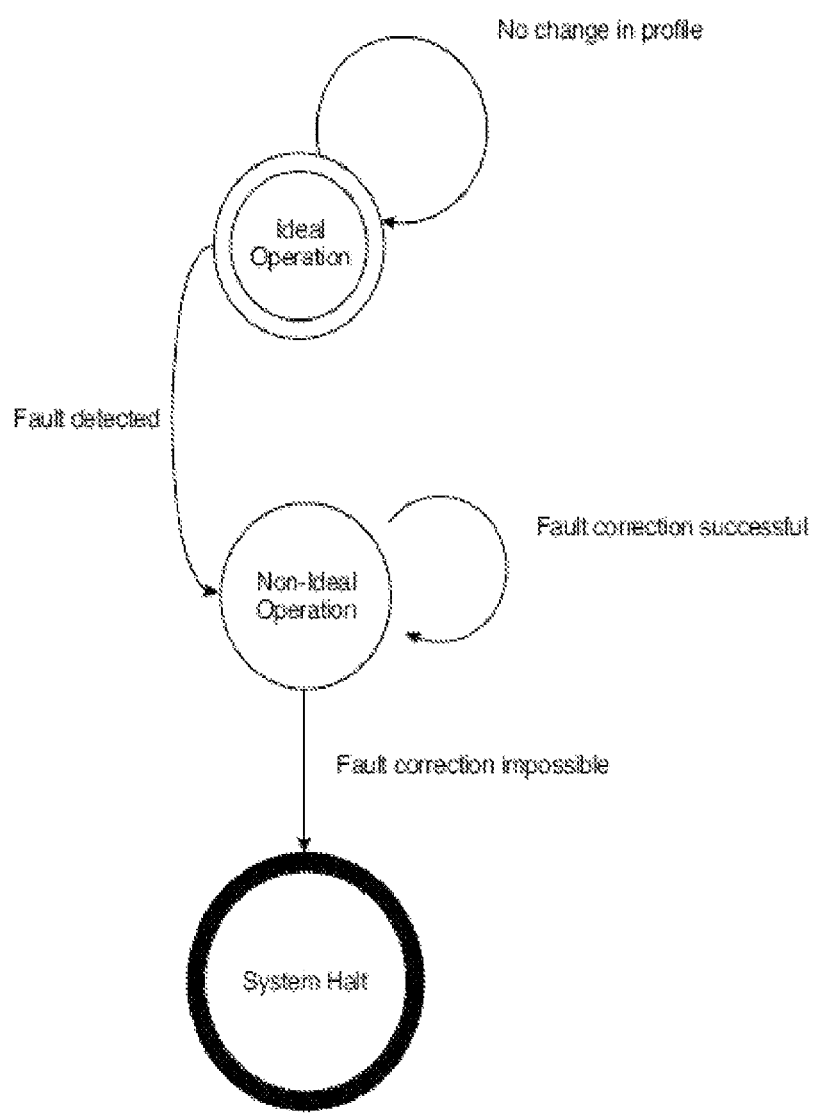
FIG. 38 shows a state diagram of the first device of FIG. 4 operating between the ideal versus non-ideal operation conditions.

Referring now generally to the Figures and particularly 38, FIG. 38 shows a state diagram of an implantable device operating between the ideal versus non-ideal operation conditions. Three states are illustrated including: (1) ideal operation where all components are assumed to be functional; (2) non-ideal operation where some components have degraded or failed, but the fault recovery algorithms have sustained the overall functionality of the implantable device; (3) and finally the system halt state where the fault detection algorithm or the fault recovery algorithm has concluded that significant hard failures must lead to a system halt. In the final state, professionals operating the implantable device will be notified.

The invented fault recovery and detection system 254 for implantable devices provides for an implantable device system design that achieves a lower device failure rate with component specific fault detection. It also can include fault corrective mechanisms. These correction methods are available even when the fault is detected by another system.

Unfortunately, malfunction of the individual components of a lead 22, 24 and 25 can trigger a functional failure of the first device 34. These failures can result in inappropriate non-therapeutic defibrillation shocks to the patient, which can be emotionally stressful to the patient, and occasionally fatal. Worse, malfunction of the individual components can result in failure to shock the patient in life threatening situations. Therefore, it would be desirable to provide a comprehensive system capable of component based fault profiling system to supplement a rigorous fault recovery system.

The fault recovery and detection system 254 has a fault detection algorithm with component profile 256 generation capability. It also has a fault recovery algorithm with component specific re-programming and re-routing capability. These two functionalities can, in some embodiments, be implemented together.

The fault recovery algorithm increases the success of fault correction efforts. The fault recovery algorithm has signal re-programming for failed electrodes, virtual component replacement through component re-selection, weighted selection of component replacement based on weighted failure probability and faultiness level, signal normalization for deteriorating sensors 18, and circuit fault re-routing and isolation.

The fault recovery algorithm in the fault recovery and detection system 254 has the advantage of component based fault correction. When failures occur locally in a few components, this feature is capable of reviving the entire systems. The fault recovery algorithm utilizes the redundancy in implantable second devices 34 to create recovery plans that are component specific. This allows the system to recover without compromising the specification of the medical implantable first device 34.

Picking up information relating to the location and deterioration rate of faults from whichever fault detection algorithm is used, the fault recovery algorithm of the system takes in a component status profile 256 as input. In some embodiments of the invention, where no fault detection algorithm is present, the fault recovery algorithm will attempt fixes in a trial-and-error manner until the fault is corrected or declared to be irreparable.

In some embodiments, the input can be in synergy with the fault detection functionality disclosed herein. This can be fault detection algorithm of the prior arts, or it can be the localized diagnosis including clinical observations in a doctor's office. In other embodiments, this can be the result of a fault detection algorithm based on trial and error as described above.

The fault recovery and detection system 254 is useful in resolving many current day therapy challenges. Arrhythmia detection algorithms based on sensed electrical activity in the heart can result in false positive detection and unnecessary shocks. Algorithms can also deliver false negatives failing to detect arrhythmia and failing to deliver a necessary shock. Algorithms can also deliver ambiguous results leading to delay while an arrhythmia becomes more severe.

Under ideal conditions, all elements of an arrhythmia detection mechanism are intact and functioning properly—processors are operating as designed, electrodes are properly placed and all connections are intact. Still, algorithms are not perfect and detection failures of various types can occur. Non-ideal conditions are also possible as the elements of the arrhythmia detection mechanism are subject to failures resulting in degraded system capabilities.

More pertinent to the fault recovery algorithm is the operation under non-ideal conditions. Using a profile 256 of component states, system elements can be assigned lower weights in algorithms reflecting the degraded quality of the generated or sensed signals. Degraded elements can be reported to care providers allowing for the possibility of manual reprogramming, replacement or repair prior to complete failure as. Alternative components can be enabled where such redundant or supplementary sensors 18 are available. Alternative components can be selected based on the weights of degradation of each of the components, optimizing for the lowest failure rate possible.

There are two critical considerations for power consumption in an implantable first device 34. In some embodiments, the battery chemistry has limited peak power draw. This limits the maximum power available to a feature in an implantable device. Li+ batteries are commonly used in pacemakers. Such batteries can source low 100's of µA. LiSVO batteries can source up to 2 amps.

The amount of average power draw adjusted for duty cycles determines the life time of battery use. The average power draw also limits how many additional features a device can support simultaneously. Typical average power draw for a pacemaker/defibrillator is less than 10 µA. An average power draw related to a new feature in a pacemaker/defibrillator that is less than 100 nA would typically be insignificant from a power draw stand point.

The power drawn while active during fault recovery ranges from less than 0.1 µW to 5 W, more specifically between 100 µW to 500 mW, and most specifically between 1 mW to 100 mW. The average power draw adjusted for duty cycle is much lower. The frequency of performing fault detection may be between once per hour to once per year, or between once per day to once per month, or between once day to once per week. Each cycle of fault recovery may range between 1 millisecond to 60 seconds, more specifically between 10 milliseconds to 5 seconds, and most specifically between 0.1 seconds to 2 seconds. The amount of additional real estate (measured by units of volume) required to implement this fault recovery algorithm including intelligent devices and switches may range between no additional space needed (only the installation of additional software) to requiring 1 cm$^3$ of additional volume, more specifically between 1 mm$^3$ to 500 mm$^3$, and most specifically between 10 mm$^3$ to 100 mm$^3$. The number of satellites, electrodes or circuit routes the fault recovery algorithm for implantable devices may cure per activation per second can range between 1 fault to 500 faults, such as 1 fault to 100 faults, including 1 fault to 10 faults.

The fault detection algorithm in the fault recovery and detection system 254 improves the accuracy in arrhythmia detection and delivery of shock by early detection of device component failures. The fault detection features component based detection, predictive trend analysis of component deterioration and weighted failure chance profile 256 for individual components.

The fault detection in the present invention is useful in improving the detection mechanisms in implantable devices. Connections between sensing electronics and sensing electrodes 18 may be broken or operating with diminished effectiveness due to mechanical failure of connections, electrical failure of semiconductor devices or surface chemistry effects such as corrosion.

An ideal system will have 1) mechanisms to improve detection accuracy under ideal conditions, and 2) methods to detect and properly weight degraded sense inputs available under failure conditions.

Under ideal conditions, where all electrical components are assumed to be functioning properly, fault detection can be measured through consistency test of multiple types of sensors 18. These consistency tests are triggered by events such as an onset of a possible arrhythmia. However, system integrity must be properly maintained before the onset of a life threatening event. Hence, more pertinent to the present fault detection algorithm is the operation under non-ideal conditions, where, periodically, components are scanned to make sure the system reliability prior to an onset of an event.

The fault detection algorithm in the fault recovery and detection system 254 provides mechanisms that are needed to detect degraded sensor performance and failed system elements. Early detection of failure, or even better, trend analysis pointing to eventual failure has several benefits. The fault recovery and detection system 254 constructs a comprehensive profile 256 of component states giving care providers and fault recovery algorithm a lot more information to work with. Degraded elements can be reported to care providers allowing for the possibility of replacement or repair prior to complete failure. Other benefits of this profile 256 of component states are most evident in conjunction with a fault recovery algorithm that uses the component profile 256 efficiently.

Detection methods often involve closing loops so that signals can be traced from input all the way to output. As an example, a signal generated by the can may be sent through a lead to an electrode and then sensed after it passes through body tissues back to the can. The effect on close loop detected signals can be observed as changes are programmed in electrode configurations. As an example, opening or closing a switch should yield a corresponding change in a signal passed through that switch.

Alternatively, signals normally present in the body such as EMG may be sampled over time. These signals may be expected to have relatively constant amplitude so that a change in amplitude of the signal is indicative of a change in the sense system. Relative amplitudes between detected signals on close by electrodes may be observed for changes over time as well.

The fault detection algorithm in the present invention has the advantage of providing a system wide profile 256 of each individual component. This information can be used to alert the doctors in certain embodiments of this invention. The system wide profile 256 can be used in conjunction with other fault recovery of prior art. This information can also be used in conjunction with the fault recovery algorithm of the system for the implantable device.

The power drawn while active during fault detection ranges from less than 0.1 µW to 5 W, more specifically between 100 µW to 500 mW, and most specifically between 1 mW to 100 mW. The average power consumption adjusted for duty cycle is much lower.

The frequency of performing fault detection may be between once per hour to once per year, or between once per day to once per month, or between once day to once per week. Each cycle of fault detection may range between 1 millisecond to 60 seconds, more specifically between 10 milliseconds to 5 seconds, and most specifically between 0.1 seconds to 2 seconds.

The amount of additional "real estate" on the integrated circuit chip (measured by units of volume) required to implement this fault detection algorithm including intelligent devices and switches may range between no additional space needed (only the installation of additional software) to requiring 1 $cm^3$ of additional volume, more specifically between 1 $mm^3$ to 500 $mm^3$, and most specifically between 10 $mm^3$ to 100 $mm^3$.

The number of elements such as satellites, electrodes, and circuit lines the detection algorithm may track overtime in its profile 256 range between 1 to 500 elements, such as 1 to 100 elements, and including 1 to 50 elements.

Finally, the two algorithms can work together synergistically in a variety of designs. The fault detection algorithm in the present invention can give a complex profile 256 of the fault location and deterioration rate. The fault recovery algorithm in the fault recovery and detection system 254 may be designed to save computation time and trial-and-error time using the complex profile 256 to accurately correct faults.

When implementing and selecting particular embodiments of the fault recovery and detection system 254 for implantable devices, one must balance the complexity, cost, energy consumption and size of the embodiment. Methods of detection can range between a plain and simple clinical guesswork to a highly component-specific fault detection algorithm. Methods of fault recovery can range between trial-and-error fixes to component specific fixes. The higher complexity of a particular algorithm usually means the need for higher energy consumption, higher cost and more additional space in implantable devices.

Usually, the complexities of the two algorithms in the fault recovery and detection system 254 for implantable devices are inversely proportional. A highly complex fault recovery algorithm likely only needs a plain and simple fault detection algorithm. This is because the complex fault recovery algorithm might deploy trial-and-error fixes when little information is known about where the fault is. If the fault detection algorithm is highly specific, then the fault recovery algorithm can be simple and efficient. With detail knowledge of where the fault has occurred and where functional replacement components are, the fault recovery algorithm will be able to quickly pin point the fault and find a proper replacement.

While the present invention has been described with reference to the specific applications thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The foregoing disclosures and statements are illustrative only of the present invention, and are not intended to limit or define the scope of the present invention. The above description is intended to be illustrative, and not restrictive. Although the examples given include many specificities, they are intended as illustrative of only certain possible applications of the present invention. The examples given should only be interpreted as illustrations of some of the applications of the present invention, and the full scope of the Present Invention should be determined by the appended claims and their legal equivalents. Those skilled in the art will appreciate that various adaptations and modifications of the just-described applications can be configured without departing from the scope and spirit of the present invention. Therefore, it is to be understood that the present invention may be practiced other than as specifically described herein. The scope of the present invention as disclosed and claimed should, therefore, be determined with reference to the knowledge of one skilled in the art and in light of the disclosures presented above.

What is claimed is:

1. An implantable system, comprising:
   (a) a plurality of implantable integrated circuits, wherein each of the implantable integrated circuits is coupled to at least one lead line and wherein the each of the implantable integrated circuits is configured to derive electrical power from the and at least one lead line;
   (b) a plurality of electrodes and sensors coupled to the plurality of implantable integrated circuits; and
   (c) a controller communicatively coupled to the plurality of the implantable integrated circuits via the at least one lead line, the controller configured to:
   detect a fault with an electronic component among the at least one lead line, the plurality of implantable integrated circuits, and the plurality of electrodes and sensors;
   correct the fault with the electronic component using a recovery strategy comprising a virtual component replacement through component re-selection based on component performance profiles of the at least one lead line, the plurality of implantable integrated circuits, and the plurality of electrodes and sensors; and
   update the component performance profiles and store the component performance profiles in a memory coupled to the controller.

2. The implantable system according to claim 1, further comprising protection circuitry for each of the implantable integrated circuits, the protection circuitry being activated when one of the at least one lead line is increased in voltage to greater than about 5.5 V.

3. The implantable system according to claim 2, wherein the protection circuitry comprises:
   (a) a resistor divider network coupled to a first interface signal via a switch;
   (b) a transistor coupled to a first supply, and controllable by a node of the resistor divider network; and
   (c) a buffer configured to receive an output from the transistor, and to open the switch when the first interface signal is greater than a first predetermined level.

4. The implantable system according to claim 3, further comprising a second supply coupled to the resistor divider network, and a third supply configured to be a diode drop below the second supply.

5. The implantable system according to claim 1, wherein the at least one lead line is present in a lead.

6. The implantable system according to claim 1, the system further comprising:
   an in-body computing system in communication with the controller; and
   an external impedance stabilizer, the external impedance stabilizer having a configuration mode in which all of the plurality of electrodes and sensors are decoupled from the in-body computing system and an operating mode in which selected electrodes and sensors of the plurality of electrodes and sensors are coupled to the in-body computing system.

7. The implantable system according to claim 6, further comprising: a circuit adapted to, while the external impedance stabilizer is in the configuration mode, configure the plurality of electrodes and sensors by selecting which electrode and sensor of the plurality of electrodes and sensors are to be coupled to the in-body computing system during the operating mode.

8. The implantable system according to claim 7, wherein, while the external impedance stabilizer is in the operating mode, the external impedance stabilizer decouples the circuit from the in-body computing system.

9. The implantable system according to claim 6, wherein the in-body computing system is selected from the group consisting of a cardiac pacemaker and an implantable cardiac defibrillator.

10. The implantable system according to claim 6, wherein the recovery strategy further comprises signal re-programming for at least one failed component, weighted selection of component replacement based on weighted failure probability and faultiness level, signal normalization for deteriorating sensor components, and circuit fault re-routing and isolation.

11. The implantable system according to claim 10, wherein the controller is configured to iteratively apply the recovery strategy until satisfactory operation of the implantable system is achieved.

* * * * *